(12) United States Patent
Wakamiya

(10) Patent No.: US 7,612,174 B2
(45) Date of Patent: Nov. 3, 2009

(54) SCAVENGER RECEPTOR

(75) Inventor: Nobutaka Wakamiya, Hokkaido (JP)

(73) Assignee: Fuso Pharmaceutical Industries, Ltd., Osaka (JP)

( * ) Notice: Subject to any disclaimer, the term of this patent is extended or adjusted under 35 U.S.C. 154(b) by 410 days.

(21) Appl. No.: 11/716,893

(22) Filed: Mar. 12, 2007

(65) Prior Publication Data

US 2007/0231859 A1     Oct. 4, 2007

Related U.S. Application Data

(62) Division of application No. 10/203,860, filed as application No. PCT/JP01/00874 on Feb. 8, 2001, now Pat. No. 7,189,809.

(30) Foreign Application Priority Data

Feb. 14, 2000   (JP)   ............................. 2000-35155
Oct. 10, 2000   (JP)   ............................. 2000-309068

(51) Int. Cl.
    C07K 14/705   (2006.01)
    G01N 33/53    (2006.01)
    C12N 15/06    (2006.01)
    A61K 39/00    (2006.01)
(52) U.S. Cl. ..................... 530/350; 435/7.1; 435/449; 424/185.1
(58) Field of Classification Search .................. None
    See application file for complete search history.

(56) References Cited

U.S. PATENT DOCUMENTS 4,906,734 A   3/1990   Jensenius
5,270,199 A   12/1993  Ezekowitz

FOREIGN PATENT DOCUMENTS

| EP | 0 856 580 | 8/1998 |
|---|---|---|
| JP | 2-504581 | 12/1990 |
| JP | HEI-238683 | 9/1997 |
| JP | 10-237611 | 8/1998 |
| WO | WO-89/01519 | 2/1989 |
| WO | WO-98/55614 | 12/1998 |
| WO | WO-99/37767 | 7/1999 |
| WO | WO-00/11161 | 3/2000 |
| WO | WO-00/68380 | 11/2000 |
| WO | WO-01/81401 | 11/2001 |

OTHER PUBLICATIONS

Nakamura, K. et al., "Molecular Cloning and Functional Characterization of a Human Scavenger Receptor with C-type lectin (SRCL), a Novel Member of a Scavenger Receptor Family", Feb. 2001, Biochem. and Biophys. Res. Comm., vol. 280: pp. 1028-1035.*
Adams et al., "Initial Assessment of Human Gene Diversity and Expression Patterns Based Upon 83 Million Nucleotides of cDNA Sequence," Nature 377 (Supp): 3-174 (Sep. 1995).
Bork et al. Powers and pitfalls in sequence analysis: the 70% hurdle, Genome Res. Apr. 2000;10(4):398-400.
Botas et al., "Altered surfactant homeostasis and alveolar type II cell morphology in mice lacking surfactant protein D," Proc. Natl. Acad. Sci. USA 95: 11869-11874 (1988).
Database Assession No. R78202 (XP-002242031), Database EMBL Online, EBI (2003).
Database EMBL, Online!, Homo sapiens chromosome 18, Nov. 22, 1999, XP002279619.
Doetschman T. Interpretation of phenotype in genetically engineered mice, Lab Anim Sci. Apr. 1999;49(2):137-43.
Drickhamer, K. "Two Distinct Classes of Carbohydrate-recognition Domains in Animal Lectins," The Journal of Biological Chemistry 263 (20): 9557-9560 (1988).
Epstein, et. al., "The collectins in innate immunity," Current Opinion in Immunology, 8:29-35 (1996).
Ezekowitz, R. A. B. et al., "A Human Mannose-binding Protein is an Acute-phase Reactant that Shares Sequence Homology with Other Vertebrate Lectins," J. Exp. Med., 167:1034-1046 (Mar. 1988).
Ezekowitz, R. A. B. et al., "Mannose-binding protein and susceptibility to chronic hepatitis B infection," The Lancet, 348: 1396-1397 (Nov. 1996).
Fujita, T. "Complement Activation and Lectin Pathway," Rinsho-Meneki, 29(3): 405-410 (1997). (Japanese with English abstract translation).
Garred, et al., "Susceptibility to HIV infection and progression of AIDS in relation to variant alleles of mannose-binding lectin," The Lancet, 349:236-240 (Jan. 1997).
Hakansson et al. Collectin structure: a review, Protein Sci. Sep. 2000;9(9):1607-17.
Hansen et al. Structural aspects of collectins and receptors for collectins, Immunobiology. Aug. 1998;199(2):165-89.
Hoppe et al., "Collectins-soluble proteins containing collagenous regions and lectin domains- and their roles in innate immunity," Protein Science 3: 1143-1158 (1994).

(Continued)

Primary Examiner—Michael Burkhart
(74) Attorney, Agent, or Firm—Marshall, Gerstein & Borun LLP

(57) ABSTRACT

Novel scavenger receptors having an SR structure and a collectin-like structure are provided, which can be utilized in the elucidation of mechanisms of macrophage and basic immunity; in the elucidation of mechanisms of the development of a wide variety of diseases such as arteriosclerosis, diabetic complications and Alzheimer's disease, hyper β-lipoproteinemia, hypercholesterolemia, hypertriglyceridemia, hypo α-lipoproteinemia, transplantation, atherectomy, post angiogenic restenosis, bacterial infections; in the diagnostic, prophylactic and therapeutic methods thereof; and in the development of reagents and drugs for the same. The novel scavenger receptors include proteins comprising an amino acid sequence set out in SEQ ID NO: 2, 4 or 24 or proteins having equivalent properties to the same, or derivatives or fragments thereof as well as isolated polynucleotides comprising a nucleotide sequence encoding these proteins, and related molecules such as antibodies, antagonists and the like. Also disclosed are methods for the treatment using the same.

9 Claims, 8 Drawing Sheets

OTHER PUBLICATIONS

International Search Report for PCT/JP01/00874, mailed Mar. 21, 2001.

Kawai, T. et al., "Cloning and characterization of a cDNA encoding bovine mannan-binding protein," Gene, 186(2):161-165 (Feb. 1997).

Kodama T., et al., "Type I macrophage scavenger receptor contains alpha-helical and collagen-like coiled coils" Nature, 343:531-535 (1990).

Krieger M., et al., "Structures and functions of multiligand lipoprotein receptors: macrophage scavenger receptors and LDL receptor-related protein (LRP)" Annu. Rev. Biochem., 63:601-637 (1994).

Kurata, H., "Structure and Function of Mannan-Binding Proteins Isolated from Human Liver and Serum," J. Biochem., 115(6):1148-1154 (1994).

Laursen et al., "Cloning and sequencing of a cDNA encoding chicken mannan-binding lectin (MBL) and comparison with mammalian analogues," Immunology 93:421-430 (1998).

Lim, B. L. et al., "Primary Structure of Bovine Collectin-43 (CL-43). Comparison with conglutinin and lung surfactant protein-D," J. Biol. Chem., 269(16):11820-11824 (Apr. 1994).

Lipscombe, R. J. et al., "Mutations in the Human Mannose-Binding Gene: Frequencies in several population groups," European Journal of Human Genetics, 4(1): 13-19 (1996).

Lu, et al., "Purification, characterization and cDNA cloning of human lung surfactant protein D," Biochem. J., 284: 795-802 (1992).

Malhortra et al., "Glycosylation changes of IgG associated with rheumatoid arthritis can activate complement via the mannose-binding protein," Nature Medicine, 1(3): 237-243 (Mar. 1995).

Malhortra et al., "Interaction of C1q receptor with lung surfactant protein A*," Eur. J. Immun., 22: 1437-1445 (1992).

Matsuda, M. et al., "Involvement of Mannan Binding Protein with crisis and progression of IgA nephrosis," Journal of Nephrology Association of Japan, 39(3): 235 (1997). (Japanese with English abstract translation).

Matsumoto A., et al., "Human macrophage scavenger receptors: primary structure, expression, and localization in atherosclerotic lesions" Proc. Natl. Acad. Sci. USA, 87:9133-9137 (1990).

Nakamura et al. Molecular cloning of a mouse scavenger receptor with C-type lectin (SRCL) (1), a novel member of the scavenger receptor family. Biochim Biophys Acta. Nov. 11, 2001;1522(1):53-8.

Nepomuceno, R. R. et al., "cDNA Cloning and Primary Structure Analysis of C1qR(P), the Human C1q/MBL/SPA Receptor That Mediates Enhanced Phagocytosis In Vitro," Immunity, 6(2):119-129 (Feb. 1997).

Ohtani et al. The membrane-type collectin CL-P1 is a scavenger receptor on vascular endothelial cells.J Biol Chem. Nov. 23, 2001;276(47):44222-8.

Ohtani et al., "Molecular Cloning of a Novel Human Collectin from Liver (CL-L1)," The Journal of Biological Chemistry 274(10):13681-13689 (1999).

Sastry, K. et al., "The Human Mannose-binding Protein Gene: Exon Structure Reveals its Evolutionary Relationship to a Human Pulmonary Surfactant Gene and Localization to Chromosome 10," J. Exp. Med., 170:1175-1189 (Oct. 1989).

Skolnick et al. From genes to protein structure and function: novel applications of computational approaches in the genomic era. Trends Biotechnol. Jan. 2000;18(1):34-9.

Smith et al. The challenges of genome sequence annotation or "the devil is in the details," Nat Biotechnol. Nov. 1997:15(12):1222-3.

Sumiya, et. al., "Mannose-binding protein, genetic variants and the risk of infection," Q. J. Med., 89: 723-726 (1996).

Sumiya, et. al., "Molecular basis of opsonic defect in immunodeficient children," Lancet, 337: 1569-1570 (Jun. 1991).

Super, et. al., "Association of Low Levels of Mannan-binding Protein with a Common Defect of Opsonisation," Lancet, 2: 1236-1239 (Nov. 1989).

Supplementary European Search Report, European Patent Office, Jun. 2, 2003.

Supplementary European Search Report for EP 01 90 2805 dated Jun. 3, 2004.

Suzuki et al., "Cloning and Sequencing of a cDNA Coding for Bovine Conglutinin," Biochem Biophys Res Commun, 191/2, 335-342 (1993).

Suzuki, et al., "Characterization of Recombinant Bovine Conglutinin Expressed in a Mammalian Cell," Biochem. Biophys. Res. Commun., 238: 856-863 (1997).

Tan et al., "Improvements on the Purificaiton of Mannan-Binding Lectin and Demonstration of its Ca2+-independent Association with a C1s-Like serine Protease," Biochem. J. 391:329-332 (1996).

Taylor, M. E. et al., "Structure and evolutionary origin of the gene encoding a human serum mannose-binding protein," Biochem J., 262: 763-771 (1989).

Thomas, et al., "Mutation of gene for mannose-binding protein associated with chronic hepatitis B viral infection," Lancet, 348: 1417-1419 (Nov. 1996).

Uemura, K. et al., "Correlation between Structure and Function of Calcium Dependence Animal Lectin on Host Defense," Jikken-Igaku, 13(18): (1995). (Japanese with English abstract translation).

Wakamiya, N. et. al., "Anti-Viral activity by Collectin," Rinsho-Meneki, 29(4): 508-513 (1997). (Japanese with English abstract translation).

Wakamiya, N. et. al., "Isolation and Characterization of Conglutinin as an Influenza A Virus Inhibitor," Biochem. Biophys. Res. Comm., 187: 1270-1278 (Sep. 1992).

Wakamiya, N. et. al., "The Mannose Binding Protein and Congulutinin in Bovine Serum Have a Antiviral Activity Against Influenza Virus," Glycoconjugate Journal, 8: 235 (1991).

* cited by examiner

```
Human MBP  MSLFPS-LPLLLLSMVAAS-YSETVTCEDAQKI----------CPAVIACSS---PGINGFPGKDGRDGTKGEKGEPG
Human SP-A MWLCPLALNLILMAAS----------GAACEVKDVC--------------------------------GSPG
Human SP-D MLLFLL-SALVLITQ-PLGYLEAEMKTYSHRTMP-SACTLVM-CSSVESGLPGRDGRDGREGPRGEKGDPG 140
           IPGTPGSHGLPGRDGR----------------DGVKGDPGPPGPMGPPG--------------------ETP
           LPGAAGQAGMPGQAGPVGPKGDNGSVGEPGPKGDTGPSGEPGPPGVPGPAGREGPLGKQGNIGPQGKPGP 210
                                   QGLRGLQGP-----------------PGKLGPPGNPGPSGSPGPKGDK
           CPPGNNGLPGAPGVPGE-------------RGEKGEPGERGPPGI
           KGEAGPKGEVGAPGMQGSAGARGLAGPKGERGVPGERGVPGNAGAAGSAGAMGPQGSPGARGPPGLKGDK
```

Human MBP
Human SP-A
Human SP-D

Fig. 2

```
Human MBP   GDPG-KSPDGDSSLAA----------SERKALQTEMARIKKWLTESLGKQVGNKFFLTNGEIMTFEKV
Human SP-A  --PAHLDEELQATLHD---FRHQILQTRGALS-LQGSI----------MTVGEKVFSSNGQSITFDAI
Human SP-D  GIPGDKGAKGESGLPDVASLRQQVEALQGQVQHLQAAFSQYKKVELFPNGQSVGEKIFKTAGFVKPFTEA  280

Human MBP   KALGVKFQASVATPRNAAENGAIQNLI----KEEAFLGITDEKTEGQFVDLTGNRLTYTNWNEGEPNNAGS
Human SP-A  QEACARAGGRIAVPRNPEENEAIASFVKKYNTYAYVGLTEGPSPGDFRYSDGTPVNYTNWYRGEPAGRG-
Human SP-D  QLLCTQAGGQIASPRSAAENAALQQLVVAKNEAAFLSMTDSKTEGKFTYPTGESLVYSNWAPGEPNDDG   350

Human MBP   DEDCVLLLKNGQWNDVPCSTSHLAVCEFPI*
Human SP-A  KEQCVEMYTDGQWNDRNCLYSRLTICEF*---
Human SP-D  SEDCVEIFTNGKWNDRACGEKRLVVCEF*---
```

Human MBP
Human SP-A
Human SP-D

Fig. 3

(A) OxLDL24
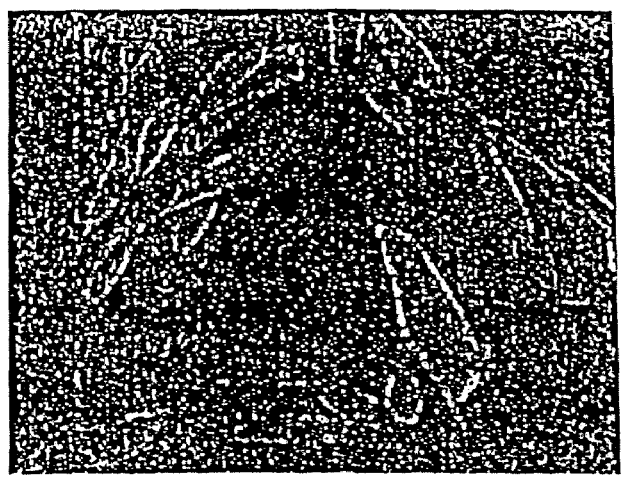
(B) mannose
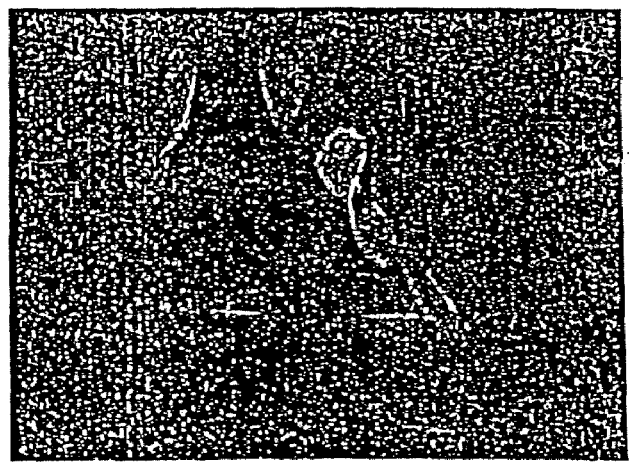
(C) AGE
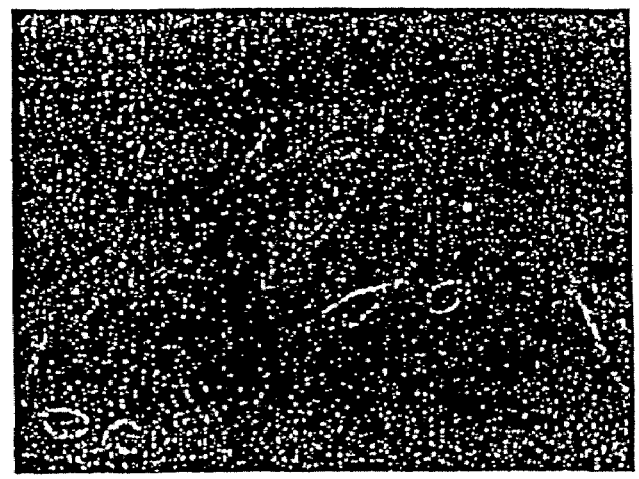
Fig.6

CHO/hSRCL-P1 : Green
Yeast : Red

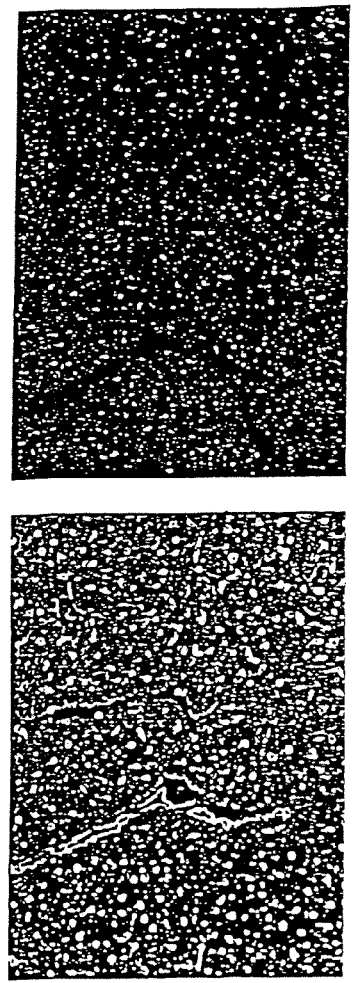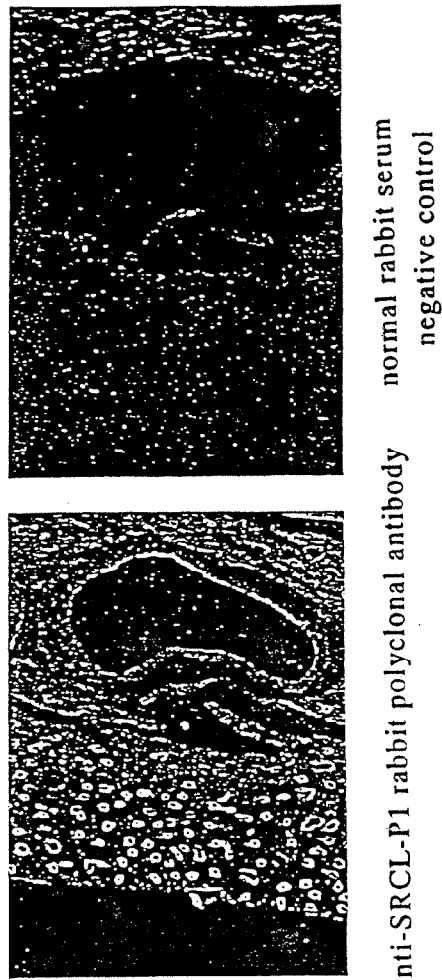
Fig.8

SCAVENGER RECEPTOR

This application is a divisional of U.S. patent application Ser. No. 10/203,860, now U.S. Pat. No. 7,189,809, filed Sep. 30, 2002, which is the U.S. national phase of PCT/JP01/00874, filed Feb. 8, 2001, which claims priority benefit of Japanese Patent Application No. JP 2000-35155, filed Feb. 14, 2000, and Japanese Patent Application No. JP 2000-309068, filed Oct. 10, 2000. All priority applications are hereby incorporated by reference in their entirety.

FIELD OF THE INVENTION

The present invention relates to isolated human and mouse novel scavenger receptors (herein referred to as "hSRCL-P1" and "mSRCL-P1" respectively, or merely as "SRCL-P1" when discrimination is not intended), genes and proteins, the homologues, mutants, modified forms and polymorphic variants thereof (these are collectively referred to as "derivatives"), fragments thereof (hereinafter collectively referred to as "SRCL-P1s" for all of these), and the detection thereof. The present invention further relates to compositions which comprise SRCL-P1s for pharmaceutical use, diagnostic use and research use, and methods for the production and use of the same. Additionally, the present invention relates to agonists and antagonists of SRCL-P1s proteins, as well as methods for screening drugs using SRCL-P1s. Moreover, the present invention relates to expression vectors comprising SRCL-P1s gene, transformed cells that were transformed with the expression vector, antibodies to SRCL-P1 protein, and cells that produce the antibody.

BACKGROUND OF THE INVENTION

Pathological features in lesions at an early stage of atherosclerosis involve the event of increase of foam cells in artery walls. Scavenger receptors (hereinafter abbreviated as "SR") that are present on a cell membrane of a macrophage (Krieger, M. et al., Annu. Rev. Biochem., 63, 601-637, 1994) lack negative feed back regulation by cholesterol, alien from LDL receptors. Thus, the receptor itself changes into foam cells through actively incorporatingsh modified LDL (low density lipoprotein that is a complex of cholesterol and a lipoprotein) to accumulate beneath the vascular endothelial cells. Therefore, macrophages and SRs thereof have been believed to play important roles in the establishment of pathosis of atherosclerosis (Brown, M. S. et al., Nature, 343, 508-509, 1990; Kurihara, Y. A. et al., Current Opinion in Lipidology, 2, 295-300, 1991; Krieger, M., TIBS, 17, 141-146, 1992; Krieger, M. et al., J. Biol. Chem., 268(7), 4569-4572, 1993).

Continuous hyperglycemia in a living body resulting from diabetes causes nonenzymatic glycation of various proteins, thereby leading the production of Maillard reaction-advanced end products (AGE: advanced glycation end products), which are final products in a glycation process via a Schiff base and an Amadori compound. AGE having an injurious action on cells adversely affects through the binding to macrophages, vascular endothelial cells, hepatic cells, renal mesangium cells and the like via AGE receptors. For example, it is known that secretion of cytokines such as TNF (Tumor Necrosis Factor), IL-1 (Interleukine-1) and platelet derived growth factor (PDGF) is accelerated upon binding of AGE to a macrophage, thereby causing cell injuries characteristic to diabetic complications. SR is believed to participate profoundly in diabetic complications such as diabetic nephropathy, diabetic retinopathy, diabetic neuropathy, on the basis of the findings that SR is one of the receptors involving in incorporation and degradation of AGE (Araki, N. et al., Eur. J. Biochem., 230, 408-415, 1995; Suzuki, H. et al., Circulation, 92, I-428, 1995), and that degradative activity of AGE is lowered to a level of third in an SR-double knockout mouse. Further, when an excessive AGE albumin is administered to a rat, AGE was found to deposit in kidney, thereby developing and glomerulosclerosis (Vlassara, H. et al., Proc. Natl. Acad. Sci. USA, 91, 11704-11708, 1994). Accordingly, SR, which recognizes AGE, is anticipated to profoundly involve in glomerulosclerosis.

In addition, SR is believed to involve in Alzheimer's disease. Pathological features of Alzheimer's disease concern senile plaques that are deposits of β-amyloid. β-amyloid has been reported to activate microglia cells via SRs that are expressed on the microglia cells to generate active oxygen, leading to the expression of neurotoxicity (Nature, 382, 716-719, 1996).

Examples of ligand for SRs include: ligands having negative charge, e.g., modified LDL such as acetylated LDL (AcLDL), oxidized LDL (OxLDL) and the like, modified proteins such as maleylated BSA and the like, quadruple helical nucleic acids such as polyinosinic acids and the like, polysaccharides such as dextran sulfate and fucoidane and the like, acidic phospholipids such as phosphatidylserine, phosphatidylinositol and the like, endotoxin (LPS), AGE, senile cells apoptotic cells, and the like, although differences in specificity thereof may exist depending on the differences of molecular species of SRs. Additionally, SR is believed to play an important role in removal of foreign substances, metabolic decomposition products and the like, because SR extensively recognizes various modified substances and a wide variety of foreign substances such as viruses in a living body (Hampton, R. Y. et al., Nature, 352, 342-344, 1991; Tokuda, H. et al., Biochem. Biophys. Res. Commun., 196(1), 8-24, 1993; Pearson, A. M. et al., J. Biol. Chem., 268, 3546-3554, 1993; Dunne, D. W. et al., Proc. Natl. Acad. Sci. USA, 91, 1863-1867, 1994; Freeman, M. W.; Current Opinion in Lipidology, 5, 143-148, 1994).

SRs have been expressed in hepatic sinusoidal endothelial cells (Eskild, W. et al., Elsevier Biomedical N.Y., 255-262, 1982), vascular endothelial cells (Baker, D. P. et al., Arteriosclerosis, 4, 248-255, 1984; Bickel, P. E. et al., J. Clin. Invest., 90, 1450-1457, 1992), blood smooth muscle cells (Pitas, R. E. et al., J. Biol. Chem., 265, 12722-12727, 1990; Bickel, P. E. et al., J. Clin. Invest., 90, 1450-1457, 1992), fibroblasts (Pitas, R. E. et al., J. Biol. Chem., 265, 12722-12727, 1990), and the like as well as in macrophages. Further, SRs have been classified into SRA, SRB, SRC (Peason, A. et al., Proc. Natl. Acad. Sci. USA, 92, 4056-4060, 1995), FcγRIIB2 (Stanton, L. W. et al., J. Biol. Chem., 270, 22446-22451, 1992) and macrosialin (CD68) (Ramprasad, M. P. et al., Proc. Natl. Acad. Sci. USA, 92, 9580-9584, 1995), human vascular endothelial OxLDL receptor (LOX-1: lectin-like oxidized LDL receptor) (Sawamura, T. et al., Nature, 386, 73, 1997). Moreover, SRA has been classified into SR-AI and SR-AII (Kodama, T. et al., Nature, 343, 531-535, 1990), and MARCO (a novel macrophage receptor with collagenous structure) (Elomaa, O. et al., Cell, 80, 603-609, 1995); SRB has been classified into CD36 (Endemann, G. et al., J. Biol. Chem., 268, 11811-11816, 1993) and SR-BI (Acton, S. L. et al., J. Biol. Chem., 269, 21003-21009, 1994).

SR-AI and SR-AII are homotrimers, which are of inside-out type transmembrane proteins of which N-terminus resides within the cell. The protein is structurally revealed to have several domains such as a collagen-like domain, α-helical coiled coil domain and a cysteine-rich domain, and the like in its extracellular portion (Rohrer, L. et al., Nature, 343, 570, 1990; Matsumoto, A. et al., Proc. Natl. Acad. Sci. USA, 87, 9133, 1990). The collagen-like domain has a structure characteristic in collagen, (Gly-Xaa-Yaa)n, wherein Xaa and Yaa may be any one of amino acid residues, and this domain functions as a ligand-binding site. The α-helical coiled coil domain is a dexiotropic hepted repeat which turns two times at every seven amino acids, namely having a structure of α-helical coiled coil. The three polypeptides form a homotrimer with hydrophobic amino acids such as leucine and isoleucine that are present at every seven amino acids being directed to inside of the molecule, whilst having polar amino acids and carbohydrate chain-binding site outside thereof (leucine zipper). Roles of the domains involve retention of the homotrimer structure, as well as binding to the ligands such as modified LDL to incorporate them into the cells, and changing a tertiary structure of the receptor depending on decrease of pH in endosome, finally resulting in the dissociation of the ligands.

Intracellular domain of the protein has a tight turn structure, which is characteristically found in an endocytotic signal, similarly to the structures including NPXY sequence found in LDL receptors or insulin receptors and YXRF sequence found in transferring receptors. It is suggested that endocytosis may be suppressed when these sequences are deleted.

SR-A1 and SR-A2 arise from alternative splicing of mRNA coding a cysteine-rich domain. SR-AI has 110 amino acids corresponding to the domain, whilst SR-AII has corresponding 17 amino acids. SR-AI and SR-AII are expressed in at least peripheral macrophage derived from monocyte, pulmonary alveolus macrophage and hepatic Kupffer cell. It is revealed that they participate in a host defense system in a living body, for example, arteriosclerosis, Calcium ion-independent cell adhesion and the like (Krieger, M. et al., Annu. Rev. Biochem., 63, 601-637, 1994; Wada, Y et al., Ann. N.Y. Acad. Sci., 748, 226-239, 1995; Fraser, I. P. et al., Nature, 364, 343, 1993). Further, OxLDL is present within macrophages of arteriosclerosis foci. In addition, SR-AI and SR-AII are abundantly expressed on the cell membrane of macrophage, and the elevation of blood lipoprotein by lipid absorption is suppressed in a transgenic mouse for SR-AI. Accordingly, it is envisaged that SR-AI and SR-AII play important roles in incorporation of Ox LDL.

To the contrary, although MACRO classified into SRA has a similar structure as that of SR-AI, it has no α-helical coiled coil domain, which is characterized by having a long collagen-like domain. MACRO is expressed in spleen macrophage, lymph node macrophage and the like, which is believed to function in a host defense mechanism against bacterial infection in a living body taking into account of the specificity of the ligands thereof.

Suzuki et al., successfully produced an SRA-knockout mouse through the substitution of the fourth exon that is a common part between SR-AI and SR-AII with a neomycin resistant gene (Suzuki, H. et al., Nature, 386, 292-296, 1997). Immune disorder has been observed in the SRA-knock out mouse in comparison with the wild type, and exhibits a high rate of infection with *Listeria* and herpes simplex virus. In addition, it is indicated that SRA participates in phagocytosis of T cells having apoptosis occurred, and that the phagocytic capacity is reduced in the SRA-knockout mouse in comparison with the wild type (Platt, N. et al., Proc. Natl. Acad. Sci. USA, 93, 12456, 1996). Furthermore, in a double knockout mouse obtained by the mating of the SRA-knock out mouse and an apoE deficient mouse (Plump, A. S. et al., Cell, 71, 343, 1992; Zhag, S. H. et al., J. Clin. Invest., 94, 937, 1994) that is an animal model for arteriosclerosis, it is indicated that the area of arteriosclerosis foci is significantly smaller than that of the apoE deficient mouse (Suzuki, H. et al., Nature, 386, 292-296, 1997).

Thus, SR can be utilized in the elucidation of functions of macrophage, the elucidation of mechanisms of development of various types of diseases including for example, arteriosclerosis, diabetic complications and AD, hyper β-lipoproteinemia, hypercholesterolemia, hypertriglyceridemia, hypo α-lipoproteinemia, transplantation, atherectomy, post angiogenic restenosis and the like, as well as diagnostic, prophylactic, therapeutic methods thereof, and in the development of reagents and drugs for the same. Accordingly, to find novel molecular species belonging to this family can be the means to solve the above-described problem to be solved.

Besides, a complement system that plays an important role in a host defense mechanism is known to include: a classical pathway in which an immunoglobulin serves as a recognition molecule followed by the activation of C1 that is the first component of the complement; and an alternative pathway in which C3, which is the third component of the complement, is directly coupled to foreign substances such as bacteria. In addition to these pathways of the complement activation, a lectin pathway was illustrated in which a mannose binding protein (hereinafter referred to as "MBP"), which is a serum lectin, activates the complement system through the direct recognition of and coupling with a carbohydrate chain on the surface of the foreign substance, in recent years (Sato, T. et al., Int. Immunol., 6, 665-669, 1994).

MBP is a C type lectin which specifically binds to mannose, N-acetylglucosamine and the like in the presence of Calcium ion, of which structure comprises a collagen-like domain containing at least (Gly-Xaa-Yaa)n, and carbohydrate recognition domain (CRD). Similarly to MBP, lectins having a collagen-like domain and CRD are generically called as collectin (Malhotora, R. et al., Eur. J. Immunol., 22, 1437-1445, 1992), which include collectin-43 (CL-43), surfactant protein A (SP-A), surfactant protein D (SP-D), bovine conglutinin (BKg) and the like, in addition to MBP. Collectin has an opsonic activity, which is believed to participate in basal immunity against a variety of microorganisms such as bacteria and viruses (Kawasaki, N. et al., J. Biochem., 106, 483-489, 1989; Ikeda, K. et al., J. Biol. Chem., 262, 7451-7454, 1987; Ohta, M. et al., J. Biol. Chem., 265, 1980-1984, 1990; Summerfield, J. A. et al., Lancet, 345, 886, 1995).

These collectins are known to constitute from a basic structure containing characteristic domains such as (1) CRD and (2) collagen-like domain and the like as shown in FIG. 1(*a*) (Malhortra et al., Eur. J. Immunol., 22, 1437-1445, 1992). This basic structure forms a subunit through composing a triple helix at the collagen-like domain, and thus these subunits further form an oligomer structure such as trimer, tetramer, hexamer and the like.

Recently, collectins were suggested to participate in nonspecific immune response, e.g., it was reported that for example, they are playing important roles in neutralizing and excluding various microorganisms in infants having maternal antibodies from the mother or nonspecific defense systems which were insufficiently developed (Super et al., Lancet, 2, 1236-1239, 1989). Moreover, results of investigation are reported involving in roles of these collectins in the body defense system of a host, which for example, suggest that the host becomes more susceptible to infections through the lowered concentration of MBP in blood resulting from genetic mutation of MBP (Sumiya et al., Lancet, 337, 1569-1570, 1991). In addition, it was reported that serum MBP content shows a lowered level upon the failure of opsonization (Madsen, H. O. et al., Immuno genetics, 40, 37-44, 1994), whilst bacterial infections readily occur (Garred, P. et al., Lancet, 346, 941-943, 1995). Therefore, MBP may be believed to play important roles in an immune system.

The present inventors previously found that BKg and MBP inhibit infections by H1 and H2 types influenzae A viruses as well as a haemagglutination activity (Wakamiya et al., Glycoconjugate J., 8, 235, 1991; Wakamiya et al., Biochem. Biophys. Res. Comm., 187, 1270-1278, 1992). Thereafter, a cDNA clone encoding BKg was obtained, and the relevance between BKg and SP-D and the like has been also found (Suzuki et al., Biochem. Biophys. Res. Comm., 191, 335-342, 1993).

Likewise, collectins are substances to which usefulness in the elucidation of host defense mechanism and utilities as a biologically active substance are expected. Thus, the finding of novel molecular species belonging to this family may greatly contribute in various medical fields and biological fields in addition to the therapy of infectious diseases.

DISCLOSURE OF THE INVENTION

The object of the present invention is to provide a novel scavenger receptor that can be utilized in the elucidation of mechanisms of macrophage and basic immunity; in the elucidation of mechanisms of the development of a wide variety of diseases such as arteriosclerosis, diabetic complications and Alzheimer's disease, hyper β-lipoproteinemia, hypercholesterolemia, hypertriglyceridemia, hypo α-lipoproteinemia, transplantation, atherectomy, post angiogenic restenosis, bacterial infections; in the diagnostic, prophylactic and therapeutic methods thereof; and for the development of reagents and drugs for the same.

Accordingly, the aspects provided by the present invention are as described below.

(1) A protein comprising an amino acid sequence consisting of 742 amino acids set out in amino acid position 1 to 742 of SEQ ID NO: 2, or a protein comprising an amino acid sequence set out in SEQ ID NO: 2 having deletion, substitution or addition of one or several amino acids therein and having an equal property to that of the protein comprising an amino acid sequence set out in amino acid position 1 to 742 of SEQ ID NO: 2, or a derivative or a fragment thereof;

(2) An isolated polynucleotide comprising a nucleotide sequence set out in nucleotide position 74 to 2299 of SEQ ID NO: 1, a nucleotide sequence encoding an amino acid sequence set out in amino acid position 1 to 742 of SEQ ID NO: 2 or a fragment thereof, or a nucleotide sequence that hybridizes to any one of said nucleotide sequences or nucleotide sequences complementary thereto under a stringent condition and encodes a protein having an equal property to that of the protein comprising an amino acid sequence set out in amino acid position 1 to 742 of SEQ ID NO: 2;

(3) A protein comprising an amino acid sequence set out in amino acid position 1 to 618 of SEQ ID NO: 24, or a protein comprising an amino acid sequence set out in SEQ ID NO: 24 having deletion, substitution or addition of one or several amino acids therein and having an equal property to that of the protein comprising an amino acid sequence set out in amino acid position 1 to 618 of SEQ ID NO: 24, or a derivative or a fragment thereof;

(4) An isolated polynucleotide comprising a nucleotide sequence set out in nucleotide position 74 to 1933 of SEQ ID NO: 23, a nucleotide sequence encoding an amino acid sequence set out in amino acid position 1 to 618 of SEQ ID NO: 24 or a fragment thereof, or a nucleotide sequence that hybridizes to any one of said nucleotide sequences or nucleotide sequences complementary thereto under a stringent condition and encodes a protein having an equal property to that of the protein comprising an amino acid sequence set out in amino acid position 1 to 618 of SEQ ID NO: 24;

(5) A protein comprising an amino acid sequence consisting of 742 amino acids set out in amino acid position 1 to 742 of SEQ ID NO: 4, or a protein comprising an amino acid sequence set out in SEQ ID NO: 2 having deletion, substitution or addition of one or several amino acids therein and having an equal property to that of the protein comprising an amino acid sequence set out in amino acid position 1 to 742 of SEQ ID NO: 2, or a derivative or a fragment thereof;

(6) An isolated polynucleotide comprising a nucleotide sequence set out in nucleotide position 74 to 2299 of SEQ ID NO: 3, a nucleotide sequence encoding an amino acid sequence set out in amino acid position 1 to 742 of SEQ ID NO: 2 or a fragment thereof, or a nucleotide sequence that hybridizes to any one of said nucleotide sequences or nucleotide sequences complementary thereto under a stringent condition and encodes a protein having an equal property to that of the protein comprising an amino acid sequence set out in amino acid position 1 to 742 of SEQ ID NO: 2;

(7) A vector comprising a polynucleotide according to (2), (4) or (6);

(8) A transformed cell carrying a polynucleotide according to (2), (4) or (6) in a manner to allow the expression;

(9) A method for the production of a protein which comprises the step of culturing a cell transformed with the polynucleotide according to (2) or (4), and collecting thus produced hSRCL-P1 protein;

(10) A method for the production of a protein which comprises the steps of culturing a cell transformed with the polynucleotide according to (6), and collecting thus produced mSRCL-P1 protein;

(11) The method according to (9) or (10) wherein said cell is *Escherichia coli*, an animal cell or an insect cell;

(12) A transgenic non-human animal having an altered expression level of SRCL-P1 gene;

(13) The transgenic non-human animal according to (12) wherein said SRCL-P1 gene is cDNA, genomic DNA or synthesized DNA encoding SRCL-P1;

(14) The transgenic non-human animal according to (13) wherein the expression level is altered by causing the mutation at a gene expression regulatory site;

(15) A knockout mouse wherein a function of mSRCL-P1 gene is deficient;

(16) An antibody to the protein according to (1), (3) or (5), or a fragment thereof;

(17) The antibody according to (16), which is a polyclonal antibody, a monoclonal antibody or a peptide antibody.

(18) A method for the production of a monoclonal antibody to the protein or the fragment thereof according to (1), (3) or (5) which comprises administering the protein or a fragment thereof according to (1), (3) or (5) to a warm-blooded animal other than human, selecting the animal that exhibits an antibody titer, collecting a spleen or a lymph node from the animal, fusing antibody-producing cells contained therein with myeloma cells to prepare a hybridoma that produces a monoclonal antibody;

(19) A method for quantitatively determining an SRCL-P1 protein or a fragment thereof on the basis of an immunological binding between the antibody according to (16) or (17) and the SRCL-P1 protein or a fragment thereof;

(20) A method for detecting an SRCL-P1 protein or a fragment thereof on the basis of an immunological binding between the antibody according to (16) or (17) and the SRCL-P1 protein or a fragment thereof;

(21) An agonist that stimulates an activity of the protein according to (1), (3) or (5);

(22) An antagonist that inhibits an activity or the activation of the protein according to (1), (3) or (5);

(23) A method for screening a drug wherein the protein according to (1), (3) or (5) is used;

(24) A drug which is obtained by the method for the screening according to (23);

(25) A method for screening a drug for the treatment of a pathological state involved in the accumulation of oxidized LDL, which comprises the step of identifying a candidate drug for the treatment of a pathological state involved in the accumulation of oxidized LDL by an inhibitory ability of the candidate drug toward the binding between the protein according to (1), (3) or (5) and oxidized LDL, which is evaluated by comparing the amount of binding between the protein and oxidized LDL in the presence and absence of the candidate drug;

(26) A drug obtained by the method for the screening according to (25);

(27) A method for the treatment of a pathological state involved in the accumulation of oxidized LDL, which comprises the step of inhibiting the binding between an SRCL-P1 protein or a fragment thereof and oxidized LDL using the drug according to (26);

(28) A pharmaceutical composition for the treatment of a pathological state involved in the accumulation of oxidized LDL comprising the drug according to (26);

(29) A method for screening a drug for the treatment of a pathological state involved in the binding of AGE to cells, which comprises the step of identifying a candidate drug for the treatment of a pathological state involved in the binding of AGE to cells by an inhibitory ability of the candidate drug toward the binding between the protein according to (1), (3) or (5) and AGE, which is evaluated by comparing the amount of binding between the protein and AGE in the presence and absence of the candidate drug;

(30) A drug obtained by the method for the screening according to (29);

(31) A method for the treatment of a pathological state involved in the binding of AGE to cells, which comprises the step of inhibiting the binding between an SRCL-P1 protein or a fragment thereof and AGE using the drug according to (30); and

(32) A pharmaceutical composition for the treatment of a pathological state involved in the binding of AGE to cells comprising the drug according to (30);

BRIEF DESCRIPTION OF THE DRAWINGS

FIG. 2 is a drawing illustrating a preceding half of an alignment of amino acid sequences of three kinds of collectins (Human MBP, SEQ Id NO: 29; Human SP-A, SEQ ID NO: 30; and Human SP-D, SEQ ID NO: 31) reported heretofore.

FIG. 3 is a drawing illustrating the latter half of the alignment set forth in FIG. 2 of collectins Human MBP, SEQ ID NO: 29; Human SP-A, SEQ ID NO: 30 and Human SP-D, SEQ ID NO: 31.

FIG. 4(*a*) depicts a drawing showing ORF of the novel collectin obtained.

FIG. 6 is a drawing illustrating a manner how A: oxidized LDL, B: mannose, and C: AGE specifically bind to cells that are expressing hSRCL-P1.

FIG. 8 is a drawing illustrating a manner how hSRCL-P1 is expressed in A: healthy human heart vascular endothelial cells, and B: mouse heart vascular endothelial cells.

BEST EMBODIMENT FOR CARRYING OUT THE INVENTION

Figure 1:
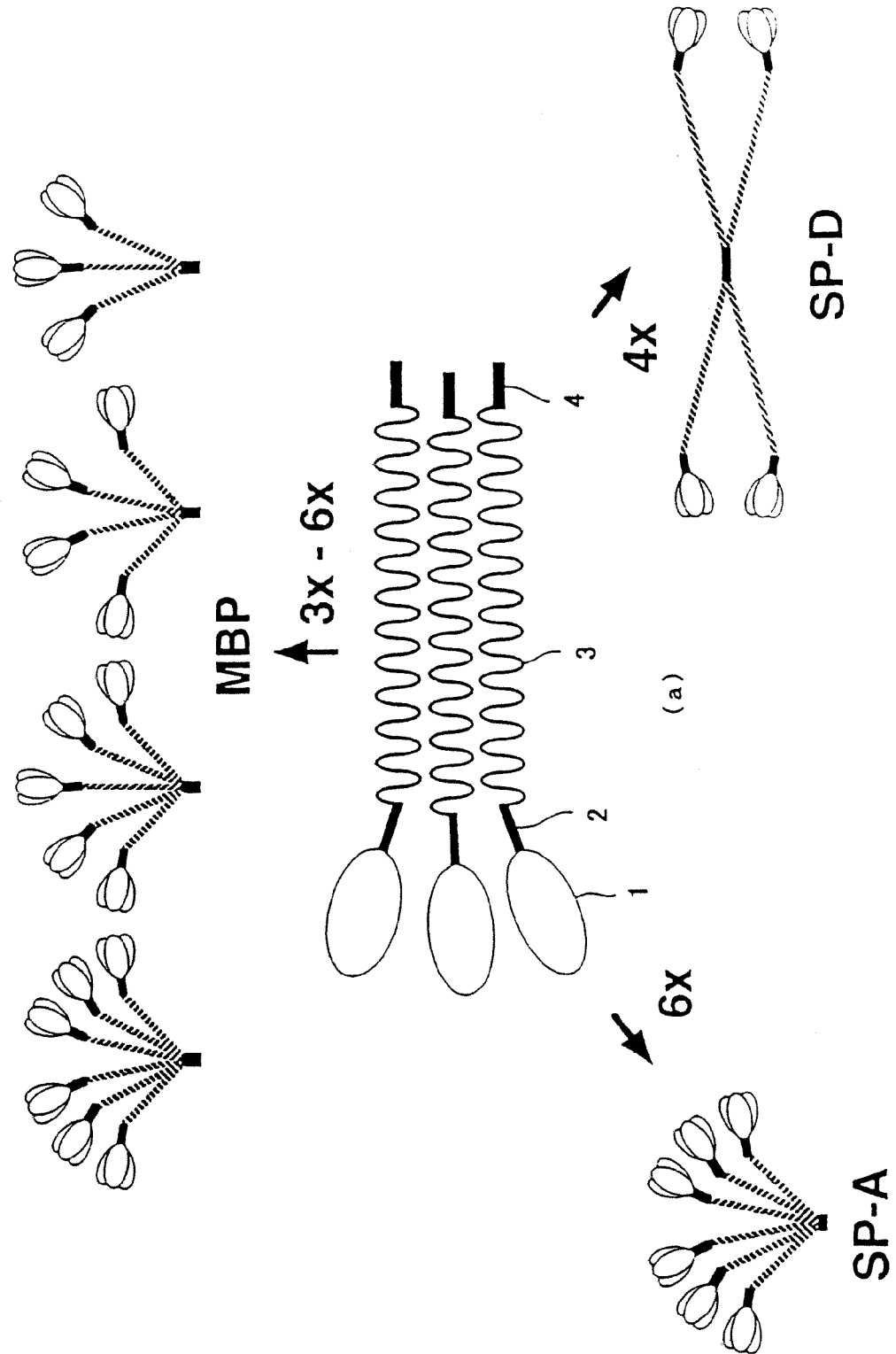
FIG. 1 is a schematic drawing illustrating a basic structure of principal collectins reported heretofore and an overview of the protein.

The present inventors successfully cloned human and mouse novel SR. A collectin domain containing CRD is present at C-terminuses of the novel SR (SRCL-P1), which is believed to participate in basic immunity, and the entire structure of the novel SR was similar to that of SRA, in particular, SR-AI. More specifically, it was constituted at least from a transmembrane domain comprising a leucine zipper that has leucine units repeated four times, an α-helical coiled coil domain, a collagen-like domain, a neck domain, a CRD domain, starting from the N-terminuses. Three molecules having such a characteristic structure are envisaged to form a homotrimer through the formation of an α-helix at the coiled coil domain and the formation of a triple helix at the collagen-like domain. Further, the collagen-like domain is speculated to be positively charged under a condition of physiological pH. In addition, SRCL-P1 protein had numerous carbohydrate chain binding sites The hSRCL-P1 gene and mSRCL-P1 gene used herein include polynucleotides comprising a nucleotide sequence set out in SEQ ID NO: 1 or 3, derivatives thereof (homologues, mutants, modified forms and polymorphic variants), and fragments thereof, unless otherwise stated. Further, the hSRCL-P1 protein and mSRCL-P1 protein used herein comprise amino acid sequence set out in SEQ ID NO: 2 or 4, derivatives thereof and fragments thereof, unless otherwise stated. These may be derived from natural sources, or artificially synthesized. The present invention includes whole of the substances as described above.

Examples of hSRCL-P1 include proteins comprising amino acids set out in SEQ ID NO: 24 (a mutant of the protein set out in SEQ ID NO: 1 with deletion of a part of the collagen-like domain and the neck domain, i.e., amino acid residues of position 483 to 606), and examples of mutants of the polynucleotide set out in SEQ ID NO: 1 include a polynucleotide set out in SEQ ID NO: 23 which encodes the protein set out in SEQ ID NO: 24.

Moreover, the present invention also involves amino acid sequences substantially similar to the amino acid sequence set out in SEQ ID NO: 2 or 4, and nucleotide sequences encoding amino acid sequences substantially similar to the amino acid sequence set out in SEQ ID NO: 2 or 4. Furthermore, proteins comprising these amino acid sequences are also involved. The amino acid sequence substantially similar to the amino acid sequence set out in SEQ ID NO: 2 or 4 refers to the amino acid sequence having alteration such as substitution, deletion, addition and/or insertion of one or several amino acids therein as long as the protein has an equal property to those of the protein comprising an amino acid sequence set out in SEQ ID NO: 2 or 4, that is to say; activity, function and tertiary structure due to the structure which comprises a transmembrane domain containing a leucine zipper structure, and α-helical coiled coil domain and collagen-like domain, which are characteristic in SR. These may be derived from natural sources, or artificially synthesized.

Furthermore, the present invention also involves a nucleotide sequence set out in SEQ ID NO: 1 or 3 or a nucleotide sequence comprising a fragment thereof, or a nucleotide sequence that can hybridize to a nucleotide sequence complementary thereto (hereinafter, referred to as "specified sequence") under a stringent condition. The stringent condition according to the present invention may involve a condition for example; incubating in a solution containing 5×SSC, 5% Denhardt's solution (0.1% BSA, 0.1% Ficoll 400, 0.1% PVP), 0.5% SDS, and 20 µg/ml modified sermon sperm DNA at 37° C. overnight followed by a wash with 2×SSC containing 0.1% SDS at room temperature. SSPE may be employed in place of SSC. Thus resultant nucleotide sequence is speculated to exhibit at least 50% or more homology with the specified sequence. Many of the proteins encoded by the nucleotide sequence that hybridize to the specified sequence under a stringent hybridization condition are believed to have an equal property to SRCL-P1 protein. Therefore, such proteins are also involved in the present invention as long as they have an equal property to SRCL-P1 protein.

In particular, the amino acid sequence of hSRCL-P1 set out in SEQ ID NO: 2 (amino acid position 1 to 742) represents a protein consisting of 742 amino acids, and thus the nucleotide sequence encoding the same consists of 2226 nucleotides. Characteristic amino acid sequences such as those of a leucine zipper domain, an α-helical coiled coil domain, a collagen-like domain, a neck domain, a CRD domain and the like were present in the sequence. That is to say, a leucine zipper domain designated by amino acid position 36-57, an α-helical coiled coil domain designated by amino acid position 72-426 (according to COILS Program) or amino acid position 81-431 (according to MultiCoil Program), a collagen-like domain designated by amino acid position 443-589, a neck domain designated by amino acid position 590-606, a CRD domain designated by 607-742 and the like were present. Other domains include for example, an extracellular domain designated by amino acid position 63-742 (according to TMHMM1.0 program) or amino acid position 58-742 (according to TMpred program), an intracellular domain designated by amino acid position 1-39 (according to TMHMM1.0 program) or amino acid position 1-37 (according to TMpred program), a transmembrane domain designated by amino acid position 40-62 (according to TMHMM1.0 program) or amino acid position 38-57 (according to TMpred program), a collectin-like domain designated by amino acid position 443-742. Moreover, a C type lectin motif designated by amino acid position 708-730 was also included. The nucleotide sequence encoding this protein is set out in SEQ ID NO: 1.

The amino acid sequence of mSRCL-P1 (amino acid sequence 1-742) set out in SEQ ID NO: 4 represents a protein consisting of 742 amino acids, and thus the nucleotide sequence encoding the same consists of 2226 bases. Similarly to hSRCL-P1 set out in SEQ ID NO: 2, characteristic amino acid sequences such as a leucine zipper domain, an α-helical coiled coil domain, a collagen-like domain, a neck domain, a CRD domain, a C type lectin motif and the like were present in the sequence. The nucleotide sequence encoding this protein is set out in SEQ ID NO: 3.

Homologues used herein refer to nucleotide sequences or amino acid sequences that bear high homology, which are homologous at least 50% or more, preferably 70% or more, more preferably 90% or more. When deletion or insertion is present in the sequence, homologous search may be conducted which allows for gap junction. For example, the search may be performed using a procedure of multiple alignment (trade name: SODHO, Fujitsu Limited). In addition, as the algorithm for searching homology, Smith-Waterman algorithm, which is the most accurate, may be employed. Alternatively, FASTA or BLAST may be also utilized via the Internet.

Mutants used herein include for example, those resulting from allele, Single Nucleotide Polymorphism (SNP) and the like. Furthermore, the nucleotide sequence of the present invention may also include the mutated nucleotide sequences derived from the changes in the range of degeneracy of the codon. Partial alteration of the codon of a nucleotide sequence may be achieved according to a routine method using such site directed mutagenesis methods as those in which a primer is employed consisting of a synthesized oligonucleotide that encodes the desired alteration (Mark, D. F. et al., Proc. Natl. Acad. Sci. USA., 81, 5662, 1984). Thus resultant artificial genetic mutants are also involved in the nucleotide sequence of the present invention. Furthermore, the mutated amino acids translated by the mutated codons have preferably similar properties to those of the normal amino acid even in the case where the mutation is beyond the range of degeneracy of the codon. The mutation may preferably be as follows, which are among amino acids having similar properties, functions, characteristics and the like, for example: the mutation among aliphatic amino acids such as alanine, valine, leucine and isoleucine; the mutation among neutral amino acids such as glycine, alanine, serine, threonine, valine, leucine, isoleucine, cysteine, methionine, phenylalanine, tyrosine, proline, tryptophan, asparagines and glutamine; the mutation among acidic amino acids such as aspartic acid and glutamic acid; the mutation among basic amino acids such as arginine, lysine and histidine; the mutation among serine and threonine, having a hydroxyl group; the mutation among phenylalanine and tyrosine, having an aromatic ring; and the like. These artificially or naturally mutated proteins are also included in the protein of the present invention. For the artificial mutation, site-directed mutagenesis may be caused using a PCR method, and alternatively, other known methods may be used to cause mutation at any optional site.

Modified forms used herein may be prepared using conventional techniques, for example, by acetylation, acylation, ADP-ribosylation, amidation, myristoylation, glycosylation, hydroxylation, phosphorylation, sulfation, formylation, methylation, polyethyleneglycolation, lipid coupling, nucleotide coupling, metal coupling (calcium addition and the like), fusion with other protein (albumin and the like), dimerization, and the like. For example, since glycosylation does not occur in *Escherichia coli* as a host, the expression may be conducted in eucaryotic cells when glycosylation is intended. Insect cells may be also used because glycosylation proceeds post-translationally, similarly to in mammalian cells.

Polymorphic variants used herein involve for example, polymorphisms caused by structural or conformational differences in chromosomal DNA, polymorphisms resulting from a change of a gene into its allelic gene, or the like. In general, genes of eucaryotic cells often exhibit polymorphic event, and this event may lead to the substitution of one or more amino acid(s) whilst the activity of the protein may be retained. Therefore, any of the genes encoding a protein obtained by artificially modifying the gene encoding any of the amino acid sequence set out in SEQ ID NO: 2 or 4 is involved in the present invention as far as the protein has a characteristic function of a gene of the present invention. In addition, any of the proteins comprising artificially modified amino acid sequence set out in SEQ ID NO: 2 or 4 is involved in the present invention as far as it has a property of a protein of the present invention. The modification is construed as involving substitution, deletion, addition and/or insertion.

Fragments used herein refer to any optional fragments derived from the amino acid sequence of SRCL-P1 described above, which include for example, an extracellular domain, an intracellular domain, a transmembrane domain, a leucine zipper domain, an α-helical coiled coil domain, a collagen-like domain, a neck domain, a CRD domain, a collectin-like domain, a hydrophobic domain (a neck domain, a transmembrane domain and the like), a hydrophilic domain (domains other than hydrophobic domains), and the like, as well as fragments obtained by the fusion of these fragments. For example, in the amino acid sequence of hSRCL-P1 set out in SEQ ID NO: 2, the fragments included may be: a fragment comprising amino acids of from position 58-63 to position 742 that form a soluble receptor but lacks a transmembrane domain; a fragment comprising amino acids of from position about 1 to 606 that form a transmembrane scavenger receptor but lacks a CRD domain; a fragment comprising amino acids of from position about 36 to position 426-431 that form a soluble scavenger receptor containing a leucine zipper and an α-helical coiled coil domain; and a fragment comprising amino acids of from position 1 to 589 which lacks a CRD domain and a neck domain.

Method for Obtaining SRCL-P1 Gene

A SRCL-P1 gene according to the present invention may be those obtained through any methods. For example, the nucleotide sequence encoding SRCL-P1 of the present invention can be obtained by preparing mRNA from the cells that are expressing the protein, and altering it into a double stranded DNA by a conventional technique. For the preparation of mRNA, guanidine isothiocyanate calcium chloride method (Chirwin, et al., Biochemistry, 18, 5294, 1979) and the like can be employed. For the preparation of poly(A)$^+$ RNA from total RNA, supports bound with oligo(dT), for example, affinity chromatography in which sepharose or latex particles are used, can be employed. Double stranded cDNA can be obtained by using thus obtained RNA described above as a template to treat with reverse transcriptase using oligo(dT) that is complementary to poly(A) chain present at 3'-terminus, or a random primer or a synthesized oligonucleotide corresponding to a part of the amino acid sequence of SRCL-P1 as a primer (Mol. Cell. Biol., 2, 161, 1982; Mol. Cell. Biol., 3, 280, 1983; Gene, 25, 263, 1983); and treating thus resulting cDNA with for example, E. coli RNaseH, E. coli DNA polymerase 1, E. coli DNA ligase to alter into the DNA chain. A cDNA library can be produced by incorporating this cDNA into a plasmid vector, phage vector, cosmid vector to transform E. coli, or by transfecting it into E. coli following in vitro packaging.

The plasmid vector that can be used herein is not particularly limited as long as it can be replicated and maintained in the host. Phage vector is not also particularly limited as long as it can proliferate in the host. Cloning vectors include, for example, pBR322, pUC19, λgt10, λgt11 and the like. Moreover, upon subjecting to immunological screening, the vector has preferably a promoter that enables the expression of an SRCL-P1 gene in the host.

To incorporate cDNA into a plasmid, the method of Maniatis et al. (Molecular Cloning, A Laboratory Manual, second edition) and the like can serve as a reference. Further, to incorporate cDNA into a phage vector, the method disclosed in Hyunh et al. (DNA cloning, a practical approach, 1, 49, 1985) and the like can serve as a reference.

As the method for introducing the expression vector described above into host cells, methods for example, transfection by lipopolyamine method, DEAE-dextran method, Hanahan method, lipofectin method, calcium phosphate method; microinjection, and electroporation (Molecular Cloning, A Laboratory Manual, second edition) and the like may be involved. In vitro packaging can be readily effected by using commercially available kits (manufactured by Stratagene, or Amersham).

The method for the isolation of cDNA encoding SRCL-P1 protein from a cDNA library prepared as described above may involve a general method, which may be used in combination, for the screening of cDNA. For example, a probe labeled with $^{32}P$ is produced, and a clone containing the desired cDNA can be screened by a colony hybridization method (Proc. Natl. Acad. Sci. USA, 72, 3961, 1975), or a plaque hybridization method (Molecular Cloning, A Laboratory Manual, second edition, Cold Spring Harbor Laboratory, 2, 108, 1989). Further, a clone may be selected by a PCR method. Additionally, the desired clone can be selected through use of an antibody that recognizes SRCL-P1 when a cDNA library is produced using a vector that can express cDNA.

Furthermore, when an SRCL-P1 gene is isolated from cells that express SRCL-P1 gene, for example, the expressing cells are dissolved using SDS or proteinase K, followed by a phenol treatment. Unwanted RNA is digested with ribonuclease. Thus resultant DNA is digested with restriction enzyme, and the resulting DNA fragments are amplified using phage or cosmid to produce a library. Thereafter, the desired clone is selected, and then an SRCL-P1 gene can be obtained.

The nucleotide sequence of the DNA obtained accordingly can be determined by a Maxam-Gilbert method (Proc. Natl. Acad. Sci. USA, 74, 560, 1977) or a Sanger's method (Proc. Natl. Acad. Sci. USA, 74, 5463, 1977). The SRCL-P1 gene can be obtained by excising from the clone as obtained above.

Through use of the primer synthesized on the basis of the nucleotide sequence of SRCL-P1, cloning can be also effected by a RT-PCR method using poly(A)$^+$ RNA of the cells expressing SRCL-P1 as a template. Further, the desired cDNA can be also obtained by directly screening the cDNA library after producing/synthesizing a probe based on the nucleotide sequence of SECL-P1, not by way of the PCR. The gene of the present invention can be selected among the genes obtained by the methods described above through the verification of the nucleotide sequence of the gene. The gene of the present invention can be also produced according to the conventional method in which chemical synthesis of a nucleic acid, e.g., phosphoimidite method (Mattencci, M. D. et al., J. Am. Chem. Soc., 130, 3185, 1981) or the like, is employed.

Method for Producing Expression Vector

The present invention also relates to a vector comprising a nucleotide sequence of SRCL-P1s. The vector is not particularly limited so far as it can express the SRCL-P1s protein, for example, a plasmid vector, an RNA vector, a DNA vector, a virus vector, a phage vector and the like may be employed. Specifically, examples thereof include pBAD/H is, pRSETA, pcDNA2.1, pTrcHis2A, pYES2, pBlueBac4.5, pcDNA3.1 or pSecTag2 manufactured by Invitrogen, pET or pBAC manufactured by Novagen Co., pGEM manufactured by Promega, pBluescriptII, pBS, Phagescript, pSG or pSV2CAT manufactured by Stratagene, or pGEX, pUC18/19, pBPV, pSVK3 or pSVL manufactured by Pharmacia Co.

The cDNA sequence of SRCL-P1s ligated to the expression vector is operatively linked to a promoter. The promoter includes for example, phage λPL promoter, E. coli lac, trp, tac promoter, SV40 early and late promoter, T7 and T3 promoter, retrovirus LTR promoter. Specifically, the prompter for use in eukaryotic cells include CMV promoter, HSV promoter, SV40 early and late promoter, retrovirus LTR promoter, RSV promoter, metallothionein promoter. In addition, the expression vector may contain a marker to allow the selection of the transformed host, and an enhancer. Examples of the marker include dihydrofolate reductase gene, neomycin resistant gene, ampicillin resistant gene and the like. Examples of the enhancer include SV40 enhancer, cytomegalovirus early enhancer promoter, adenovirus enhancer and the like.

Method for Producing Transformed Cells

The present invention further provides transformed cells carrying a nucleotide sequence of the present invention to allow the expression thereof by means of the vector as described above carrying the nucleotide sequence. The host cell for use as a transformed cell in the present invention may preferably include animal cells and insect cells, however, included may be any of the cells (microorganisms may be also included), which can express SRCL-P1s protein in the expression vector of the present invention.

Exemplary animal cells and insect cells of the present invention may respectively include cells derived from human, or cells derived from fly or silkworm (*Bombyx mor*). For example, CHO cells, COS cells, BHK cells, Vero cells, myeloma cells, HEK293 cells, HeLa cells, Jurkat cells, mouse L cells, mouse C127 cells, mouse FM3A cells, mouse fibroblast, osteoblast, chondrocyte, S2, Sf9, Sf21, High Five™ cells may be included. The microorganism according to the present invention include *Escherichia coli, Saccharomyces cerevisiae* and the like. For the introduction of a vector into such hosts, the method as described above may be employed.

In regard to SR pathway involved in the onset of arteriosclerosis and the like, SR-expressing cells of the present invention can be used for analyzing the specificity of modified LDLs that are incorporated into cells from this pathway. In addition, they are useful as models for the analysis of incorporation of substances into the cells via a receptor. Moreover, the cells of the present invention can be used for screening drugs in the process of developing therapeutic drugs of arteriosclerosis, for example, depressants of LDL modification, inhibitors of acyl Co-A cholesterol acyltransferase (ACAT) activity, and the like. Furthermore, they can be used for the manufacture of human SR protein having a carbohydrate chain. They may be also employed in experimental systems for the process of treating foreign substances or denaturated substances via SR, or in systems for investigating infection of B type viruses that cause infection concomitant with a modified albumin.

Method for Obtaining Protein

The present invention also relates to a method for the production of SRCL-P1 which comprises culturing a cell transformed with the nucleotide sequence of the present invention as set forth above, and harvesting thus produced SRCL-P1. Cell culture, isolation of the protein, and purification may be carried out with conventionally known methods.

The protein of the present invention can be expressed as a recombinant fusion protein, which can be readily isolated, purified, and recognized per se. The recombinant fusion protein is a protein expressed by adding an appropriate peptide chain to the N-terminal end and/or C-terminal end of a protein expressed from a nucleotide sequence encoding the desired protein. In order to facilitate the purification of the expressed protein, the protein may be expressed as a fusion protein having a signal for extracellular secretion. In addition, the protein can be obtained from several kinds of sources such as cultured cells, cultured tissues, transformed cells and the like using conventionally known methods, for example, known purification methods including: salting out such as ammonium sulfate precipitation technique and the like; gel filtration technique such as Sephadex and the like; ion exchange chromatographic technique; hydrophobic chromatographic technique; dye gel chromatographic technique; electrophoresis technique; dialysis; ultrafiltration technique; affinity chromatographic technique; high performance liquid chromatographic technique; and the like.

Method of the Utilization of Gene

Probes for detecting SRCL-P1 gene can be specified on the basis of the nucleotide sequence set out in either SEQ ID NO: 1 or 3. Alternatively, primers can be specified for the amplification of DNA or RNA including such a nucleotide sequence. To specify a probe or a primer based on a given sequence is ordinarily carried out by those skilled in this art. An oligonucleotide having a specified nucleotide sequence can be obtained through chemical synthesis. When a suitable label is added to the oligonucleotide, it can be utilized for hybridization assay in several formats. Alternatively, it can be also utilized in reactions for synthesis of nucleic acids such as PCR. The oligonucleotide that is utilized as a primer is of at least 10 bases in length, and preferably of 15 to 50 bases in length. It is desirable that the oligonucleotide used as a probe be of from 100 bases to its full length. Further, such oligonucleotides can be also used for the diagnosis of diseases caused by mutation of an SRCL-P1 gene because they can be used for detecting genetic mutation encoding SRCL-P1 protein and for detecting SNP. They are expected to be available for the diagnosis of a variety of diseases including for example, arteriosclerosis, diabetic complications and Alzheimer's disease, hyper β-lipoproteinemia, hypercholesterolemia, hypertriglyceridemia, hypo α-lipoproteinemia, transplantation, atherectomy, post angiogenic restenosis, bacterial infections, and the like. In addition, they are also useful for gene therapy whereby SRCL-P1 gene is introduced into a living body to allow the expression thereof.

Moreover, it is also possible to obtain a promoter region and an enhancer region of the SRCL-P1 gene that is present in a genome, based on a cDNA nucleotide sequence of SRCL-P1 provided by the present invention. In particular, these control regions can be obtained by similar methods to those disclosed in Japanese unexamined patent publication No. 6-181767; J. Immunol., 155, 2477, 1995; Proc. Natl. Acad. Sci, USA., 92, 3561, 1995, and the like. Promoter region referred to herein means a DNA region which controls the expression of a gene that exists upstream of a transcription initiation site. Enhancer region herein means a DNA region that enhances the expression of a gene that exists in an intron, a 5'-untranslated region, or a 3'-untranslated region.

Method of the Utilization of Protein

SRCL-P1s proteins of the present invention can be utilized in the elucidation of functions of macrophage and fundamental immunity, the elucidation of mechanisms of development of various types of diseases including for example, arteriosclerosis, diabetic complications and Alzheimer's disease, hyper β-lipoproteinemia, hypercholesterolemia, hypertriglyceridemia, hypo α-lipoproteinemia, transplantation, atherectomy, post angiogenic restenosis and the like, as well as diagnostic, prophylactic, therapeutic methods thereof, and in the development of reagents and drugs for the same. Furthermore, they can be used as an antigen for producing antibodies to SRCL-P1s. Additionally, they can be utilized in the screening method of agonists or antagonists.

Agonist and Antagonist

The present invention also relates to agonists which stimulate the activity or the activation of SRCL-P1 of the present invention. In addition, the present invention also relates to antagonists which inhibit the activity or the activation of SRCL-P1 of the present invention. For screening the antagonist, a competitive experimental system can be used, for example, in which OxLDL or an antibody, and a candidate inhibitor are subjected to the interaction with cells expressing SRCL-P1 protein thereby allowing the candidate inhibitor to screen based on the binding ratio of OxLDL. Otherwise, conventionally known methods may also be carried out to effect the screening. Further, the antagonists also include antisense nucleic acids that inhibit the expression of SRCL-P1 gene. Included in the examples of the other methods for the screening may be methods in which a change in extracellular pH is measured, which is caused by the activation of a receptor (Science, 246, 181-296, 1989).

The antagonist thus screened can be also utilized as a drug for the treatment, which may include therapy, prophylaxis and the like, of pathological states involving in the accumulation of oxidized LDL, or in the binding of AGE to cells. The screening method comprises the steps of comparing the amount of binding between SRCL-P1 of the present invention, and oxidized LDL or AGE in the presence and absence of a candidate drug; and identifying the candidate drug for treating the intended pathological state by an inhibitory ability of the candidate drug to the binding therebetween.

Transgenic Non-Human Animal

The present invention relates to transgenic non-human animals having an altered expression level of SRCL-P1 gene. SRCL-P1 gene herein includes cDNA, genomic DNA or synthesized DNA encoding hSRCL-P14 or SRCL-P1. For expression of a gene, any one of the steps of transcription and translation should be comprised. The transgenic non-human animals according to the present invention are useful for the investigation of functions or expression mechanisms of SRCL-P1, elucidation of mechanisms of diseases that are anticipated to be involved in SRCL-P1, development of diseased animal models for use in screening and safety tests of pharmaceutical products.

In the present invention, the gene can be artificially modified to increase or decrease the expression level in comparison with the native expression level of the gene by introducing mutation such as deletion, substitution, addition and/or insertion into a part of some key sites (enhancer, promoter, intron and the like) that regulate the expression of the gene to be proper. The introduction of the mutation can be carried out by known methods to obtain a transgenic animal.

Transgenic animals in their narrow means refer to animals having germ cells into which a foreign gene was artificially introduced by a genetic recombination technique. In their broader means, they include: antisense transgenic animals having a particular gene of which function was suppressed using an antisense RNA; knockout animals having a particular gene knocked out using embryonic stem cells (ES cell); and animals having point mutation of DNA introduced, all of which are animals having a chromosome with a foreign gene being stably introduced at an early stage of the development of the individual, and having a genotype that can be transmitted to the progeny thereof.

Transgenic animals referred to herein should be comprehended in their broader means including all vertebrates other than human. The transgenic animals according to the present invention are useful for the investigation of functions or expression mechanisms of SRCL-P1, elucidation of mechanisms of diseases that are involved in cells expressed in human, development of diseased animal models for use in screening and safety tests of pharmaceutical products.

Method for producing a transgenic mouse may include: a method in which a gene is directly injected into a nucleus of an ovum in a anterior nucleus phase with a micropipette under a phase contrast microscope (microinjection technique, U.S. Pat. No. 4,873,191); a method in which embryonic stem cells (ES cells) are used. Alternatively, a method in which a gene is introduced into a retrovirus vector or an adenovirus vector followed by infection into an ovum; a sperm vector technique in which a gene is introduced into an ovum via a sperm; and the like have been developed.

The sperm vector technique is a genetic recombinant method in which a foreign gene is attached to a sperm, or a foreign gene is introduced into a sperm cell with an electroporation technique, and then the foreign gene is introduced into an ovum by fertilizing the ovum (M. Lavitranoet et al., Cell, 57, 717, 1989). Alternatively, site directed genetic recombination in vivo may be also employed by a cre/locP recombinase system of bacteriophage P1, a FLP recombinase system of *Saccharomyces cerevisiae*, or the like. Additionally, a method has been also reported in which a transgene of a desired protein is introduced into a non-human animal using retrovirus.

Method for the production of a transgenic animal with a microinjection technique is carried out as described below, for example.

First, a transgene is required, which is substantially constituted from a promoter involved in expression control, a gene encoding a specified protein, and a poly(A) signal. The manner of the expression and/or the expression level of a specified molecule may be affected by the promoter activity. In addition, because transgenic animals are different among the produced lineages in respect to the number of the copies of the introduced transgene, or the introduced site in the chromosome, the manner of the expression and/or the expression level must be confirmed for each of the lineages. Since it has been elucidated that the expression level is altered depending on the untranslated region or splicing, an intron sequence to be spliced at a preceding site of poly (A) signal may be previously introduced. It is important to use a gene, which is introduced into a fertilized ovum, has as high purity as possible. The animal to be used may include mice for use in collecting fertilized ova (5-6 weeks old), male mice for use in mating, female pseudopregnant mice, vas deferens ligated male mice, and the like.

In order to efficiently obtain the fertilized ova, gonadotropin or the like may be used for inducing the ovulation. The fertilized ova are harvested, and thereafter, a gene in an injection pipette is introduced into a male pronucleus of the ovum by a microinjection technique. An animal (a pseudopregnant mouse or the like) for use in repositioning the injected ova to an oviduct is provided, to which 10-15 ova are transplanted per one animal. Thereafter, the born mouse can be examined for the introduction of the transgene by: extracting genomic DNA from the end portion of the tail; and detecting the transgene by a Southern method or a PCR technique, alternatively by a positive cloning technique where a marker gene is inserted which is activated upon only the occurrence of homologous recombination. Moreover, in order to ascertain the expression of the transgene, a transcription product derived from the transgene is detected by a Northern method or a RT-PCR technique. Alternatively, a western blotting method may be carried out with a specific antibody to the protein or a fragment thereof.

Knockout Mouse

The knockout mouse according to the present invention is one that was treated in a manner to deprive the function of SRCL-P1 gene. Knockout mouse refers to a transgenic mouse in which an arbitrary gene is destroyed by a homologous recombination technique to impair the corresponding function. The knockout mouse can be produced by homologous recombination using ES cells, followed by the selection of the embryonic stem cell having one of the allelic gene altered/destroyed. A chimeric mouse, which carry cells derived from the embryonic stem cells and cells derived from the embryo being mixed, may be obtained by, for example, injecting the embryonic stem cell that had been genetically engineered at blastocyst stage or morulae stage of the fertilized ovum. When this chimeric mouse (chimera refers to a single individual built-up with somatic cells on the basis of more than two fertilized ova) is crossbred with a normal mouse, a heterozygotic mouse can be produced having one of the allelic gene is entirely altered/destroyed. Further, a homozygotic mouse can be produced by crossbreeding heterozygotic mice each other.

Homologous recombination refers to the recombination that is caused by a mechanism of genetic recombination between two genes having identical or extremely similar nucleotide sequences. For the selection of cells with the homologous recombination, PCR can be employed. PCR reaction, in which primers corresponding to a part of the inserted gene and a part of the region expected to be inserted are used, may be carried out to reveal the homologous recombination occurring in cells that could yield the amplification products. Also, when the homologous recombination is caused to a gene expressed in embryonic stem cells, the gene to be introduced may be joined to a neomycin resistant gene to allow the selection after the introduction into cells by making them resistant to neomycin. Accordingly, known methods and the modified methods thereof can be employed to enable the easy selection.

Method for Producing Antibodies

The present invention further provides antibodies that recognize SRCL-P1 or fragments thereof. The antibodies in accordance with the present invention include for example, the antibodies to a protein comprising an amino acid sequence set out in SEQ ID NO: 2 or 4, or a fragment thereof. The antibodies (e.g., polyclonal antibodies, monoclonal antibodies, peptide antibodies) or antisera to SRCL-P1 or a fragment thereof can be produced using SRCL-P1 or a fragment thereof of the present invention as an antigen according to any method for producing the antibodies or antisera which is known per se. In particular, the antibodies that can control the function of SRCL-P1 (e.g., antibodies that recognize CRD, a collagen like domain and an α-helical coiled coil domain or the like) are useful for pharmaceutical products containing the antibody.

SRCL-P1 or a fragment thereof according to the present invention may be administered neat or with a diluent or a carrier to a warm-blooded animal at a site that enables the production of the antibody upon the administration. In order to facilitate the production of antibodies upon the administration, complete Freund's adjuvant or incomplete Freund's adjuvant may be administered. The administration may be usually conducted once per 1 to 6 weeks, and two to ten times in total. The warm-blooded animal used may include for example, monkey, rabbit, dog, guinea pig, mouse, rat, sheep, goat, chicken, and the like. Among these, mouse and rat may be preferably used. Rat that may be preferably used includes Wistar and SD strain rat, and mouse that may be preferably used includes BALB/c, C57BL/6 and ICR strain mouse and the like.

Upon the production of cells that produce a monoclonal antibody, an individual with the antibody titer that can be recognized therein is selected from the warm-blooded animals e.g., mice that had been immunized with an antigen. On two to five days after final immunization, spleen or lymph node is collected, and the antibody producing cells contained therein are subjected to the fusion with myeloma cells to effect the preparation of monoclonal antibodies producing cells. The determination of the antibody titer in the antiserum may be carried out for example, by subjecting a labeled SRCL-P1 described below to a reaction with the antiserum, and measuring the activity of the label bound to the antibody. The fusion operation can be performed in accordance with a known technique for example, the method of Köhler and Milstein (Nature, 256, 495, 1975) and the modified method thereof (J. Immunol. Method, 39, 285, 1980; Eur. J. Biochem., 118, 437, 1981; Nature, 285, 446, 1980). Examples of the fusion accelerating agent may include polyethylene glycol (PEG), Sendai virus and the like, and polyethylene glycol may be preferably used. In addition, lectin, poly-L-lysine or DMSO may be added ad libitum to raise the efficiency of the fusion.

Examples of the myeloma cell include X-63Ag8, NS-1, P3U1, SP2/0, AP-1 and the like, and SP2/0 may be preferably used. The ratio of antibody producing cell (spleen cell) number to myeloma cell number preferably used is 1:20-20:1. PEG (preferably, PEG1000-PEG6000) is added at approximately 10-80%. The fusion mixture is incubated at 20-40° C., preferably at 30-37° C. for 1-10 min. Such a condition enables efficient cell fusion. Screening of the hybridoma that produces anti-SRCL-P1 antibody may be performed by using various methods, which include for example, a method in which a supernatant of hybridoma culture is added to a solid phase (e.g., a microplate) absorbed with SRCL-P1 antigen directly or with a carrier, and then an anti-immunoglobulin antibody (when the cell used for the cell fusion was derived from a mouse, anti-mouse immunoglobulin antibody may be used) that was labeled with a radioactive substance, enzyme or the like, or protein A is added thereto thereby detecting the anti-SRCL-P1 antibody bound to the solid phase; or a method in which a supernatant of hybridoma culture is added to a solid phase absorbed with anti-immunoglobulin antibody or protein A, and then SRCL-P1 labeled with a radioactive substance, enzyme or the like is added thereto thereby detecting the anti-SRCL-P1 monoclonal antibody bound to the solid phase.

Selection and cloning of the anti-SRCL-P1 antibody can be carried out by known methods per se, or the modified methods thereof. Usually, the method is carried out in a medium for animal cells added with HAT (hypoxanthine, aminopterin, thymidine). The medium for use in the selection, cloning and growing may be any one of the media in which hybridoma can grow. For example, RPMI medium containing 1-20%, preferably 10-20% of fetal bovine serum, GIT medium containing 1-10% of fetal bovine serum, or serum free medium for hybridoma culture, and the like. The temperature of the culture may be preferably about 37° C. The culture period may be usually five days to three weeks, preferably one week to two weeks. The culture is usually conducted in the presence of 5% carbon dioxide gas. The antibody titer of the supernatant of the hybridoma culture can be measured in a similar manner to the measurement of the antibody titer of anti-SRCL-P1 antibody in an antiserum as described above. In other words, a radioimmunoassay (RIA) technique, an enzyme linked immunosorbent assay (ELISA) technique, a FIA (fluorescent immunoassay) technique, a plaque measurement technique, an agglutination reaction technique and the like may be employed as the measurement method, however, the ELISA technique as described below is preferred.

The screening by an ELISA technique can be carried out in accordance with the following procedure. A protein, which was prepared by a similar method to that for the immunoantigen, is immobilized on the surface of each well of an ELISA plate. Next, BSA, MSA, OVA, KLH, gelatin or skimmed milk or the like is immobilized for the purpose of preventing nonspecific adsorption. To each well of this plate added with a supernatant solution of the hybridoma culture, followed by allowing the immunoreaction by standing for a predetermined time. Each well is washed using a washing solution such as PBS or the like. Surfactant may be preferably added to this washing solution. An enzyme-labeled secondary antibody is added, and the mixture is allowed to stand for a predetermined time. The enzyme for labeling which can be used includes β-galactosidase, alkaline phosphatase, peroxidase and the like. After the washes with the same washing solution, enzyme reaction is effected through adding a substrate solution of the labeled enzyme that was employed. When the desired antibody is present in the added supernatant solution of the hybridoma culture, the enzyme reaction proceeds to change the color of the substrate solution.

Cloning can be usually carried out by known methods per se, such as a semisolid agar technique, a limiting dilution technique or the like. Specifically, after the well in which the desired antibody is produced is confirmed by the method described above, a single clone is obtained through conducting the cloning. The method for cloning may involve a limiting dilution technique or the like, in which hybridoma cells are diluted so that one colony per one well of a culture plate is formed, and thereafter the culture is conducted. Cloning by a limiting dilution technique may be performed through the use of feeder cells in order to elevate the colony formation ability, otherwise, a cell growth factor such as interleukin 6 may be added thereto. Alternatively, FACS and single cell manipulation techniques can be employed for the cloning. The cloned hybridoma is cultured preferably in a serum free medium, and an appropriate amount of the antibody is added to the supernatant thereof. Thus resulting single hybridoma may be subjected to a large scale culture using a flask or a cell culture equipment, or may be cultured in the peritoneal cavity of an animal (J. Immunol. Meth., 53, 313, 1982) to give a monoclonal antibody. When the culture is conducted in a flask, a medium for cell culture (IMDM, DMEM, RPMI 1640, MEM and the like) containing 0-20% of FCS can be used. When the culture is conducted in the peritoneal cavity of an animal, an animal of the same species, and the same strain as the animal from which myeloma cells derived that were used for the cell fusion; otherwise an athymic nude mouse may be preferably used. Hybridoma is transplanted after mineral oil such as pristine or the like is previously administered to the animal. Ascites containing the monoclonal antibody can be obtained after one to two weeks passed, when the myeloma cells enough proliferate.

The monoclonal antibody of the present invention can be obtained as the antibody, which does not cross-react with other proteins, by selecting one which recognizes an epitope specific for SRCL-P1. In general, an epitope, which is presented by serial amino acid residues of at least more that or equal to five, preferably 7 to 20 amino acids among the amino acid sequence constituting the protein, is referred to as an epitope inherent in the protein. Therefore, the monoclonal antibody that recognizes an epitope constituted from a peptide having an amino acid sequence, which were selected from the amino acid set out in any of SEQ ID NO: 2 and 4, consisting of at least five serial amino acid residues may be identified as the monoclonal antibody specific to hSRCL-P1 or mSRCL-P1 according to the present invention. When an amino acid sequence is conserved among the amino acid sequence set out in SEQ ID NO: 2 and 4, an epitope common to SRCL-P1 can be selected. Alternatively, a monoclonal antibody can be selected which enables the discrimination of each protein, with a region including an amino acid sequence specific for each of the sequences.

The separation and purification of anti-SRCL-P1 monoclonal antibody can be carried out according to the separation and purification method of an immunoglobulin similarly to the usual separation and purification method of the polyclonal antibodies. Known purification method which can be adopted may include for example, a salt precipitation technique, an alcohol precipitation technique, an isoelectric point precipitation technique, an electrophoretic technique, an ammonium sulfate precipitation technique, an adsorption/desorption technique by an ion exchanger (e.g., DEAE), an ultracentrifugation technique, a gel filtration technique, and a specific purification technique in which an antibody alone is collected by an antigen-bound solid phase or an active adsorbent such as protein A or protein G, or the like, followed by dissociation of the binding to give the antibody. For the purpose of preventing the formation of aggregates, or the decrease in the antibody titer in the purification step, for example, human serum albumin may be added at a concentration of 0.05-2%. Otherwise, amino acids such as glycine, α-alanine and the like, in particular, basic amino acid such as lysine, arginine, histidine and the like, saccharides such as glucose, mannitol and the like, salts such as sodium chloride may be also added. In the case of IgM, which is known to be liable to agglutinate, it may be treated with β-propionolactone and acetic anhydride.

The polyclonal antibody according to the present invention can be produced by known methods per se, or the modified methods thereof. For example, to produce a polyclonal antibody, an immunoantigen (a protein antigen) itself or a complex, which was formed with the immunoantigen and a carrier protein, is used for the immunization of a warm-blooded animal in a similar manner to the method for producing the monoclonal antibody described above, followed by collecting the preparation containing the antibody to the protein of the present invention or a fragment thereof from the warm-blooded animal, and then the antibody is purified/isolated. In respect to the complex of an immunoantigen and a carrier protein for use in the immunization of the warm-blooded animal, the kind of the carrier protein and the mixing ratio of the carrier and hapten may be optionally determined as long as the antibody can be efficiently produced to the hapten subjected to the immunization after crosslinking with the carrier. Thus, any kind of the carrier protein may be crosslinked at any ratio, however, the method in which about 0.1-20, preferably about 1-5 of bovine serum albumin, bovine thyroglobulin, hemocyanin or the like, for example, is coupled with 1 of hapten by weight may be used. In addition, various condensing agents may be used for the coupling of the hapten and carrier, which may include glutaraldehyde and carbodiimide, and active ester reagents containing maleimide active ester, thiol group, dithiopyridyl group and the like. The condensation product is administered neat or with a carrier or a diluent to a warm-blooded animal at a site that enables the production of the antibody upon the administration. In order to facilitate the production of antibodies upon the administration, complete Freund's adjuvant or incomplete Freund's adjuvant may be administered. The administration may be usually conducted once per 2 to 6 weeks, and three to ten times in total. Polyclonal antibodies can be collected from the blood, ascites and the like, and preferably from the blood, of the warm-blooded animal immunized by a method as described above. The measurement of the antibody titer in antiserum can be carried out in a similar manner to the measurement of the antibody titer of the antiserum as described above. The separation and purification of the polyclonal antibody can be carried out according to the separation and purification method of an immunoglobulin similarly to the separation and purification method of a monoclonal antibody described above.

Method of the Utilization of Antibody

Monoclonal antibodies and polyclonal antibodies to SRCL-P1 or a fragment thereof can be utilized in diagnosis and therapy of the diseases relating to the cells that are expressing SRCL-P1. SRCL-P1 or a fragment thereof can be measured using these antibodies, on the basis of the immunological binding with SRCL-P1 or the fragment thereof according to the present invention. Specifically, the method for measuring SRCL-P1 or a fragment thereof using such an antibody may include for example, sandwich techniques in which a sandwich complex is detected which was produced by subjecting SRCL-P1 or a fragment thereof to a reaction with an antibody coupled to an insoluble support and a labeled antibody; or competitive techniques in which SRCL-P1 or a fragment thereof in a sample is measured by subjecting labeled SRCL-P1, and SRCL-P1 or a fragment thereof in a sample to a competitive reaction with the antibody followed by the measurement of SRCL-P1 or a fragment thereof in a sample from the amount of the labeled antigen that reacted with the antibody.

Upon the measurement of SRCL-P1 or a fragment thereof by the sandwich technique, two-step methods in which SRCL-P1 or a fragment thereof is first subjected to a reaction with an immobilized antibody; thereafter, unreacted materials are completely removed by washes; and then a labeled antibody is added thereto to have the immobilized antibody—SRCL-P1 labeled antibody formed, alternatively, one-step methods in which an immobilized antibody, a labeled antibody and SRCL-P1 or a fragment thereof are mixed concurrently.

Insoluble support for use in the measurement include for example, synthetic resin such as polystyrene, polyethylene, polypropylene, polyvinyl chloride, polyester, polyacrylic acid ester, nylon, polyacetal, fluorine-contained resin and the like; polysaccharides such as cellulose, agarose and the like; glasses; metals; and the like. The insoluble support may be in a variety of forms, and for example, tray-like, spherical, fibrous, cylindrical, discal, vessel-like, cell-like, tubular, and the like may be adopted. The support onto which the antibody had been adsorbed may be stored in cold, if necessary, in the presence of an antiseptic agent such as sodium azide and the like.

For the immobilization of the antibody, known chemical coupling methods or physical adsorption methods may be adopted. Chemical coupling method includes for example, methods in which glutaraldehyde is used; maleimide methods in which N-succinimidyl-4-(N-maleimidemethyl) cyclohexane-1-carboxylate and N-succinimidyl-2-maleimide acetate and the like are used; carbodiimide methods in which 1-ethyl-3-(3-dimethylaminopropyl) carbodiimide hydrochloride and the like is used. Other method includes maleimidobenzoyl-N-hydroxysuccinimide ester methods, N-succimidyl-3-(2-pyridylthio)propionic acid methods, bisdiazobenzidine methods, dipalmityl lysine methods. Alternatively, a complex that had been formed previously by subjecting the substance to be detected to a reaction with two kinds of antibodies of which epitopes are different can be captured by the third antibody to the antibody, which had been immobilized in a similar manner to those described above.

The material to be used for labeling may include enzyme, fluorescent materials, luminescence materials, radioactive materials, metal chelates and the like. Examples of enzyme may include peroxidase, alkaline phosphatase, β-D-galactosidase, malate dehydrogenase, staphylococcus nuclease, delta-5-steroid isomerase, α-glycerolphosphate dehydrogenase, triose phosphate isomerase, horseradish peroxidase, asparaginase, glucose oxidase, ribonuclease, urease, catalase, glucose-6-phosphate dehydrogenase, glucoamylase, acetylcholine esterase and the like. Fluorescent materials may include for example, fluorescein isothiocyanate, phycobilin protein, rhodamine, phycoerythrin, phycocyanin, allophycocyanin, orthophthalic aldehyde and the like. Luminescence materials may include isoluminol, lucigenin, luminol, aromatic acridinium esters, imidazole, acridinium salts and modified esters thereof, luciferin, luciferase, aequorin and the like. Radioactive materials may include $^{125}I$, $^{127}I$, $^{131}I$, $^{14}C$, $^{3}H$, $^{32}P$, $^{35}S$ and the like. These materials are not limited thereto as long as the material can be used in immunological determination methods. In addition, low molecular weight hapten such as biotin, dinitrophenyl, pyridoxal or fluorescamine may be conjugated to the antibody. Preferably, horseradish peroxidase may be used as a labeling enzyme. This enzyme can react with many kinds of substrates, which can be readily conjugated to the antibody by a periodic acid method.

When an enzyme is used as a labeling agent, a substrate for measuring its activity, and a color-developing agent as needed may be employed. When peroxidase is used as an enzyme, $H_2O_2$ may be used as a substrate solution, and 2,2'-azino-di-[3-ethylbenzthiazolin sulfonate]ammonium (ABTS), 5-aminosalicylic acid, orthophenylenediamine, 4-aminoantipyrine, 3,3',5,5'-tetramethylbenzidine or the like may be used as a color-developing agent. When alkaline phosphatase is employed as an enzyme, orthophenylphosphate, paranitrophenylphosphate or the like may be used as a substrate. Alternatively, when β-D-galactosidase is used as an enzyme, fluorescein-di-(β-D-galactopyranoside), 4-methyl-umbelliferyl-D-galactopyranoside, or the like may be used as a substrate. The present invention also involves kit products including a monoclonal antibody, a polyclonal body described above, and reagents.

Available crosslinking agents include N,N'-orthophenylenedimaleimide, 4-(N-maleimidemethyl) cyclohexanoyl N-succinimide ester, 6-maleimidehexanoyl N-succinimide ester, 4,4'-dithiopyridine, and other known crosslinking agents. The reaction of such a crosslinking agent with the enzyme and the antibody may be conducted in accordance with known methods depending upon the properties of the respective crosslinking agents. Additionally, the antibodies to be used may be any fragments of the antibodies for example, Fab', Fab, F(ab')$_2$ depending on the condition. Furthermore, enzymatically labeled antibodies may be prepared by using a similar method to any one of those for polyclonal antibodies and monoclonal antibodies. When the enzymatically labeled antibody that was obtained by using the aforementioned crosslinking agent is purified by any known methods such as affinity chromatography or the like, more sensitive immunological determination system can be achieved. The enzymatically labeled antibody, which was purified in such a manner, is stored in a cold and dark place after adding thimerosal, glycerol or the like as a stabilizer, alternatively, after being lyophilized.

The subject sample for the measurement may be a sample containing SRCL-P1, which may include body fluids such as plasma, serum, blood, urine, tissue fluid, cerebrospinal fluid and the like, various types of cells, tissues, and the like.

Method for Producing Humanized Antibody

It is ethically impermissible to produce antibodies by immunizing human with an optional antigen. Further, when a mouse monoclonal antibody is administered to a human body, there is a risk of the occurrence of a variety of adverse effects, because the antibody is a heterogeneous protein to human. Therefore, an antibody with lowered antigenicity to human is preferred when the antibody is administered to human.

Method for the production of human monoclonal antibodies involves transformation techniques with Epstein-Barr virus (EBV), and fusion techniques in which thus transformed cells and parent cells are fused; methods in which a chimeric antibody or a humanized antibody is produced using genetic engineering techniques; and the like in addition to cell fusion techniques. Chimeric antibody refers to an antibody that was produced by linking immunoglobulin gene fragments from heterogeneous animals. Humanized antibody refers to an antibody having a substituted primary structure in part other than a complementarity determining region (CDR) of H chain and L chain with the corresponding primary structure of a human antibody through introducing the alteration to a mouse antibody or the like that is heterogeneous to human.

For the production of a chimeric antibody, a mouse is immunized first, and an antibody variable region (V region) that binds to an antigen is excised from a gene of the mouse monoclonal antibody. Thereafter, the V region is linked to a gene of an antibody constant region (C region) derived from human myeloma to give a chimeric gene. Upon expression of this chimeric gene in a host cell, human-mouse monoclonal antibody can be produced. Because chimeric antibodies are less antigenic to human, they can be utilized as a monoclonal antibody for therapeutic use to be administered into a human body, or for use in diagnostic imaging. Known techniques relevant to chimeric antibodies involve Japanese patent unexamined publication No. Hei 05-304989, Japanese patent unexamined publication No. Hei 04-330295, WO9106649, Japanese patent unexamined publication No. Sho 63-036786, Japanese patent examined publication No. Hei 06-98021, and the like.

Moreover, humanized antibodies were recently developed, which are appreciated as being more useful than chimeric antibodies. Humanized antibody refers to an antibody that is humanized as a whole molecule except for CDR of an antibody molecule by grafting only a sequence of a gene for an antigen-binding site (CDR: complementarity determining region) of an antibody molecule into a gene of a human antibody (CDR grafting). This antibody is appreciated as being safer with less antigenicity than the human-mouse chimeric antibody because it has less part derived from a mouse antibody. When SHM-D 33 strain (ATCC CRL 1668) or RF-S1 strain, both of which being human/mouse heteromyeloma, is used as a parent cell for producing a human monoclonal antibody, high fusion efficiency can be achieved that is equivalent to mouse parent cells. Hybridoma that was obtained using these parent cells can be cloned without feeder cells, and it can produce IgG type antibody in a comparatively stable manner at a large amount. For the culture of the parent cells, ERDF medium supplemented with 15% FCS may be used, although other operation may be similarly carried out to the operation for the murine cells. Additionally, in order to produce an IgG type human monoclonal antibody, human lymphocytes collected from peripheral blood may be preferably employed, which were sufficiently sensitized with an antigen. When it is difficult to obtain sufficiently sensitized lymphocytes, sensitization with an antigen may be also conducted in vitro. In Japan, clinical trials have been currently carried out for humanized antibodies to adult T cell leukemia. In respect to the production of human antibodies and the related art, for example, reference should be made to those disclosed in Genentech Inc., USA (WO9222653, WO9845332, WO9404679, WO9837200, WO9404679) and Celltech Inc., England (WO9429451, WO9429351, WO9413805, WO9306231, WO9201059, WO9116927, WO9116928, WO9109967, WO8901974, WO8901783), and the like.

Using the methods and the like described above, the antibodies according to the present invention can be humanized, and such antibodies would be extremely useful upon the administration to human.

Composition

The SRCL-P1 polynucleotides or proteins and antibody substances, and antagonists and the like of SRCL-P1 are possibly utilized in diagnostic, prophylactic and therapeutic methods, and for the development of reagents and drugs for various types of diseases involved in the accumulation of oxidized LDL (modified LDL) including for example, arteriosclerosis and the like, as well as disorders involved in the binding of AGE to cells such as glomerulosclerosis and the like, diabetic complications and AD, hyper β-lipoproteinemia, hypercholesterolemia, hypertriglyceridemia, hypo α-lipoproteinemia, transplantation, atherectomy, and post angiogenic restenosis, bacterial infections and the like. Further, the ingredient can be combined or blended with known medical drugs. For example, the ingredient can be combined or blended with therapeutic drugs of atherosclerosis, e.g., ACAT inhibitors, HMG-CoA reductase inhibitors, lipid regulants, bile acid regulants.

Pharmaceutical composition according to the present invention may comprise SRCL-P1 polynucleotides or proteins, substances that stimulate or inhibit the activity or activation of SRCL-P1 protein, substances including antibodies to SRCL-P1 protein and the like (hereinafter, referred to as "SRCL-P1 related substance"). The SRCL-P1 related substances can be used neat, or after subjecting to several kinds of treatment such as dilution in water and the like, and they may also be used after blending in pharmaceutical products, quasi drugs and the like. In these cases, the amount of the substance to be blended may be determined ad libitum. When the substance is formulated for the systemic administration, 0.001-50% by weight, in particular, 0.01-10% by weight is permissible. When the amount is less than 0.001%, sufficient action of lacrimation may not be enabled. When the amount is greater than 50%, properties such as stability, flavor and the like of the composition itself may be deteriorated.

The route of administration can be optionally selected from the administration via mucosa, transdermal administration, intramuscular administration, subcutaneous administration, endorectal administration, topical ocular administration, and the like, in addition to oral administration and intravenous administration described above.

The SRCL-P1 related substance according to the present invention may be included in the formulation as a salt. Pharmaceutically acceptable salts include for example, salts with base such as inorganic base, organic base and the like; acid addition salts such as those of inorganic acid, organic acid, basic or acidic amino acid. Inorganic bases include for example, alkaline metal such as sodium, potassium and the like; alkaline earth metal such as calcium, magnesium and the like; aluminum, ammonium and the like. Organic bases include for example, primary amines such as ethanolamine and the like; secondary amines such as diethylamine, diethanolamine, dicyclohexylamine, N,N'-dibenzylethylenediamine and the like; tertiary amines such as trimethylamine, triethylamine, pyridine, picoline, triethanolamine and the like. Inorganic acids include for example, hydrochloric acid, hydrobromic acid, nitric acid, sulfuric acid, phosphoric acid and the like. Organic acids include for example, formic acid, acetic acid, lactic acid, trifluoroacetic acid, fumaric acid, oxalic acid, tartaric acid, maleic acid, benzoic acid, citric acid, succinic acid, malic acid, methanesulfonic acid, ethanesulfonic acid, benzenesulfonic acid, p-toluenesulfonic acid and the like. Basic amino acids include for example, arginine, lysine, ornithine and the like. Acidic amino acids include for example, aspartic acid, glutamic acid and the like.

Examples of dosage forms for use in oral administration include powdered formulations, granulated formulations, encapsulated formulations, pills, tablets, elixirs, suspensions, emulsions, syrups and the like, which may be selected ad libitum. In addition, such formulations may be modified, which may involve release control, stabilization, facilitation of disintegration, blocking of disintegration, enteric coating, facilitation of absorption and the like. Moreover, examples of dosage forms for the intraoral topical administration include chewable formulations, sublingual formulations, buccal formulations, lozenges, ointments, plasters, liquid formulations and the like, which may be selected ad libitum. Further, such formulations may be modified, which may involve release control, stabilization, facilitation of disintegration, blocking of disintegration, enteric coating, facilitation of absorption and the like.

Known drug delivery system (DDS) techniques may be applied to dosage forms as described above. DDS formulation referred to herein involves sustained release formulations, topically applied formulations (lozenges, buccal formulations, sublingual formulations), drug controlled release formulations, enteric coated formulations, formulations soluble in stomach and the like, which are formulations that are prepared so that most appropriate dosage form is accomplished taking into account of the administration route, bioavailability, adverse effect and the like.

Components for DDS essentially comprise a drug, a drug release module, a coating and a therapy program. In detail, the drug having a short half life is preferred, which permits rapid decline of the blood concentration particularly upon cessation of the release thereof. The coating is preferably nonreactive to the body tissue of the part to which the drug is administered. In addition, the therapy program is preferably configured so that the most optimal drug concentration is kept during the predetermined period. The drug release module substantially has a drug storage, a release control part, an energy source, and a release opening or a release surface. All of these fundamental components are not necessarily required, and thus addition, deletion or the like may be optionally carried out to select the best mode.

Examples of materials which can be used for DDS include polymers, cyclodextrin derivatives, lecithin and the like. The polymer may include insoluble polymers (silicone, ethylene-vinyl acetate copolymer, ethylene-vinyl alcohol copolymer, ethylcellulose, cellulose acetate and the like), water soluble polymers and hydroxyl gel-forming polymers (polyacrylamide, polyhydroxyethyl methacrylate cross-linked form, polyacryl cross-linked form, polyvinyl alcohol, polyethyleneoxide, water soluble cellulose derivatives, cross-linked poloxamer, chitin, chitosan and the like), slow dissolving polymers (ethyl cellulose, a partial ester of methylvinyl ether-maleic anhydride copolymer and the like), polymers soluble in stomach (hydroxylpropylmethyl cellulose, hydroxylpropyl cellulose, carmellose sodium, macrogol, polyvinylpyrrolidone, dimethylaminoethyl methacrylate-methyl methacrylate copolymer and the like), enteric polymers (hydroxylpropylmethyl cellulose phthalate, cellulose acetate phthalate, hydroxylpropylmethyl cellulose acetate succinate, carboxymethylethyl cellulose, acrylic acid polymers and the like), biodegradable polymers (heat coagulation or cross-linked albumin, cross-linked gelatin, collagen, fibrin, polycyanoacrylate, polyglycolic acid, polylactic acid, poly β-hydroxyacetic acid, polycaprolactone and the like), which can be selected ad libitum on the basis of the dosage form.

In particular, silicone, ethylene-vinyl acetate copolymer, ethylene-vinyl alcohol copolymer, a partial ester of methylvinyl ether-maleic anhydride copolymer can be used for the control of drug release; cellulose acetate can be used as a material of a osmotic pressure pump; ethyl cellulose, hydroxypropylmethyl cellulose, hydroxypropyl cellulose, methyl cellulose can be used as a material of a membrane of slow dissolving formulations; and polyacryl cross-linked form can be used as an attaching agent to oral mucosa or ophthalmic mucosa.

Further, the formulation can be manufactured with adding solvent, excipient, coating agent, base, binding agent, lubricant, disintegrant, solubilizing agent, suspending agent, thickening agent, emulsifying agent, stabilizing agent, buffering agent, isotonizing agent, soothing agent, preservative agent, flavoring agent, fragrance agent, coloring agent and the like in compliance with its dosage form (known dosages form such as forms for oral administration, injection, suppository and the like).

Although specific examples are respectively illustrated below, these examples should not be construed as limiting the present invention.

[solvent] purified water, water for injection, saline, peanut oil, ethanol, glycerol;

[excipient] starches, lactose, glucose, sucrose, crystalline cellulose, calcium sulfate, calcium carbonate, talc, titanium oxide, trehalose, xylitol;

[coating agent] sucrose, gelatin, cellulose acetate phthalate and polymers as described above;

[base] vaseline, vegetable oil, macrogol, base for oil in water emulsion, base for water in oil emulsion;

[binding agent] natural polymer compounds such as starch and derivatives thereof, cellulose and derivatives thereof, gelatin, sodium alginate, gum tragacanth, gum arabic, and the like; synthetic polymers such as polyvinylpyrrolidone and the like; dextrin, hydroxylpropyl starch;

[lubricant] stearic acid and salts thereof, talc, waxes, wheat starch, macrogol, hydrogenated vegetable oil, sucrose fatty acid ester, polyethylene glycol;

[disintegrant] starch and derivatives thereof, agar, gelatin powder, sodium bicarbonate, cellulose and derivatives thereof, carmellose calcium, hydroxypropyl starch, carboxymethyl cellulose, and salts and derivatives thereof, poorly substituted hydroxypropyl cellulose;

[solubilizing agent]cyclodextrin, ethanol, propylene glycol, polyethylene glycol;

[suspending agent] gum arabic, gum tragacanth, sodium alginate, aluminum monostearate, citric acid, various surfactants;

[thickening agent] carmellose sodium, polyvinylpyrrolidone, methyl cellulose, hydroxypropylmethyl cellulose, polyvinyl alcohol, gum tragacanth, gum arabic, sodium alginate;

[emulsifying agent] gum arabic, cholesterol, gum tragacanth, methyl cellulose, various surfactants, lecithin;

[stabilizing agent] sodium bisulfite, ascorbic acid, tocopherol, chelating agent, inert gas, reducing agent;

[buffering agent] sodium hydrogenphosphate, sodium acetate, boric acid;

[isotonizing agent] sodium chloride, glucose;

[soothing agent] procaine hydrochloride, lidocaine, benzyl alcohol;

[preservative agent] benzoic acid and salts thereof, p-hydroxybenzoic esters, chlorobutanol, inverted soap, benzyl alcohol, phenol, thimerosal;

[flavoring agent] sucrose, saccharin, glycyrrhiza extract, sorbitol, xylitol, glycerol;

[fragrance agent] orange peel tincture, rose oil;

[coloring agent] water soluble edible dye, lake dye.

EXAMPLES

Novel scavenger receptor according to the present invention is described in more detail by the following non-limiting illustrative examples. However, the present invention should not be construed to be limited by the examples.

Specifically, search on EST database (Example 1); preparation of probes for the screening (Example 2); screening of a cDNA library from human placenta (Example 3); base sequencing of novel human scavenger receptor (Example 4); and obtaining novel mouse scavenger receptor cDNA (Example 5); as well as method for producing a transfectant that transiently expresses the novel human scavenger receptor (Examples 6 and 7); method for producing a transfectant that stably expresses the novel human scavenger receptor (Examples 8 and 9); verification of the binding specificity of the novel human scavenger receptor (Example 10); demonstration of phagocytic capacity (Example 11); and demonstration of expression in vascular endothelial cells (Example 12) are described below, all of which were illustrated.

Example 1

Search on EST Database

By comparing amino acid sequences of known collecting, i.e., human MBP, human SP-A and human SP-D (see, FIGS. 2 and 3, wherein, circumscribed amino acid residues denote the part that are recognized to be homologous), a region highly conserved between the molecules was searched. Consequently, it was revealed that 27 amino acids corresponding to from position 220 to position 246 of the human MBP amino acid sequence (FIG. 3, outlined characters, SEQ ID NO: 5) were highly conserved. Therefore, several consensus sequences in compliance with this region were produced, and search on EST (Expressed Sequence Tags) database was conducted. EST database that was employed contained 676750 sequences dated Oct. 11, 1996.

As a result, several data were obtained for highly homologous amino acid sequence to the 27 amino acids described above. The amino acid sequences of thus resultant data were searched on GenBank/EST database, and determined whether they were any of known or unknown substance. Consequently, two data (accession number: W72977 and R74387) that exhibit high homology but contain unknown nucleotide sequence could be obtained among data that were obtained when the amino acid sequence set out below was used as a consensus sequence: Glu-Lys-Cys-Val-Glu-Met-Tyr-Thr-Asp-Gly-Lys-Trp-Asn-Asp-Arg-Asn-Cys-Leu-Gln-Ser-Arg-Leu-Ala-Ile-Cys-Glu-Phe (SEQ ID NO: 6). These data were respectively derived from placenta and fetal heart, which represent a part of the nucleotide sequence of a novel collectin.

Accordingly, a clone derived from fetal heart (I.M.A.G.E. Consortium Clone ID 34472) was purchased from ATCC (American Type Culture Collection) among these, and utilized in the preparation of probes for the screening to obtain a novel scavenger receptor below.

Example 2

Preparation of Probes for Screening

The nucleotide sequence of an insert DNA of the above-described clone was sequenced with a primer (Pharmacia Co., M13 Universal Primer (SEQ ID NO: 7,5'-fluorescein-cgacgttgtaaaacgacggccagt-3') and M13 Reverse Primer (SEQ ID NO: 8, 5'-fluorescein-caggaaacagctatgac-3')).

Thus resulting nucleotide sequences was aligned to the amino acid sequence of an open reading flame of a collectin, and then a nucleotide sequence corresponding to the amino acid sequence that can be read therefrom was extracted. Primers for digoxigenin (DIG) labeled cDNA probe that correspond to a part of the extracted sequence (Reverse primer: caatctgatgagaaggtgatg (SEQ ID NO: 9) and Forward primer: acgaggggctggatgggacat (SEQ ID NO: 10)) were produced using Applied Biosystems Inc., 392A DNA/RNA synthesizer. DIG labeling was conducted using a PCR DIG probe synthesis kit (Boeringer Mannheim Co., Ltd). The constitution of a reaction is as follows: 2 µl (100 ng) of plasmid DNA (clone W72977, 50 ng/µl); 5 µl of 10× buffer; 5 µl of 25 mM $MgCl_2$; 5 µl of dNTP (PCR labeling mix); 2.5 µl of 20 µM Reverse primer; 5 µl of 20 µM Forward primer; 28 µl of $H_2O$; 0.5 µl of Taq polymerase. PCR reaction was performed using Atto Co., Ltd., Zymoreactor, with 35 cycles of 92° C. for 1 min, 55° C. for 1 min, and 72° C. for 2 min.

Example 3

Screening of cDNA Library Derived from Human Placenta

A phage cDNA library derived from human placenta was first subjected to the titration as follows. A solution of 0.2 ml of *Escherichia coli* Y1090r, which had been cultured in mLB medium (LB medium (1 g triptone, 0.5 g yeast extract, 0.5 g NaCl/100 ml) containing 10 mM $MgSO_4$ and 0.2% maltose) at 37° C. for 16 hours, and 0.1 ml of cDNA library serially diluted with SM buffer (5.8 g NaCl, 2 g $MgSO_4.7H_2O$, 25 ml of 2 M Tris-HCl (pH 7.5), 5 ml of 2% gelatin/L) were incubated at 37° C. for 15 min. Thereafter, the mixture was added to 2.5 ml of LB-TOP agarose (0.75% agarose/LB medium) to give a homogenous mixture, and plated on 90 mmΦ LB medium plate (Iwaki glass Co., Ltd.) (1.5% agar/LB medium). The medium was hardened in 15 minutes at room temperature, followed by incubation at 42° C. for 5 hours. After counting the plaque number of each plate, the titer of phage of each plate was calculated. As a result, the titer was calculated to be $2.1 \times 10^{10}$ pfu/ml. Thus titrated cDNA library was screened as follows using the probes produced in accordance with Example 2.

A solution of 0.6 ml of *Escherichia coli* Y1090r, which had been cultured in mLB medium at 37° C. for 16 hours, and $1 \times 10^5$ pfu of the cDNA library diluted with SM buffer were incubated at 37° C. for 15 min. Thereafter, the mixture was added to 7.5 ml of LB-TOP agarose (0.75% agarose) to give a homogenous mixture. Ten plates of 140 mm² of LB medium rectangular plate (Nissui Seiyaku Co., Ltd.) to which the mixture was plated were provided, and hardened in 15 minutes at room temperature, followed by incubation at 42° C. for 5 hours. After confirming the plaque formation, transfer to a nylon membrane was conducted. The transfer was carried out using Nytran 13N (Schleicher and Schuell Co.). A filter of 12.5 cm×9.0 cm was immersed in distilled water, and moisturized for 10 minutes. Thereafter, the excess moisture was eliminated on a Whatman 3 mM paper, and the filter was placed on the plate with the plaques formed. After leaving to stand for two minutes, the filter was stripped off, and air dried for 10 minutes. Phage DNA was modified with 0.2 M NaOH/ 1.5 M NaCl for 2 min, and neutralized with 0.4 M Tris-HCl (pH7.6)/2×SSC for 2 min, followed by washes with 2×SSC for 2 min. Thereafter, the phage DNA was fixed on the membrane by ultraviolet irradiation using GS GENE LINKER (Bio-Rad Inc.,). Detection of the hybridization and signals was executed as described below. The filter was moisturized with 2×SSC, and the excess moisture was eliminated with a Whatman 3 mM paper. Then the filter was placed into a hybridization bag, and subjected to prehybridization in a hybridization solution (5×SSC, 1% blocking agent, 0.1% N-lauroylsarcosine, 0.02% SDS) at 68° C. for 1 hour. Subsequently, the hybridization solution was removed from the bag, and thereto added a hybridization solution that was prepared to give 10 ng/ml of DIG labeled cDNA probe. Hybridization was carried out at 55° C. for 16 hours. After the hybridization was completed, the filter washed with 2×SSC/ 0.1% SDS solution for 5 min twice at room temperature, and with 0.5×SSC/0.1% SDS solution for 15 min twice at 55° C. Next, SDS was removed with DIG buffer I (100 mM Tris-HCl, 150 mM NaCl (pH7.5)) for 1 minute, followed by blocking of the filter with DIG buffer II (1% blocking agent, DIG buffer I) for 30 min. After the wash with DIG buffer I for 1 min, an antibody reaction was then allowed for 30 min through the addition of a solution of 5,000× anti-DIG alkaline phosphatase labeled antibody (Boeringer Mannheim Co., Ltd.) diluted with DIG buffer II. The filter washed twice with DIG buffer I for 15 min at room temperature. The concentration of $Mg^{2+}$ was elevated by the treatment with DIG buffer III (100 mM Tris-HCl, 100 mM NaCl (pH 9.5), 50 mM $MgCl_2$) for 3 min, and then a solution of NBT/BCIP (Wako Pure Chemical Industries, Ltd.) in DIG buffer III was added to the mixture for the color development. Accordingly, ten positive clones were obtained. Plaques corresponding to these clones were excised, and they were respectively placed in a tube containing 1 ml of SM buffer. After stirring for 10 min, the solution was serially diluted with SM buffer. Then, 0.1 ml of thus diluted solution was mixed with a solution of 0.2 ml of *Escherichia coli* Y1090r that had been cultured in mLB medium at 37° C. for 16 hours, and the mixture was incubated at 37° C. for 15 min. Thereafter, the mixture was added to 2.5 ml of LB-TOP agarose to give a homogenous mixture, and plated on 90 mmΦ LB medium plate. Ten plates prepared in this manner were hardened in 15 minutes at room temperature, followed by incubation at 42° C. for 5 hours. Several plaques were obtained, which were subjected to the secondary screening similarly to the primary screening.

Example 4

Sequencing of Nucleotide Sequence of Human Novel Scavenger Receptor

A plaque of a clone, which was deemed to be proper among the positive clones obtained in the secondary screening, was excised from the plate. Thus resulting plaque was placed in a tube containing 200 μl of distilled water. After stirring for 30 min, the solution was centrifuged at 15,000 rpm for 5 min to give a supernatant.

Thus resultant supernatant was used as a template to amplify an insert DNA by PCR using TaKaRa LA PCR Kit Ver.2 (Takara Shuzo Co., Ltd.). The constitution of the reaction is as follows: 27 μl of the supernatant, 5 μl of 10×LA PCR buffer II ($Mg^{2+}$ free), 5 μl of 25 mM $MgCl_2$, 8 μl of dNTP mix, 2.5 μl of 20 μM λgt11 Reverse Primer (SEQ ID NO: 11, 5'-ttgacaccagaccaactggtaatg-3'), 2.5 μl of 20 μM λgt11 Forward Primer (SEQ ID NO: 12, 5'-ggtggcgacgactcctggagcccg-3'), 0.5 μl of LA Taq polymerase, $H_2O$ added to adjust the total volume of 50 μl). The PCR reaction was carried out using Gene Amp PCR system 9600 manufactured by Applied Biosystems Inc., with 30 cycles of at 98° C. for 20 seconds and at 68° C. for 5 minutes. The PCR product was confirmed on 1% agarose gel electrophoresis, and was purified by excising from the gel. Sephaglas B and Prep Kit manufactured by Pharmacia Co., was used for the purification.

The DNA fragment excised was incorporated into pCR2.1 vector included in TA cloning kit manufactured by Invitrogen Co. The recombinant vector was transformed into TOP10F' cells included in the TA cloning kit manufactured by Invitrogen Co. The transformant was cultured in LB medium (100 μg/ml ampicillin), and then three kinds of plasmid DNA per each clone were extracted by an alkali SDS method.

Thus resulting DNA was cut with a restriction enzyme that was envisaged to be suitable. Each DNA fragment was incorporated into pUC18 vector and transformed into XL-1 Blue cells. The transformant was cultured in LB medium (100 μg/ml ampicillin), and then a plasmid was extracted by an alkali SDS method. Accordingly, the plasmids below were obtained: a plasmid containing an EcoR I-Hind III fragment or a Hind III-EcoR I fragment from CL-P1-2-1; a plasmid containing an EcoR I-BamH I fragment, a BamH I-Sma I fragment, a Sma I-Hind III fragment, a Kpn I-Sau3A I fragment, a Sau3A I-EcoR I fragment, an EcoR I-Kpn I fragment or an EcoR I-Sma I fragment from CL-P1-3-4; a plasmid containing an EcoR I-BamH I fragment, a BamH I-Sma I fragment, a Sma I-Hind III fragment, a Kpn I-Sau3A I fragment, a Sau3A I-EcoR I fragment, an EcoR I-Kpn I fragment or a Kpn I-EcoR I fragment from CL-P1-3-7. Primers for the use were: M13 Universal Primer (SEQ ID NO: 7) and M13 Reverse Primer (SEQ ID NO: 8) attached to AutoRead Sequencing Kit (Pharmacia Co.,), and the following primers produced by using a DNA/RNA synthesizer, which were labeled with FITC (Pharmacia Co., FluorePrime), followed by sequencing of the nucleotide sequence of their entire regions with AutoRead Sequencing Kit and A.L.F. Auto Sequencer manufactured by Pharmacia Co.

HPP 1: 5'-fluorescein-cgtgaaaatgaatggaagtgg-3' (SEQ ID NO: 13),

HPP 2: 5'-fluorescein-ttttatccattgctgttcctc-3' (SEQ ID NO: 14),

HPP 3: 5'-fluorescein-ctggcagtccccgaggtccag-3' (SEQ ID NO: 15),

HPP 5: 5'-fluorescein-gctggtccccccggagagcgt-3' (SEQ ID NO: 16).

Figure 4:
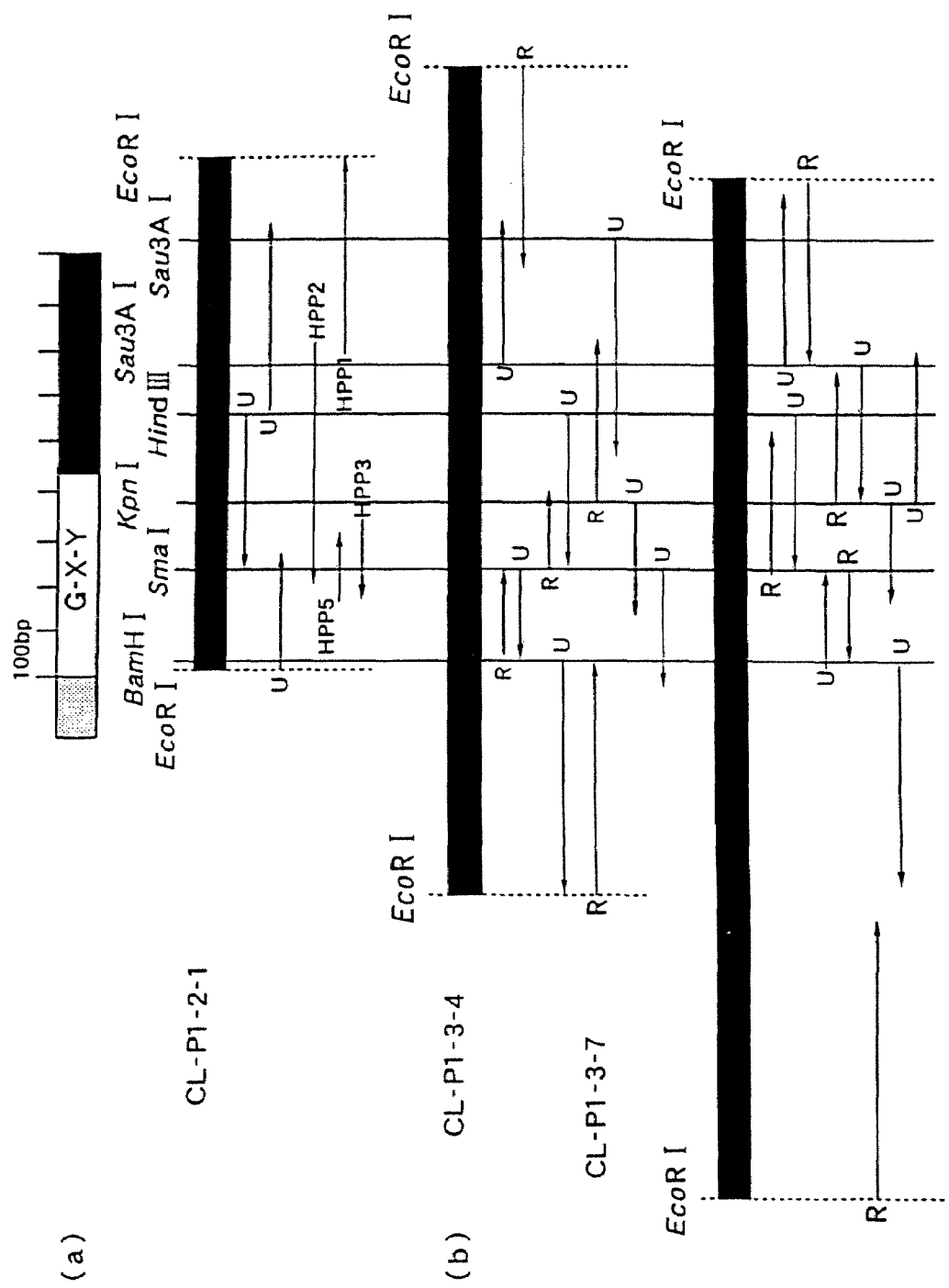
FIG. 4(*b*) depicts drawings showing a nucleotide sequence read by a sequencer and each primer employed for the sequencing of the novel scavenger receptor of the present invention.

Outline of the sequencing of the nucleotide sequences conducted as above is shown in FIG. 4. FIG. 4 (*a*) represents ORF of a collectin-like structural part of the obtained scavenger receptor, in which G-X-Y (wherein G denotes glycine, X and Y may be any one of amino acid residues) represents a collagen-like domain. In addition, FIG. 4 (*b*) represents each name of the primers described above, the nucleotide sequence that was read by a sequencer, which is shown by arrows, and M13 Universal Primer (shown as "U") and M13 Reverse Primer (shown as "R").

Moreover, the nucleotide sequence of 5' end region including a transcription initiation site of this sequence was determined using Cap site cDNA.

First PCR was carried out with Cap Site cDNA, Human Liver (NIPPON GENE KK) using 1RC2 Primer (5'-caaggtacgccacagcgtatg-3' (SEQ ID NO: 17)) attached thereto, and TGP1 Primer (5'-tcttcagtttccctaatccc-3' (SEQ ID NO: 18)) that was synthesized by 392A DNA/RNA synthesizer manufactured by Applied Biosystems Inc. The reaction mixture contained LA PCR Buffer II ($Mg^{2+}$ free), 2.5 mM $MgCl_2$, 1 μl of each 200 μM dATP, dCTP, dGTP and dTTP (all of which were manufactured by Takara Shuzo Co., Ltd.), Cap Site cDNA Human Liver, 0.5 μM 1RC2 Primer (manufactured by NIPPON GENE KK), and 0.5 μM TGP1 Primer in a total liquid volume of 50 μl. PCR was carried out with a program involving 35 cycles of: heat denaturation at 95° C. for 20 seconds, annealing at 60° C. for 20 seconds, elongation at 72° C. for 20 seconds, as well as heat denaturation at 95° C. for 5 minutes prior to repeating the reaction and finally elongation at 72° C. for 10 minutes. After completing the first PCR reaction, nested PCR was carried out. One μl of the product of the first PCR was used as a template, whilst primers employed were 2RC2 Primer (5'-gtacgccacagcgtatgatgc-3' (SEQ ID NO: 19)) as attached, and synthetic TGP2 Primer (5'-cattct-tgacaaacttcatag-3' (SEQ ID NO: 20)), which was synthesized similarly to TGP1 Primer. The reaction was conducted with a similar constitution of the reaction and program to those of the first PCR, except that cycle number was 25 cycles. Such a PCR reaction was carried out with TaKaRa PCR Thermal Cycler 480 manufactured by Takara Shuzo Co., Ltd. Thus resulting PCR product was confirmed on agarose gel electrophoresis. Thereafter, the band was excised from the gel, followed by freezing at −80° C. for 10 minutes and centrifugation at 15,000 rpm for 10 minutes. After the centrifugation, the supernatant was precipitated with ethanol. Accordingly, the purification was accomplished.

Purified DNA fragment was incorporated into pT7Blue Vector manufactured by Novagen Co., and thus resulting vector was transformed into competent XL1-Blue cells. The transformant was cultured in LB medium (100 μg/ml ampicillin), and then a plasmid was extracted by an alkali SDS method. Nucleotide sequence was determined with Auto-Read Sequencing Kit and A. L. F. DNA Sequencer manufactured by Pharmacia Co. Primers employed were M13 Universal Primer (SEQ ID NO: 7) and M13 Reverse Primer (SEQ ID NO: 8) attached to AutoRead Sequencing Kit.

Additionally, screening of a cDNA library derived from placenta (Clontech Co.,) was carried out after synthesizing a primer: 5'-atcttgctgcagattcgtgac-3' (SEQ ID NO: 21), corresponding to the upstream direction from the sequence of an N terminal portion of the cDNA clone obtained for the confirmation of the N terminus. The screening was carried out by PCR using a primer synthesized corresponding to the upstream direction: 5'-atcttgctgcagattcgtgac-3' (SEQ ID NO: 21) and a primer λgt11 5' Sequencing Primer: 5'-gactcctg-gagcccg-3' (SEQ ID NO: 22) that is a part included in the vector. The reaction mixture was prepared by adding 2.5 mM $MgCl_2$, 1×LA PCR Buffer II ($Mg^{2+}$ free), 2U TaKaRa LA Taq, two kinds of primers (each 0.2 μM 5'-atcttgctgcagattcgt-gac-3' (SEQ ID NO: 21), λgt11 5' Sequencing Primer: 5'-gactcctggagcccg-3' (SEQ ID NO: 22)), 1 μl of a cDNA library derived from placenta to water to give the total volume of 50 μl. The reaction was executed with one cycle of at 94° C. for 2 minutes, and 50 cycles of at 94° C. for 30 seconds, at 60° C. for 30 seconds, and at 72° C. for 1 minute and 30 seconds.

Thus resulting cDNA was separated on agarose gel electrophoresis, and stained with a solution of ethidium bromide (0.1 μg/ml). Upon confirmation of the migration pattern with a trans illuminator, the amplification of an insert corresponding to about 600 bp was demonstrated. Then, the amplified part was excised from the agarose gel, followed by freezing at −80° C. for 10 minutes and centrifugation at 15,000 rpm for 10 minutes. After the centrifugation, the supernatant was recovered and subjected to the precipitation with ethanol. Accordingly, the purification was accomplished. Purified DNA fragment was incorporated into pT7Blue Vector manufactured by Novagen Co., and thus resulting vector was transformed into competent XL1-Blue cells. The transformant was cultured in LB medium (50 μg/ml ampicillin), and then a plasmid was extracted by an alkali SDS method. Nucleotide sequence was determined with DNA Sequencing Kit and Sequencer ABI PRISM 377 manufactured by PE Applied Biosystems Inc. Primers employed were M13 Universal Primer (SEQ ID NO: 7) and M13 Reverse Primer (SEQ ID NO: 8) attached to AutoRead Sequencing kit manufactured by Pharmacia Co.

Consequently, it was revealed that the sequence contained further 604 bases long from the nucleotide sequence that had been obtained to the N-terminal direction. Accordingly, it was confirmed that the resultant cDNA of hSRCL-P1 obtained hereby includes 2628 bases, having ORF (open reading frame) of 2226 bases (SEQ ID NO: 1), which encodes amino acid sequence of 742 amino acids set out in SEQ ID NO: 2.

Next, search on the homology for DNA and amino acid on GenBank database was conducted. As a result, the resulting amino acid sequence was revealed to be that of a novel protein, which is distinct from any collectin/scavenger receptors that have been found so far.

Furthermore, a mutant was obtained, having deletion of amino acids position 483 to 606 of the amino acid sequence set out in SEQ ID NO: 2, encoded by the nucleotide sequences position 74 to 1993 set out in SEQ ID NO: 23.

Example 5

Obtaining cDNA of Mouse Novel Scavenger Receptor

In a similar manner to that for hSRCL-P1, mSRCL-P1 gene could be obtained through the screening of a mouse liver cDNA library. The resulting cDNA clone of mSRCL-P1 includes 2637 bases, having ORF (open reading frame) of 2226 bases (SEQ ID NO: 3), which was confirmed to encode amino acid sequence of 742 amino acids set out in SEQ ID NO: 4.

Example 6

Construction of Transient Expression Vector of hSRCL-P1, pEGFP-N1-hSRCL-P1

Amplification of hSRCL-P1, from initiation codon to termination codon, set out in SEQ ID NO: 1 was carried out first using a primer consisting of the nucleotide sequence: ccgctc-gagcggtcaccatgaaagacgact (SEQ ID NO: 25) and a primer consisting of the nucleotide sequence: tccccgcggtaatgcagat-gacagtactgt (SEQ ID NO: 26) with a cDNA library derived from human placenta as a template by PCR (manufactured by Takara KK: Takara Thermal Cycler MP). Thus resulting hSRCL-P1cDNA was ligated to pT7Blue T-Vector (Novagen Co.), and transformed into *Escherichia coli*, XLI-Blue. A plasmid containing hSRCL-P1cDNA was purified from the resulting clone. Following the confirmation of the nucleotide sequence of the resulting plasmid with a sequencer, the plasmid with no error was digested with restriction enzymes Xho I and Sac II, and ligated to pEGFP-N1 vector (Clontech Co.) that had been digested with the same enzymes and purified. After the ligated plasmid was transformed into *Escherichia* coli, XLI-Blue, the resulting clone was cultured. The plasmid was then purified to give a transient expression vector pEGFP-N1-hSRCL-P1.

Example 7

Expression of hSRCL-P1 Using a Transient Expression System

Transient expression in CHO cells was attempted using the expression vector pEGFP-N1-hSRCL-P1 obtained in Example 6, and LIPOFECTAMINE 2000 (LF2000) Reagent (GIBCO BRL Co.). A solution of 0.2 ml of LF2000 Reagent (LF2000 Reagent 12 µl, Nutrient Mixture F-12 Ham (Ham's F-12 medium, (manufactured by Sigma Co.))) was first prepared, and incubated at room temperature for 5 minutes. Then, 0.2 ml of a vector solution (pEGFP-N1-hSRCL-P1 vector 4 µg, Ham's F-12 medium) was admixed therewith, followed by the incubation for 20 minutes. Thereafter, the solution was added to CHO cells that had been cultured to a high density in a 35 mm dish containing 2 ml of Ham's F-12 medium (containing 5% FCS). After incubating at 37° C. for 4 hours in the presence of 5% $CO_2$, the medium was replaced with a flesh medium, followed by subsequent incubation at 37° C. for 20 hours in the presence of 5% $CO_2$. The presence or absence of the expression could be confirmed by the observation of the fluorescent image for GFP by a fluorescence observation system of an inverted system microscope IX70 manufactured by Olympus Co., Ltd. Thus resultant cells were identified as cells transiently expressing hSRCL-P1.

Example 8

Construction of a Vector pcDNA3.1/Myc-His A-hSRCL-P1 for Producing Cell Strain Stably Expressing hSRCL-P1

Amplification of hSRCL-P1, from initiation codon to termination codon, set out in SEQ ID NO: 1 was carried out first using a primer consisting of the nucleotide sequence: aatgcggccgcaccatgaaagacgacttcgcagag (SEQ ID NO: 27) and a primer consisting of the nucleotide sequence: gctctagaccgcggtaatgcagatgacagtac (SEQ ID NO: 28) with a cDNA library derived from human placenta as a template by PCR (manufactured by Takara KK: Takara Thermal Cycler MP). Thus resulting hSRCL-P1cDNA was ligated to pT7Blue T-Vector (Novagen Co.), and transformed into Escherichia coli, XLI-Blue. A plasmid containing hSRCL-P1cDNA was purified from the resulting clone. Following the confirmation of the nucleotide sequence of the resulting plasmid with a sequencer, the plasmid with no error was digested with restriction enzymes Not I and Sac II, and ligated to pcDNA3.1/Myc-His A vector (Invitrogen Co.) that had been digested with the same enzymes and purified. After the ligated plasmid was transformed into Escherichia coli, XLI-Blue, the resulting clone was cultured. The plasmid was then purified to give vector pcDNA3.1/Myc-His A-hSRCL-P1 for producing a stable cell strain.

Example 9

Preparation of Cell Strain Stably Expressing hSRCL-P1

Stable expression of hSRCL-P1 was attempted using the expression vector pcDNA3.1/Myc-His A-hSRCL-P1 obtained in Example 8, and LIPOFECTAMINE 2000 (LF2000) Reagent (GIBCO BRL Co.). A 0.5 ml solution of LF2000 Reagent (LF2000 Reagent 30 µl, Ham's F-12 medium) was first prepared, and incubated at room temperature for 5 minutes. Then, 0.5 ml of a vector solution (vector 10 µg, Nutrient Mixture F-12 Ham (Ham's F-12 medium) (Sigma Co.)) was admixed therewith, followed by the incubation for 20 minutes. Thereafter, the solution was added to CHO cells that had been cultured to a high density in a 25 $cm^2$ flask containing 5 ml of Ham's F-12 medium (containing 5% FCS). After incubating at 37° C. for 4 hours in the presence of 5% $CO_2$, the medium was replaced with a flesh medium, followed by subsequent incubation at 37° C. for 20 hours in the presence of 5% $CO_2$. Next, the medium was replaced with Ham's F-12 medium containing 5% FCS, 0.4 mg/ml Geneticin (GIBCO BRL Co.), and 10 days culture was subsequently conducted. In the method, the medium was replaced once.

Through this selection by a drug for 10 days, only the transformed cells could survive and proliferated, however to the contrary, cells that were not transformed died. In order to obtain highly expressing cells from the resulting transformed cells, sorting was performed by a cell sorter (Becton Dickinson Co.). Staining of hSRCL-P1 expressed on the cell surface was first conducted. After washing the transformed cells in the 25 $cm^2$ flask with 5 ml PBS(−) twice, the cells were unstuck with 0.3 ml of 0.02% EDTA solution (Nakarai Tesc KK). The cells were suspended in 10 ml PBS (−), and thereafter centrifuged at 200×g for 7 minutes at 4° C. to remove the supernatant. To the remaining cells, added 50 µl of a solution of an anti-myc antibody (Invitrogen Co.) that was diluted with 2% FCS/PBS (−) by ten folds. After intimately suspending the cells, the suspension was incubated at 4° C. for 20 minutes. Thereafter, 10 ml of 2% FCS/PBS (−) was added thereto and suspended, followed by washes through the centrifugation at 200×g for 7 minutes at 4° C. and the removal of the supernatant. To the remaining cells, added 50 µl of a solution of a secondary antibody Alexa488 labeled anti-mouse IgG (H+L) that was diluted with 2% FCS/PBS (−) by ten folds. After intimately suspending the cells, the suspension was incubated at 4° C. for 20 minutes. Thereafter, 10 ml of 2% FCS/PBS (−) was added thereto and suspended, followed by washes through the centrifugation at 200×g for 7 minutes at 4° C. and the removal of the supernatant. The remaining cells were suspended in 0.5 ml of 2% FCS/PBS (−) to give a sorting sample. After the sample was passed through a 5 ml tube equipped with a cell strainer cap (Becton Dickinson Co.), it was applied to a cell sorter. CHO cells without subjecting to the transformation, which had been similarly treated, were used as control cells. Accordingly, a sample was selected, which exhibits fluorescence intensity of 10 times or greater than the control sample.

These cells were dispensed into 96-well cell culture plates, of which wells respectively contained 100 µl Ham's F-12 medium (containing 5% FCS, 0.4 mg/ml Geneticin), to charge a single cell per well. After the cells were cultured at 37° C. in the presence of 5% $CO_2$ for one week, additionally each 100 µl of a culture medium was added thereto followed by the additional culture for one week. A clone proliferated in the drug selection with Geneticin was divided into two parts, which were subjected to passages on 12-well and 24-well cell culture plates. Upon the passage, clones that proliferated from two cells or more per well were excluded, and the cells were plated at a cell number ratio of 9:1 to 12-well and 24-well cell culture plates. The cells were cultured at 37° C. in the presence of 5% $CO_2$ until the cells in the 12-well plate reach to high density. Then, the cells were stained again similarly to the procedure where individual clones were subjected to sorting, and thereafter, they were applied to FACS- Calibur (Becton Dickinson Co.) to determine the expression level. After determining a clone exhibiting the expression at a higher amount, respectively corresponding cells in the 24-well plate clone were identified as a stable expression cell strain (CHO/hSRCL-P1).

Example 10

Binding Specificity of hSRCL-P1

Binding specificity of hSRCL-P1 was examined using the stable expression cell strain CHO/hSRCL-P1, which was obtained in Example 9, for (1) yeast (Zymosan A Bioparticles, manufactured by Molecular Probes Co.); gram negative bacterium (*Escherichia coli* Bioparticles, manufactured by Molecular Probes Co.); or gram positive bacterium (*Staphylococcus aureus* Bioparticles, manufactured by Molecular Probes Co.), (2) oxidized LDL (2.0 mg/ml LDL added with 50 µM $CuSO_4$ followed by subjecting to the reaction for 24 hours and to the dialysis in PBS(−)), (3) AGE-HSA (AGE-human serum albumin, which was prepared according to Ikeda, K. et al., Biochemistry 35(24), 8075-8083 (1996)), or (4) mannose (α-D-Mannose BP-Probe, manufactured by Seikagaku Kogyo KK) or fucose (α-L-Fucose BP-Probe, manufactured by Seikagaku Kogyo KK).

CHO/hSRCL-P1 was first plated on a 35 mm bottom dish (Matsunami glass KK) at $1\times10^5$ cells, and cultured at 37° C. for 3 days in the presence of 5% $CO_2$. The culture was conducted in 2 ml of Ham's F-12 medium containing 5% FCS, 0.4 mg/ml Geneticin. After 3 days passed, the cells were washed twice with 1 ml of Minimum Essential Medium Alpha Medium containing 2% FCS (αMEM/2% FCS). Thereafter, each 1 ml of αMEM/2% FCS containing 25 µg/ml yeast, 25 µg/ml gram negative bacterium, 25 µg/ml gram positive bacterium, 5 µg/ml oxidized LDL, 10 µg/ml AGE, or 10 µg/ml mannose or 10 µg/ml fucose was added thereto. Three hours reaction at 4° C. was allowed, and thereafter, the cells were washed five times with 1 ml of αMEM/2% FCS.

Figure 5:
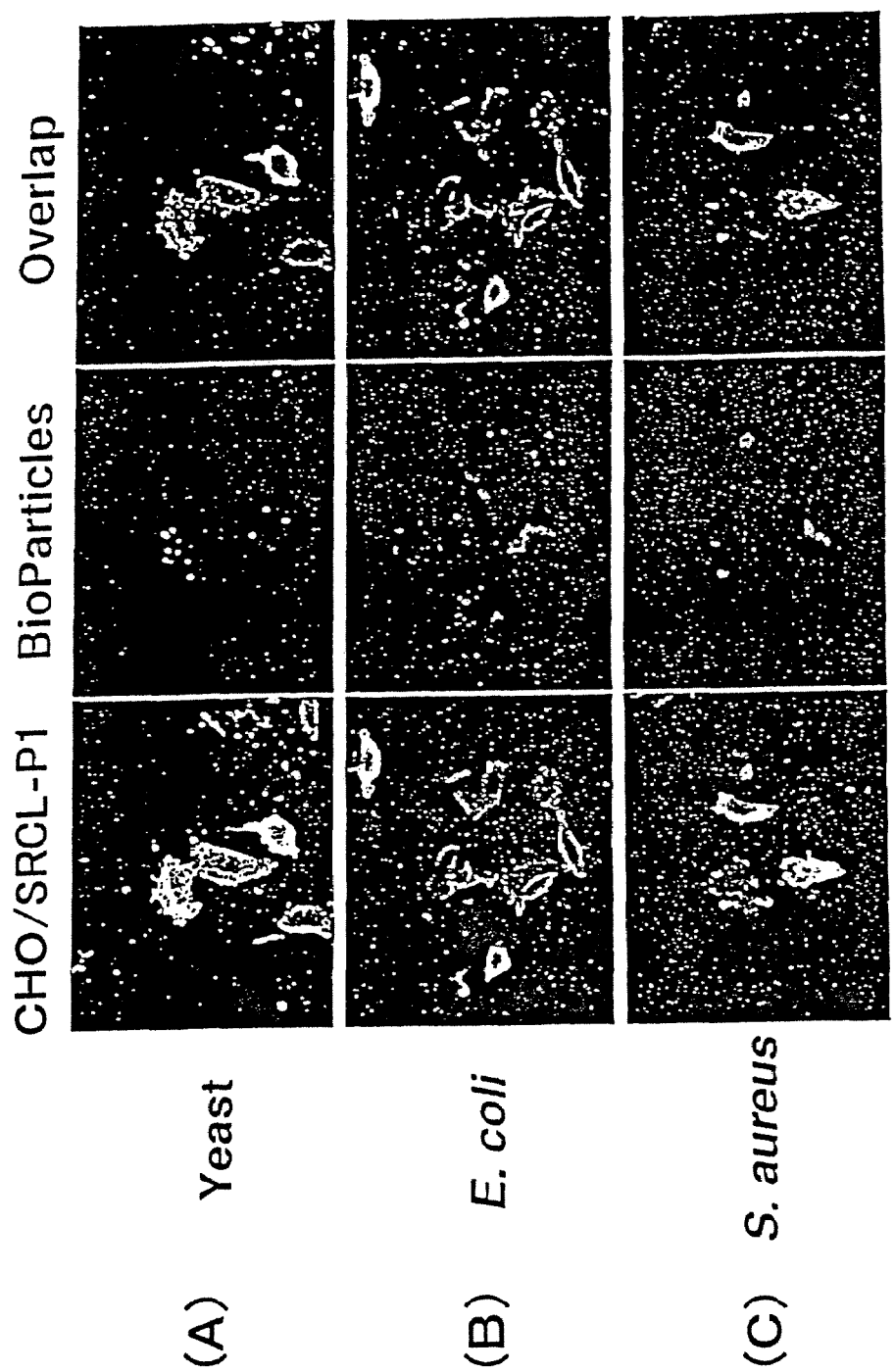
FIG. 5 is a drawing illustrating a manner how A: yeast, B: gram negative bacteria (*Escherichia coli*), and C: gram positive bacteria (*Staphylococcus aureus*) specifically bind to cells that are expressing hSRCL-P1.

The binding was confirmed as below. First, in regard to (2), (3) and (4), each 1 ml of 100 folds dilution of (2) an anti-oxidized phosphatidylcholine antibody; (3) an anti-HSA antibody (BIOSYS Co.); or (4) streptavidin, Alexa594 conjugate (Molecular Probes Co.) in αMEM/2% FCS was added, followed by further 30 minutes incubation at 4° C. Thereafter, the cells were washed three times with 1 ml of αMEM/2% FCS. Next, 0.2 ml of a solution of 4% paraformaldehyde/PBS (−) was added to any one of the above (1) to (4), and then the fixation was allowed by the incubation at room temperature for 20 minutes. Then 1 ml of TBSC (Takara Shuzo Co., Ltd, a buffer containing TBS (Tris-Buffered Saline) Powder which was adjusted to give a predetermined amount with sterilized and distilled water, and added with $CaCl_2$ at a final concentration of 5 mM) was used for three times washes. Next, in regard to (2) and (3), the reaction with secondary antibody was performed. More specifically, each 1 ml of 200 folds dilution of (2) rhodamine labeled anti-mouse IgM Mu Chain (Chemicon International Co.); or (3) Alexa 594 anti-goat IgG (H+L) (Molecular Probes Co.) in 25% BlockAce (Dainippon Pharmaceutical Co., Ltd.)/TBSC was added thereto, followed by further 30 minutes incubation at room temperature. Thereafter, the cells were washed three times with 1 ml of TBSC. Next, in regard to from (1) to (4), Slow-Fade Light Antifade Kit (Molecular Probes Co.) was used for the mounting to give samples for the observation under a fluorescence microscope. For each of the samples, the fluorescent image was observed by a fluorescence observation system of an inverted system microscope IX70 manufactured by Olympus Co., Ltd. The results are respectively depicted in FIG. 5 for (1) (A: yeast, B: gram negative bacterium (*Escherichia coli*), and C: gram positive bacterium (*Staphylococcus aureus*)), and in FIG. 6 for (2)-(4) (A: oxidized LDL, B: mannose, and C: AGE). As is clear from these figures, specific binding images could be observed in CHO cells that are stably expressing hSRCL-P1 in all cases of from (1) to (4). The results shown in FIG. 5, A-C, in which bacterium was employed, clearly indicated that each of the stained parts of hSRCL-P1 (in each left figure, stained in green) overlapped with each of the parts where the bacteria are present (in each middle figure, stained in red), which was found as Overlap in each right figure, and that each of the bacteria specifically bound to hSRCL-P1.

In addition, cells in which hSRCL-P1 was transiently expressed (see, Example 7) gave the similar results, which demonstrate the specific binding.

Example 11

Intracellular Incorporation of Binding Complex by Phagocytosis of hSRCL-P1

Figure 7:
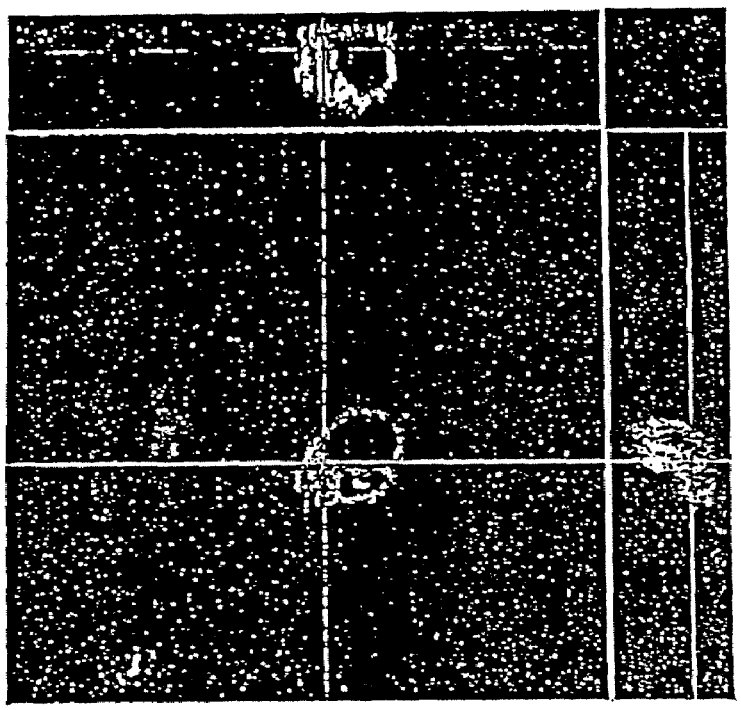
FIG. 7 is a drawing illustrating a manner how yeast is incorporated into cells that are expressing hSRCL-P1.

Intracellular incorporation of each binding complex, which was employed in Example 10, was observed using the transient expression cell and stable expression cell strains of hSRCL-P1 obtained in Examples 7 and 9. Incorporation of the binding complex was confirmed by modifying method described in Example 10, in which the reaction with the binding complex was performed at a temperature of 37° C. After staining, the incorporation status within the cells was observed by three-dimensional image processing using a confocal laser scanning microscope manufactured by Olympus Co., Ltd. The results in the examination where the transient expression cells were used are depicted in FIG. 7 in regard to those obtained for yeast, which reveal that yeast cells (stained in red) were incorporated into cells that were expressing hSRCL-P1 (stained in green). Furthermore, similar results were also obtained when the stable expression cell strain was employed.

Example 12

Demonstration of SRCL-P1 Expression in Vascular Endothelial Cells

In order to verify the expression and localization of hSRCL-P1 in tissues, fluorescent immunostaining was performed in accordance with the manipulation below using paraffin embedded sections derived from healthy human and mouse heart (Novagen Co.).

Slides with the paraffin embedded section was immersed 3 times in xylene at room temperature for 10 minutes in a stain tray to effect the paraffin removal treatment. Thereafter, the slides were sequentially immersed in 100%-90%-80%-70%-ethanol at room temperature for 10 minutes each, and into PBS (−) solution for 10 minutes for achieving the hydration treatment.

Next, the slides were immersed in a solution of PBS (−) containing 3% hydrogen peroxide in order to suppress the peroxidase activity that intrinsically exists on the tissue section at room temperature for 10 minutes. Thereafter, blocking was carried out by immersing the slide in Blocking Ace (Dainippon Pharmaceutical Co., Ltd.) at room temperature for 1 hour.

Next, 100 µl of an anti-hSRCL-P1 rabbit polyclonal antibody (IgG fraction, 100 µg/ml) as a primary antibody was applied on the tissue section in a humid box, and subjected to a reaction for 30 minutes. The primary antibody washed three times by immersing into a washing solution (Tris-HCl: pH 7.5, 0.15 M NaCl, 0.05% Tween 20) in a staining tray while shaking for 10 minutes at room temperature. Thereafter, POD (peroxidase) labeled anti-rabbit IgG sheep antibody (Boeringer Mannheim Co., Ltd.) as a secondary antibody was reacted in a similar manner to the primary antibody at a concentration of 5 U/ml, followed by washes. Then, Biotinyl Tyramide Amplification Reagent (NEN (trade name), manufactured by Life Science Products Co.) was applied to the slide, and the reaction was allowed at room temperature for 10 minutes, followed by similar washes to the procedure for the primary antibody. Avidin Alexa Fluor (trade name) 488 conjugate (manufactured by Molecular Probes Co.) of 1 mg/ml was diluted to 100-folds in a solution of PBS (−), and 100 μl of the resulting solution was applied to the tissue section on the slide in the humid box at room temperature, and subjected to a reaction for 30 minutes, followed by similar washes to the procedure for the primary antibody. Thereafter, Slow Fade Light Antifade Kit (Molecular Probes CO.) was used for the mounting to give a sample for the observation with a fluorescence microscope (Nikon Co.). In addition, a slide for the negative control was prepared in a similar manner except that normal rabbit serum was used for the reaction instead of the primary antibody.

Consequently, stained images were observed in heart vascular endothelial cells for both of A: healthy human and B: mouse as shown in FIG. 8 (left figure each), while such stained images were not found whatever in the negative control (right figure each). Accordingly, it was verified that SRCL-P1 was expressed in vascular endothelial cells in the heart, suggesting that SRCL-P1 participates in the binding of oxidized LDL, AGE and the like onto the blood vessel wall.

EFFECT OF THE INVENTION

Because SRCL-P1 protein of the present invention has an SR structure and a collectin structure, it is believed to be a substance that exerts characteristic effects to those structures. Therefore, it can be utilized in the elucidation of mechanisms of macrophage and basic immunity; in the elucidation of mechanisms of the development of a wide variety of diseases such as arteriosclerosis, diabetic complications and Alzheimer's disease, hyper β-lipoproteinemia, hypercholesterolemia, hypertriglyceridemia, hypo α-lipoproteinemia, transplantation, atherectomy, post angiogenic restenosis, bacterial infections; in the diagnostic, prophylactic and therapeutic methods thereof; and in the development of reagents and drugs for the same.

What is claimed is:

1. An isolated and purified polypeptide comprising amino acid residues 1 to 742 of SEQ ID NO: 4.

2. An isolated and purified polypeptide according to claim 1, wherein the amino acid sequence of the polypeptide consists of amino acids 1 to 742 of SEQ ID NO: 4.

3. A method for producing the polypeptide according to claim 1 comprising:
    culturing in a medium a cell transformed with a polynucleotide that comprises a nucleotide sequence encoding the polypeptide according to claim 1 and collecting the polypeptide produced by the cells.

4. The method according to claim 3, wherein the cell is an *Escherichia coli*, an animal or an insect cell.

5. The method according to claim 3, wherein said polynucleotide is an insert in a vector, and wherein the cell is transformed with the vector.

6. A method for producing a monoclonal antibody having specificity for the polypeptide according to claim 1, wherein the method comprises:
    (a) administering the polypeptide according to claim 1 to an animal,
    (b) selecting the animal that exhibits an antibody titer,
    (c) collecting a spleen or a lymph node from the animal,
    (d) fusing antibody-producing cells contained therein with myeloma cells, and
    (e) selecting a hybridoma cell line that secretes a monoclonal antibody having specificity for the polypeptide according to claim 1.

7. A method for quantitatively determining the polypeptide according to claim 1, wherein the method comprises the steps of:
- detecting an immunological binding between the polypeptide according to claim 1 and a monoclonal antibody having specificity for said polypeptide, and
- quantifying an amount of the polypeptide based on the detected immunological binding.

8. A method of screening a drug for treating a pathological state involved in the accumulation of oxidized Low Density Lipoprotein (LDL) comprising:
- measuring binding between the polypeptide according to claim 1 and oxidized LDL in the presence and absence of a candidate drug, and
- identifying a drug for the treatment of a pathological state involved in the accumulation of oxidized LDL by comparing the binding between the polypeptide according to claim 1 and oxidized LDL in the presence and absence of a candidate drug, wherein an inhibitory ability of the candidate drug toward the binding between the polypeptide according to claim 1 and oxidized LDL identifies the candidate drug as a drug for the treatment of the pathological state.

9. A method of screening a drug for treating a pathological state involved in the binding of advanced glycation end products (AGE) to cells, comprising:
- measuring binding between the polypeptide according to claim 1 and AGE in the presence and absence of a candidate drug, and
- identifying a drug for the treatment of a pathological state involved in the binding of AGE to cells by comparing the binding in the presence and absence of a candidate drug, wherein an inhibitory ability of the candidate drug toward the binding between the polypeptide according to claim 1 and AGE identifies the candidate drug as a drug for the treatment of the pathological state.

* * * * *

SEQUENCE LISTING

```
<160> NUMBER OF SEQ ID NOS: 31

<210> SEQ ID NO 1
<211> LENGTH: 2628
<212> TYPE: DNA
<213> ORGANISM: Homo Sapiens
<220> FEATURE:
<221> NAME/KEY: CDS
<222> LOCATION: (74)..(2299)

<400> SEQUENCE: 1 gggggacga cttcctcggc tgcgcggcgc tcgcgcggag ctccccggcc ggcggtgcgt      60
ccccacggtc acc atg aaa gac gac ttc gca gag gag gag gag gtg caa     109
            Met Lys Asp Asp Phe Ala Glu Glu Glu Glu Val Gln
              1               5                   10 tcc ttc ggt tac aag cgg ttt ggt att cag gaa gga aca caa tgt acc     157
Ser Phe Gly Tyr Lys Arg Phe Gly Ile Gln Glu Gly Thr Gln Cys Thr
             15                  20                  25 aaa tgt aaa aat aac tgg gca ctg aag ttt tct atc ata tta tta tac     205
Lys Cys Lys Asn Asn Trp Ala Leu Lys Phe Ser Ile Ile Leu Leu Tyr
 30                  35                  40 att ttg tgt gcc ttg cta aca atc aca gta gcc att ttg gga tat aaa     253
Ile Leu Cys Ala Leu Leu Thr Ile Thr Val Ala Ile Leu Gly Tyr Lys
 45                  50                  55                  60 gtt gta gag aaa atg gac aat gtc aca ggt ggc atg gaa aca tct cgc     301
Val Val Glu Lys Met Asp Asn Val Thr Gly Gly Met Glu Thr Ser Arg
                 65                  70                  75 caa acc tat gat gac aag ctc aca gca gtg gaa agt gac ctg aaa aaa     349
Gln Thr Tyr Asp Asp Lys Leu Thr Ala Val Glu Ser Asp Leu Lys Lys
             80                  85                  90 tta ggt gac caa act ggg aag aaa gct atc agc acc aac tca gaa ctc     397
Leu Gly Asp Gln Thr Gly Lys Lys Ala Ile Ser Thr Asn Ser Glu Leu
         95                 100                 105
```

```
                                                            -continued tcc acc ttc aga tca gac att cta gat ctc cgt cag caa ctt cgt gag    445
Ser Thr Phe Arg Ser Asp Ile Leu Asp Leu Arg Gln Gln Leu Arg Glu
    110             115                 120 att aca gaa aaa acc agc aag aac aag gat acg ctg gag aag tta cag    493
Ile Thr Glu Lys Thr Ser Lys Asn Lys Asp Thr Leu Glu Lys Leu Gln
125             130                 135                 140 gcg agc ggg gat gct ctg gtg gac agg cag agt caa ttg aaa gaa act    541
Ala Ser Gly Asp Ala Leu Val Asp Arg Gln Ser Gln Leu Lys Glu Thr
                145                 150                 155 ttg gag aat aac tct ttc ctc atc acc act gta aac aaa acc ctc cag    589
Leu Glu Asn Asn Ser Phe Leu Ile Thr Thr Val Asn Lys Thr Leu Gln
            160                 165                 170 gcg tat aat ggc tat gtc acg aat ctg cag caa gat acc agc gtg ctc    637
Ala Tyr Asn Gly Tyr Val Thr Asn Leu Gln Gln Asp Thr Ser Val Leu
        175                 180                 185 cag ggc aat ctg cag aac caa atg tat tct cat aat gtg gtc atc atg    685
Gln Gly Asn Leu Gln Asn Gln Met Tyr Ser His Asn Val Val Ile Met
    190                 195                 200 aac ctc aac aac ctg aac ctg acc cag gtg cag cag agg aac ctc atc    733
Asn Leu Asn Asn Leu Asn Leu Thr Gln Val Gln Gln Arg Asn Leu Ile
205                 210                 215                 220 acg aat ctg cag cgg tct gtg gat gac aca agc cag gct atc cag cga    781
Thr Asn Leu Gln Arg Ser Val Asp Asp Thr Ser Gln Ala Ile Gln Arg
                225                 230                 235 atc aag aac gac ttt caa aat ctg cag cag gtt ttt ctt caa gcc aag    829
Ile Lys Asn Asp Phe Gln Asn Leu Gln Gln Val Phe Leu Gln Ala Lys
            240                 245                 250 aag gac acg gat tgg ctg aag gag aaa gtg cag agc ttg cag acg ctg    877
Lys Asp Thr Asp Trp Leu Lys Glu Lys Val Gln Ser Leu Gln Thr Leu
        255                 260                 265 gct gcc aac aac tct gcg ttg gcc aaa gcc aac aac gac acc ctg gag    925
Ala Ala Asn Asn Ser Ala Leu Ala Lys Ala Asn Asn Asp Thr Leu Glu
    270                 275                 280 gat atg aac agc cag ctc aac tca ttc aca ggt cag atg gag aac atc    973
Asp Met Asn Ser Gln Leu Asn Ser Phe Thr Gly Gln Met Glu Asn Ile
285                 290                 295                 300 acc act atc tct caa gcc aac gag cag aac ctg aaa gac ctg cag gac   1021
Thr Thr Ile Ser Gln Ala Asn Glu Gln Asn Leu Lys Asp Leu Gln Asp
                305                 310                 315 tta cac aaa gat gca gag aat aga aca gcc atc aag ttc aac caa ctg   1069
Leu His Lys Asp Ala Glu Asn Arg Thr Ala Ile Lys Phe Asn Gln Leu
            320                 325                 330 gag gaa cgc ttc cag ctc ttt gag acg gat att gtg aac atc att agc   1117
Glu Glu Arg Phe Gln Leu Phe Glu Thr Asp Ile Val Asn Ile Ile Ser
        335                 340                 345 aat atc agt tac aca gcc cac cac ctg cgg acg ctg acc agc aat cta   1165
Asn Ile Ser Tyr Thr Ala His His Leu Arg Thr Leu Thr Ser Asn Leu
    350                 355                 360 aat gaa gtc agg acc act tgc aca gat acc ctt acc aaa cac aca gat   1213
Asn Glu Val Arg Thr Thr Cys Thr Asp Thr Leu Thr Lys His Thr Asp
365                 370                 375                 380 gat ctg acc tcc ttg aat aat acc ctg gcc aac atc cgt ttg gat tct   1261
Asp Leu Thr Ser Leu Asn Asn Thr Leu Ala Asn Ile Arg Leu Asp Ser
                385                 390                 395 gtt tct ctc agg atg caa caa gat ttg atg agg tcg agg tta gac act   1309
Val Ser Leu Arg Met Gln Gln Asp Leu Met Arg Ser Arg Leu Asp Thr
            400                 405                 410 gaa gta gcc aac tta tca gtg att atg gaa gaa atg aag cta gta gac   1357
Glu Val Ala Asn Leu Ser Val Ile Met Glu Glu Met Lys Leu Val Asp
        415                 420                 425
```

```
tcc aag cat ggt cag ctc atc aag aat ttt aca ata cta caa ggt cca    1405
Ser Lys His Gly Gln Leu Ile Lys Asn Phe Thr Ile Leu Gln Gly Pro
    430                 435                 440 ccg ggc ccc agg ggt cca aga ggt gac aga gga tcc cag gga ccc cct    1453
Pro Gly Pro Arg Gly Pro Arg Gly Asp Arg Gly Ser Gln Gly Pro Pro
445                 450                 455                 460 ggc cca act ggc aac aag gga cag aaa gga gag aag ggg gag cct gga    1501
Gly Pro Thr Gly Asn Lys Gly Gln Lys Gly Glu Lys Gly Glu Pro Gly
                465                 470                 475 cca cct ggc cct gcg ggt gag aga ggc cca att gga cca gct ggt ccc    1549
Pro Pro Gly Pro Ala Gly Glu Arg Gly Pro Ile Gly Pro Ala Gly Pro
            480                 485                 490 ccc gga gag cgt ggc ggc aaa gga tct aaa ggc tcc cag ggc ccc aaa    1597
Pro Gly Glu Arg Gly Gly Lys Gly Ser Lys Gly Ser Gln Gly Pro Lys
        495                 500                 505 ggc tcc cgt ggt tcc cct ggg aag ccc ggc cct cag ggc ccc agt ggg    1645
Gly Ser Arg Gly Ser Pro Gly Lys Pro Gly Pro Gln Gly Pro Ser Gly
    510                 515                 520 gac cca ggc ccc ccg ggc cca cca ggc aaa gag gga ctc ccc ggc cct    1693
Asp Pro Gly Pro Pro Gly Pro Pro Gly Lys Glu Gly Leu Pro Gly Pro
525                 530                 535                 540 cag ggc cct cct ggc ttc cag gga ctt cag ggc acc gtt ggg gag cct    1741
Gln Gly Pro Pro Gly Phe Gln Gly Leu Gln Gly Thr Val Gly Glu Pro
                545                 550                 555 ggg gtg cct gga cct cgg gga ctg cca ggc ttg cct ggg gta cca ggc    1789
Gly Val Pro Gly Pro Arg Gly Leu Pro Gly Leu Pro Gly Val Pro Gly
            560                 565                 570 atg cca ggc ccc aag ggc ccc ccc ggc cct cct ggc cca tca gga gcg    1837
Met Pro Gly Pro Lys Gly Pro Pro Gly Pro Pro Gly Pro Ser Gly Ala
        575                 580                 585 gtg gtg ccc ctg gcc ctg cag aat gag cca acc ccg gca ccg gag gac    1885
Val Val Pro Leu Ala Leu Gln Asn Glu Pro Thr Pro Ala Pro Glu Asp
    590                 595                 600 aat ggc tgc ccg cct cac tgg aag aac ttc aca gac aaa tgc tac tat    1933
Asn Gly Cys Pro Pro His Trp Lys Asn Phe Thr Asp Lys Cys Tyr Tyr
605                 610                 615                 620 ttt tca gtt gag aaa gaa att ttt gag gat gca aag ctt ttc tgt gaa    1981
Phe Ser Val Glu Lys Glu Ile Phe Glu Asp Ala Lys Leu Phe Cys Glu
                625                 630                 635 gac aag tct tca cat ctt gtt ttc ata aac act aga gag gaa cag caa    2029
Asp Lys Ser Ser His Leu Val Phe Ile Asn Thr Arg Glu Glu Gln Gln
            640                 645                 650 tgg ata aaa aaa cag atg gta ggg aga gag agc cac tgg atc ggc ctc    2077
Trp Ile Lys Lys Gln Met Val Gly Arg Glu Ser His Trp Ile Gly Leu
        655                 660                 665 aca gac tca gag cgt gaa aat gaa tgg aag tgg ctg gat ggg aca tct    2125
Thr Asp Ser Glu Arg Glu Asn Glu Trp Lys Trp Leu Asp Gly Thr Ser
    670                 675                 680 cca gac tac aaa aat tgg aaa gct gga cag ccg gat aac tgg ggt cat    2173
Pro Asp Tyr Lys Asn Trp Lys Ala Gly Gln Pro Asp Asn Trp Gly His
685                 690                 695                 700 ggc cat ggg cca gga gaa gac tgt gct ggg ttg att tat gct ggg cag    2221
Gly His Gly Pro Gly Glu Asp Cys Ala Gly Leu Ile Tyr Ala Gly Gln
                705                 710                 715 tgg aac gat ttc caa tgt gaa gac gtc aat aac ttc att tgc gaa aaa    2269
Trp Asn Asp Phe Gln Cys Glu Asp Val Asn Asn Phe Ile Cys Glu Lys
            720                 725                 730 gac agg gag aca gta ctg tca tct gca tta taacggactg tgatgggatc      2319
Asp Arg Glu Thr Val Leu Ser Ser Ala Leu
```

```
                735                 740
acatgagcaa attttcagct ctcaaaggca aaggacactc ctttctaatt gcatcacctt    2379
ctcatcagat tgaaaaaaaa aaaagcactg aaaaccaatt actgaaaaaa aattgacagc    2439
tagtgttttt taccatccgt cattacccaa agacttggga actaaaatgt tccccagggt    2499
gatatgctga ttttcattgt gcacatggac tgaatcacat agattctcct ccgtcagtaa    2559
ccgtgcgatt atacaaatta tgtcttccaa agtatggaac actccaatca gaaaaggtt     2619 atcatcccg                                                            2628

<210> SEQ ID NO 2
<211> LENGTH: 742
<212> TYPE: PRT
<213> ORGANISM: Homo Sapiens
<220> FEATURE:
<223> OTHER INFORMATION: Deduced Amino Acid Sequence of Novel Human
      Scavenger Receptor from Nucleotide Sequence.

<400> SEQUENCE: 2

Met Lys Asp Asp Phe Ala Glu Glu Glu Val Gln Ser Phe Gly Tyr
 1               5                   10                  15

Lys Arg Phe Gly Ile Gln Glu Gly Thr Gln Cys Thr Lys Cys Lys Asn
                20                  25                  30

Asn Trp Ala Leu Lys Phe Ser Ile Ile Leu Leu Tyr Ile Leu Cys Ala
            35                  40                  45

Leu Leu Thr Ile Thr Val Ala Ile Leu Gly Tyr Lys Val Val Glu Lys
        50                  55                  60

Met Asp Asn Val Thr Gly Gly Met Glu Thr Ser Arg Gln Thr Tyr Asp
65                  70                  75                  80

Asp Lys Leu Thr Ala Val Glu Ser Asp Leu Lys Lys Leu Gly Asp Gln
                85                  90                  95

Thr Gly Lys Lys Ala Ile Ser Thr Asn Ser Glu Leu Ser Thr Phe Arg
            100                 105                 110

Ser Asp Ile Leu Asp Leu Arg Gln Gln Leu Arg Glu Ile Thr Glu Lys
        115                 120                 125

Thr Ser Lys Asn Lys Asp Thr Leu Glu Lys Leu Gln Ala Ser Gly Asp
    130                 135                 140

Ala Leu Val Asp Arg Gln Ser Gln Leu Lys Glu Thr Leu Glu Asn Asn
145                 150                 155                 160

Ser Phe Leu Ile Thr Thr Val Asn Lys Thr Leu Gln Ala Tyr Asn Gly
                165                 170                 175

Tyr Val Thr Asn Leu Gln Gln Asp Thr Ser Val Leu Gln Gly Asn Leu
            180                 185                 190

Gln Asn Gln Met Tyr Ser His Asn Val Val Ile Met Asn Leu Asn Asn
        195                 200                 205

Leu Asn Leu Thr Gln Val Gln Gln Arg Asn Leu Ile Thr Asn Leu Gln
    210                 215                 220

Arg Ser Val Asp Asp Thr Ser Gln Ala Ile Gln Arg Ile Lys Asn Asp
225                 230                 235                 240

Phe Gln Asn Leu Gln Gln Val Phe Leu Gln Ala Lys Lys Asp Thr Asp
                245                 250                 255

Trp Leu Lys Glu Lys Val Gln Ser Leu Gln Thr Leu Ala Ala Asn Asn
            260                 265                 270

Ser Ala Leu Ala Lys Ala Asn Asn Asp Thr Leu Glu Asp Met Asn Ser
        275                 280                 285
```

-continued

```
Gln Leu Asn Ser Phe Thr Gly Gln Met Glu Asn Ile Thr Thr Ile Ser
    290                 295                 300
Gln Ala Asn Glu Gln Asn Leu Lys Asp Leu Gln Asp Leu His Lys Asp
305                 310                 315                 320
Ala Glu Asn Arg Thr Ala Ile Lys Phe Asn Gln Leu Glu Glu Arg Phe
                325                 330                 335
Gln Leu Phe Glu Thr Asp Ile Val Asn Ile Ile Ser Asn Ile Ser Tyr
            340                 345                 350
Thr Ala His His Leu Arg Thr Leu Thr Ser Asn Leu Asn Glu Val Arg
        355                 360                 365
Thr Thr Cys Thr Asp Thr Leu Thr Lys His Thr Asp Asp Leu Thr Ser
370                 375                 380
Leu Asn Asn Thr Leu Ala Asn Ile Arg Leu Asp Ser Val Ser Leu Arg
385                 390                 395                 400
Met Gln Gln Asp Leu Met Arg Ser Arg Leu Asp Thr Glu Val Ala Asn
                405                 410                 415
Leu Ser Val Ile Met Glu Glu Met Lys Leu Val Asp Ser Lys His Gly
            420                 425                 430
Gln Leu Ile Lys Asn Phe Thr Ile Leu Gln Gly Pro Pro Gly Pro Arg
        435                 440                 445
Gly Pro Arg Gly Asp Arg Gly Ser Gln Gly Pro Pro Gly Pro Thr Gly
450                 455                 460
Asn Lys Gly Gln Lys Gly Glu Lys Gly Glu Pro Gly Pro Pro Gly Pro
465                 470                 475                 480
Ala Gly Glu Arg Gly Pro Ile Gly Pro Ala Gly Pro Pro Gly Glu Arg
                485                 490                 495
Gly Gly Lys Gly Ser Lys Gly Ser Gln Gly Pro Lys Gly Ser Arg Gly
            500                 505                 510
Ser Pro Gly Lys Pro Gly Pro Gln Gly Pro Ser Gly Asp Pro Gly Pro
        515                 520                 525
Pro Gly Pro Pro Gly Lys Glu Gly Leu Pro Gly Pro Gln Gly Pro Pro
530                 535                 540
Gly Phe Gln Gly Leu Gln Gly Thr Val Gly Glu Pro Gly Val Pro Gly
545                 550                 555                 560
Pro Arg Gly Leu Pro Gly Leu Pro Gly Val Pro Gly Met Pro Gly Pro
                565                 570                 575
Lys Gly Pro Pro Gly Pro Pro Gly Pro Ser Gly Ala Val Val Pro Leu
            580                 585                 590
Ala Leu Gln Asn Glu Pro Thr Pro Ala Pro Glu Asp Asn Gly Cys Pro
        595                 600                 605
Pro His Trp Lys Asn Phe Thr Asp Lys Cys Tyr Tyr Phe Ser Val Glu
610                 615                 620
Lys Glu Ile Phe Glu Asp Ala Lys Leu Phe Cys Glu Asp Lys Ser Ser
625                 630                 635                 640
His Leu Val Phe Ile Asn Thr Arg Glu Glu Gln Gln Trp Ile Lys Lys
                645                 650                 655
Gln Met Val Gly Arg Glu Ser His Trp Ile Gly Leu Thr Asp Ser Glu
            660                 665                 670
Arg Glu Asn Glu Trp Lys Trp Leu Asp Gly Thr Ser Pro Asp Tyr Lys
        675                 680                 685
Asn Trp Lys Ala Gly Gln Pro Asp Asn Trp Gly His Gly His Gly Pro
690                 695                 700
Gly Glu Asp Cys Ala Gly Leu Ile Tyr Ala Gly Gln Trp Asn Asp Phe
```

| | | | |
|---|---|---|---|
| 705 | 710 | 715 | 720 |

Gln Cys Glu Asp Val Asn Asn Phe Ile Cys Glu Lys Asp Arg Glu Thr
                         725                      730                     735

Val Leu Ser Ser Ala Leu
            740

<210> SEQ ID NO 3
<211> LENGTH: 2637
<212> TYPE: DNA
<213> ORGANISM: Mouse
<220> FEATURE:
<221> NAME/KEY: CDS
<222> LOCATION: (92)..(2317)

<400> SEQUENCE: 3

```
gacgctagga ctggaacgct gaaggctgcc atgggcgtgc agtgagagac actggtacga      60
cttctccggg cggagcgtgt cctcagtcac c atg aaa gac gac ttt gca gag       112
                                   Met Lys Asp Asp Phe Ala Glu
                                     1               5 gaa gag gag gtg cag tcc ttc ggt tac aag agg ttt ggt att cag gag      160
Glu Glu Glu Val Gln Ser Phe Gly Tyr Lys Arg Phe Gly Ile Gln Glu
         10                  15                  20 ggg aca cag tgt acc aaa tgt aaa aat aac tgg gca ctg aag ttt tcg      208
Gly Thr Gln Cys Thr Lys Cys Lys Asn Asn Trp Ala Leu Lys Phe Ser
     25                  30                  35 att gta tta tta tac att ctg tgt gcc tta ctg acc atc aca gta gcc      256
Ile Val Leu Leu Tyr Ile Leu Cys Ala Leu Leu Thr Ile Thr Val Ala
 40                  45                  50                  55 att ttg gga tat aaa gtt gta gag aaa atg gac aat gtc aca gat ggc      304
Ile Leu Gly Tyr Lys Val Val Glu Lys Met Asp Asn Val Thr Asp Gly
                 60                  65                  70 atg gag aca tct cac cag act tat gac aac aaa ctc act gct gtg gaa      352
Met Glu Thr Ser His Gln Thr Tyr Asp Asn Lys Leu Thr Ala Val Glu
             75                  80                  85 agt gac ctg aag aaa tta ggg gat caa gct ggg aag aaa gct cta agt      400
Ser Asp Leu Lys Lys Leu Gly Asp Gln Ala Gly Lys Lys Ala Leu Ser
         90                  95                 100 acc aac tct gag ctt tct acc ttc aga tca gat att ctg gat ctc cgt      448
Thr Asn Ser Glu Leu Ser Thr Phe Arg Ser Asp Ile Leu Asp Leu Arg
    105                 110                 115 caa caa ctt cag gag atc aca gaa aaa acc agc aag aac aaa gat acg      496
Gln Gln Leu Gln Glu Ile Thr Glu Lys Thr Ser Lys Asn Lys Asp Thr
120                 125                 130                 135 ctg gag aag ttg caa gca aat ggg gac tca ttg gtt gat agg cag agt      544
Leu Glu Lys Leu Gln Ala Asn Gly Asp Ser Leu Val Asp Arg Gln Ser
                140                 145                 150 cag ctg aag gaa act ctg cag aat aat tct ttc ctc att acc acc gtc      592
Gln Leu Lys Glu Thr Leu Gln Asn Asn Ser Phe Leu Ile Thr Thr Val
            155                 160                 165 aac aaa aca ctc cag gca tat aat ggc tat gtc aca aat ctg caa caa      640
Asn Lys Thr Leu Gln Ala Tyr Asn Gly Tyr Val Thr Asn Leu Gln Gln
        170                 175                 180 gat act agt gtg ctc cag ggc aat ctg cag agc caa atg tat tct cag      688
Asp Thr Ser Val Leu Gln Gly Asn Leu Gln Ser Gln Met Tyr Ser Gln
    185                 190                 195 agc gtg gtt atc atg aac ctc aac aac ctg aac cta acc cag gtt cag      736
Ser Val Val Ile Met Asn Leu Asn Asn Leu Asn Leu Thr Gln Val Gln
200                 205                 210                 215 cag agg aac ctt atc tca aat ctg cag cag tct gtg gat gac aca agc      784
Gln Arg Asn Leu Ile Ser Asn Leu Gln Gln Ser Val Asp Asp Thr Ser
```

-continued

```
                  220                 225                 230
ctg gcc atc cag cga att aag aat gat ttc caa aat ctg cag cag gtt      832
Leu Ala Ile Gln Arg Ile Lys Asn Asp Phe Gln Asn Leu Gln Gln Val
            235                 240                 245 ttc ctt caa gcc aag aag gac acc gat tgg cta aag gaa aaa gta cag      880
Phe Leu Gln Ala Lys Lys Asp Thr Asp Trp Leu Lys Glu Lys Val Gln
            250                 255                 260 agc ttg cag aca ttg gct gcc aac aac tct gcc ctg gcc aaa gcc aac      928
Ser Leu Gln Thr Leu Ala Ala Asn Asn Ser Ala Leu Ala Lys Ala Asn
            265                 270                 275 aat gac acc cta gag gat atg aat agc cag ctc agc tca ttc aca ggt      976
Asn Asp Thr Leu Glu Asp Met Asn Ser Gln Leu Ser Ser Phe Thr Gly
280                 285                 290                 295 cag atg gac aac att acc act atc tca cag gcc aac gag cag agc ctg     1024
Gln Met Asp Asn Ile Thr Thr Ile Ser Gln Ala Asn Glu Gln Ser Leu
                300                 305                 310 aaa gac ctt cag gac tta cac aag gat aca gaa aat aga aca gct gtc     1072
Lys Asp Leu Gln Asp Leu His Lys Asp Thr Glu Asn Arg Thr Ala Val
            315                 320                 325 aag ttc agc caa ctt gag gaa cgc ttc cag gtc ttt gag aca gat att     1120
Lys Phe Ser Gln Leu Glu Glu Arg Phe Gln Val Phe Glu Thr Asp Ile
            330                 335                 340 gtg aac atc att agc aac atc agc tac aca gcc cat cac ctg agg aca     1168
Val Asn Ile Ile Ser Asn Ile Ser Tyr Thr Ala His His Leu Arg Thr
345                 350                 355 ctg acc agc aat ctg aat gat gtt agg acc aca tgc aca gac acc ttg     1216
Leu Thr Ser Asn Leu Asn Asp Val Arg Thr Thr Cys Thr Asp Thr Leu
360                 365                 370                 375 acc aga cac acg gat gac ctg acc tcc ttg aat aac aca cta gtc aac     1264
Thr Arg His Thr Asp Asp Leu Thr Ser Leu Asn Asn Thr Leu Val Asn
                380                 385                 390 atc cgc ttg gat tct att tct ctc agg atg cag caa gac atg atg agg     1312
Ile Arg Leu Asp Ser Ile Ser Leu Arg Met Gln Gln Asp Met Met Arg
            395                 400                 405 tca aag tta gac act gaa gtg gcc aac tta tca gtg gtt atg gaa gag     1360
Ser Lys Leu Asp Thr Glu Val Ala Asn Leu Ser Val Val Met Glu Glu
            410                 415                 420 atg aaa ctg gtt gac tcc aag cac ggt cag ctc atc aag aac ttt acc     1408
Met Lys Leu Val Asp Ser Lys His Gly Gln Leu Ile Lys Asn Phe Thr
425                 430                 435 att cta caa ggt cct cct ggc ccc aga ggt cca aaa ggt gac aga gga     1456
Ile Leu Gln Gly Pro Pro Gly Pro Arg Gly Pro Lys Gly Asp Arg Gly
440                 445                 450                 455 tct cag gga cca cct ggt cca act ggc aac aag gga cag aaa gga gag     1504
Ser Gln Gly Pro Pro Gly Pro Thr Gly Asn Lys Gly Gln Lys Gly Glu
                460                 465                 470 aag gga gag cct ggt cca cct ggc cct gcg ggt gag agg ggc aca att     1552
Lys Gly Glu Pro Gly Pro Pro Gly Pro Ala Gly Glu Arg Gly Thr Ile
            475                 480                 485 gga cca gtc ggc cct cct gga gag cgt ggc agc aaa gga tcc aaa ggc     1600
Gly Pro Val Gly Pro Pro Gly Glu Arg Gly Ser Lys Gly Ser Lys Gly
            490                 495                 500 tca cag ggt ccc aaa gga tct cgt ggg tcc cca ggg aag cct ggc cct     1648
Ser Gln Gly Pro Lys Gly Ser Arg Gly Ser Pro Gly Lys Pro Gly Pro
505                 510                 515 caa gga cct agt ggg gac cca gga cca cca ggt cca cca ggc aag gat     1696
Gln Gly Pro Ser Gly Asp Pro Gly Pro Pro Gly Pro Pro Gly Lys Asp
520                 525                 530                 535 gga ctc cct ggc cct cag ggc cct cct ggc ttc cag gga cta cag ggc     1744
Gly Leu Pro Gly Pro Gln Gly Pro Pro Gly Phe Gln Gly Leu Gln Gly
```

```
Gly Leu Pro Gly Pro Gln Gly Pro Gly Phe Gln Gly Leu Gln Gly
            540                 545                 550 act gtg ggt gag cct gga gta cct gga cct cgg ggg ttg cca ggc ttg     1792
Thr Val Gly Glu Pro Gly Val Pro Gly Pro Arg Gly Leu Pro Gly Leu
            555                 560                 565 cca ggg gtg cca ggc atg cct ggg cct aag gga cca cct ggc cct cca     1840
Pro Gly Val Pro Gly Met Pro Gly Pro Lys Gly Pro Pro Gly Pro Pro
            570                 575                 580 ggc ccc tca gga gca atg gag cca ttg gct ctg cag aat gaa cca acc     1888
Gly Pro Ser Gly Ala Met Glu Pro Leu Ala Leu Gln Asn Glu Pro Thr
        585                 590                 595 cca gca tca gag gtc aac gga tgt ccg cct cac tgg aag aac ttc aca     1936
Pro Ala Ser Glu Val Asn Gly Cys Pro Pro His Trp Lys Asn Phe Thr
600                 605                 610                 615 gat aaa tgc tac tat ttt tca ttg gaa aaa gaa att ttt gaa gat gct     1984
Asp Lys Cys Tyr Tyr Phe Ser Leu Glu Lys Glu Ile Phe Glu Asp Ala
                620                 625                 630 aag ctt ttc tgt gaa gac aaa tct tcc cat ctc gtt ttc ata aac tca     2032
Lys Leu Phe Cys Glu Asp Lys Ser Ser His Leu Val Phe Ile Asn Ser
            635                 640                 645 aga gaa gaa cag caa tgg ata aaa aag cat acc gtg ggg aga gaa agc     2080
Arg Glu Glu Gln Gln Trp Ile Lys Lys His Thr Val Gly Arg Glu Ser
        650                 655                 660 cat tgg atc ggc ctc aca gac tca gaa cag gaa agc gaa tgg aag tgg     2128
His Trp Ile Gly Leu Thr Asp Ser Glu Gln Glu Ser Glu Trp Lys Trp
    665                 670                 675 cta gac ggg tca cct gtt gat tac aaa aac tgg aaa gct gga caa cca     2176
Leu Asp Gly Ser Pro Val Asp Tyr Lys Asn Trp Lys Ala Gly Gln Pro
680                 685                 690                 695 gat aac tgg ggc agt ggc cat ggg cca gga gaa gac tgt gct ggc ttg     2224
Asp Asn Trp Gly Ser Gly His Gly Pro Gly Glu Asp Cys Ala Gly Leu
                700                 705                 710 att tac gca gga cag tgg aat gac ttc cag tgt gat gaa atc aat aac     2272
Ile Tyr Ala Gly Gln Trp Asn Asp Phe Gln Cys Asp Glu Ile Asn Asn
            715                 720                 725 ttc att tgt gag aag gaa agg gag gca gta cca tca tcc ata tta         2317
Phe Ile Cys Glu Lys Glu Arg Glu Ala Val Pro Ser Ser Ile Leu
        730                 735                 740 taacagcatg atataatagc agaaacatat tttctgatgc ctctgaaagc cgaagaatgc   2377 tcgttttga ttccatcact tctcaccaga ttgaatggaa aaagctctga aaagtagtta    2437
ttcaaaataa atggacacct actgcacaat aacccaagga ctaggggct aaaatgctcc    2497 cccaagttga tatattgatt tccagtgtac aaatggactg aatcgcatag attttctcag   2557
ccattaacca tagaatttat gcaaagtata tctttccaaa tatggaatgc tccaatcaga   2617
aaaagccaaa aaaaaaaaa                                                2637
```

<210> SEQ ID NO 4
<211> LENGTH: 742
<212> TYPE: PRT
<213> ORGANISM: Mouse
<220> FEATURE:
<223> OTHER INFORMATION: Deduced Amino Acid Sequence of Novel Mouse
      Scavenger Receptor from Nucleotide Sequence.

<400> SEQUENCE: 4

```
Met Lys Asp Asp Phe Ala Glu Glu Glu Val Gln Ser Phe Gly Tyr
 1               5                  10                  15

Lys Arg Phe Gly Ile Gln Glu Gly Thr Gln Cys Thr Lys Cys Lys Asn
            20                  25                  30
```

```
Asn Trp Ala Leu Lys Phe Ser Ile Val Leu Leu Tyr Ile Leu Cys Ala
         35                  40                  45

Leu Leu Thr Ile Thr Val Ala Ile Leu Gly Tyr Lys Val Val Glu Lys
     50                  55                  60

Met Asp Asn Val Thr Asp Gly Met Glu Thr Ser His Gln Thr Tyr Asp
 65                  70                  75                  80

Asn Lys Leu Thr Ala Val Glu Ser Asp Leu Lys Lys Leu Gly Asp Gln
                 85                  90                  95

Ala Gly Lys Lys Ala Leu Ser Thr Asn Ser Glu Leu Ser Thr Phe Arg
            100                 105                 110

Ser Asp Ile Leu Asp Leu Arg Gln Gln Leu Gln Glu Ile Thr Glu Lys
        115                 120                 125

Thr Ser Lys Asn Lys Asp Thr Leu Glu Lys Leu Gln Ala Asn Gly Asp
    130                 135                 140

Ser Leu Val Asp Arg Gln Ser Gln Leu Lys Glu Thr Leu Gln Asn Asn
145                 150                 155                 160

Ser Phe Leu Ile Thr Thr Val Asn Lys Thr Leu Gln Ala Tyr Asn Gly
                165                 170                 175

Tyr Val Thr Asn Leu Gln Gln Asp Thr Ser Val Leu Gln Gly Asn Leu
            180                 185                 190

Gln Ser Gln Met Tyr Ser Gln Ser Val Val Ile Met Asn Leu Asn Asn
        195                 200                 205

Leu Asn Leu Thr Gln Val Gln Gln Arg Asn Leu Ile Ser Asn Leu Gln
    210                 215                 220

Gln Ser Val Asp Asp Thr Ser Leu Ala Ile Gln Arg Ile Lys Asn Asp
225                 230                 235                 240

Phe Gln Asn Leu Gln Gln Val Phe Leu Gln Ala Lys Lys Asp Thr Asp
                245                 250                 255

Trp Leu Lys Glu Lys Val Gln Ser Leu Gln Thr Leu Ala Ala Asn Asn
            260                 265                 270

Ser Ala Leu Ala Lys Ala Asn Asn Asp Thr Leu Glu Asp Met Asn Ser
    275                 280                 285

Gln Leu Ser Ser Phe Thr Gly Gln Met Asp Asn Ile Thr Thr Ile Ser
    290                 295                 300

Gln Ala Asn Glu Gln Ser Leu Lys Asp Leu Gln Asp Leu His Lys Asp
305                 310                 315                 320

Thr Glu Asn Arg Thr Ala Val Lys Phe Ser Gln Leu Glu Glu Arg Phe
                325                 330                 335

Gln Val Phe Glu Thr Asp Ile Val Asn Ile Ile Ser Asn Ile Ser Tyr
            340                 345                 350

Thr Ala His His Leu Arg Thr Leu Thr Ser Asn Leu Asn Asp Val Arg
    355                 360                 365

Thr Thr Cys Thr Asp Thr Leu Thr Arg His Thr Asp Asp Leu Thr Ser
    370                 375                 380

Leu Asn Asn Thr Leu Val Asn Ile Arg Leu Asp Ser Ile Ser Leu Arg
385                 390                 395                 400

Met Gln Gln Asp Met Met Arg Ser Lys Leu Asp Thr Glu Val Ala Asn
                405                 410                 415

Leu Ser Val Val Met Glu Glu Met Lys Leu Val Asp Ser Lys His Gly
            420                 425                 430

Gln Leu Ile Lys Asn Phe Thr Ile Leu Gln Gly Pro Pro Gly Pro Arg
    435                 440                 445
```

-continued

```
Gly Pro Lys Gly Asp Arg Gly Ser Gln Gly Pro Pro Gly Pro Thr Gly
            450                 455                 460
Asn Lys Gly Gln Lys Gly Glu Lys Gly Glu Pro Gly Pro Pro Gly Pro
465                 470                 475                 480
Ala Gly Glu Arg Gly Thr Ile Gly Pro Val Gly Pro Pro Gly Glu Arg
                485                 490                 495
Gly Ser Lys Gly Ser Lys Gly Ser Gln Gly Pro Lys Gly Ser Arg Gly
                500                 505                 510
Ser Pro Gly Lys Pro Gly Pro Gln Gly Pro Ser Gly Asp Pro Gly Pro
                515                 520                 525
Pro Gly Pro Pro Gly Lys Asp Gly Leu Pro Gly Pro Gln Gly Pro Pro
            530                 535                 540
Gly Phe Gln Gly Leu Gln Gly Thr Val Gly Glu Pro Gly Val Pro Gly
545                 550                 555                 560
Pro Arg Gly Leu Pro Gly Leu Pro Gly Val Pro Gly Met Pro Gly Pro
                565                 570                 575
Lys Gly Pro Pro Gly Pro Gly Pro Ser Gly Ala Met Glu Pro Leu
                580                 585                 590
Ala Leu Gln Asn Glu Pro Thr Pro Ala Ser Glu Val Asn Gly Cys Pro
            595                 600                 605
Pro His Trp Lys Asn Phe Thr Asp Lys Cys Tyr Tyr Phe Ser Leu Glu
            610                 615                 620
Lys Glu Ile Phe Glu Asp Ala Lys Leu Phe Cys Glu Asp Lys Ser Ser
625                 630                 635                 640
His Leu Val Phe Ile Asn Ser Arg Glu Glu Gln Trp Ile Lys Lys
                645                 650                 655
His Thr Val Gly Arg Glu Ser His Trp Ile Gly Leu Thr Asp Ser Glu
                660                 665                 670
Gln Glu Ser Glu Trp Lys Trp Leu Asp Gly Ser Pro Val Asp Tyr Lys
                675                 680                 685
Asn Trp Lys Ala Gly Gln Pro Asp Asn Trp Gly Ser Gly His Gly Pro
            690                 695                 700
Gly Glu Asp Cys Ala Gly Leu Ile Tyr Ala Gly Gln Trp Asn Asp Phe
705                 710                 715                 720
Gln Cys Asp Glu Ile Asn Asn Phe Ile Cys Glu Lys Glu Arg Glu Ala
                725                 730                 735
Val Pro Ser Ser Ile Leu
            740
```

<210> SEQ ID NO 5
<211> LENGTH: 27
<212> TYPE: PRT
<213> ORGANISM: Artificial Sequence
<220> FEATURE:
<223> OTHER INFORMATION: Consensus sequence of three collectins which were reportedheretofore.

<400> SEQUENCE: 5

```
Glu Asp Cys Val Leu Leu Leu Lys Asn Gly Gln Trp Asn Asp Val Pro
 1               5                  10                  15
Cys Ser Thr Ser His Leu Ala Val Cys Glu Phe
            20                  25
```

<210> SEQ ID NO 6
<211> LENGTH: 27
<212> TYPE: PRT
<213> ORGANISM: Artificial Sequence

```
<220> FEATURE:
<223> OTHER INFORMATION: Modified Consensus Sequence of collectins
      Hybridizable with Novel Collectin.

<400> SEQUENCE: 6

```
<213> ORGANISM: Artificial Sequence
<220> FEATURE:
<223> OTHER INFORMATION: Sequence of a lambda gt11 Forward Primer for
      Sequencing.

<400> SEQUENCE: 12
ggtggcgacg actcctggag cccg                                              24

<210> SEQ ID NO 13
<211> LENGTH: 21
<212> TYPE: DNA
<213> ORGANISM: Artificial Sequence
<220> FEATURE:
<223> OTHER INFORMATION: Sequence of a Primer for Screening a Novel
      Collectin.

<400> SEQUENCE: 13
cgtgaaaatg aatggaagtg g                                                 21

<210> SEQ ID NO 14
<211> LENGTH: 21
<212> TYPE: DNA
<213> ORGANISM: Artificial Sequence
<220> FEATURE:
<223> OTHER INFORMATION: Sequence of a Primer for Screening a Novel
      Collectin.

<400> SEQUENCE: 14
ttttatccat tgctgttcct c                                                 21

<210> SEQ ID NO 15
<211> LENGTH: 21
<212> TYPE: DNA
<213> ORGANISM: Artificial Sequence
<220> FEATURE:
<223> OTHER INFORMATION: Sequence of a Primer for Sequencing a Novel
      Collectin.

<400> SEQUENCE: 15
ctggcagtcc ccgaggtcca g                                                 21

<210> SEQ ID NO 16
<211> LENGTH: 21
<212> TYPE: DNA
<213> ORGANISM: Artificial Sequence
<220> FEATURE:
<223> OTHER INFORMATION: Sequence of a Primer for Sequencing a Novel
      Collectin.

<400> SEQUENCE: 16
gctggtcccc ccggagagcg t                                                 21

<210> SEQ ID NO 17
<211> LENGTH: 21
<212> TYPE: DNA
<213> ORGANISM: Artificial Sequence
<220> FEATURE:
<223> OTHER INFORMATION: Sequence of a 1RC2 Primer for Cap Site
      Sequencing.

<400> SEQUENCE: 17
caaggtacgc cacagcgtat g                                                 21

<210> SEQ ID NO 18
<211> LENGTH: 20
<212> TYPE: DNA
<213> ORGANISM: Artificial Sequence
```

<220> FEATURE:
<223> OTHER INFORMATION: Sequence of a Synthetic TGP1 Primer for Cap
      Site Sequencing.

<400> SEQUENCE: 18
tcttcagttt ccctaatccc                                                  20

<210> SEQ ID NO 19
<211> LENGTH: 21
<212> TYPE: DNA
<213> ORGANISM: Artificial Sequence
<220> FEATURE:
<223> OTHER INFORMATION: Sequence of a 2RC2 Primer for Cap Site
      Sequencing.

<400> SEQUENCE: 19
gtacgccaca gcgtatgatg c                                                21

<210> SEQ ID NO 20
<211> LENGTH: 21
<212> TYPE: DNA
<213> ORGANISM: Artificial Sequence
<220> FEATURE:
<223> OTHER INFORMATION: Sequence of a Synthetic TGP2 Primer for Cap
      Site Sequencing.

<400> SEQUENCE: 20
cattcttgac aaacttcata g                                                21

<210> SEQ ID NO 21
<211> LENGTH: 21
<212> TYPE: DNA
<213> ORGANISM: Artificial Sequence
<220> FEATURE:
<223> OTHER INFORMATION: Sequence of a Primer.

<400> SEQUENCE: 21
atcttgctgc agattcgtga c                                                21

<210> SEQ ID NO 22
<211> LENGTH: 15
<212> TYPE: DNA
<213> ORGANISM: Artificial Sequence
<220> FEATURE:
<223> OTHER INFORMATION: Sequence of a lambda gt11 5' Sequencing Primer.

<400> SEQUENCE: 22
gactcctgga gcccg                                                       15

<210> SEQ ID NO 23
<211> LENGTH: 2256
<212> TYPE: DNA
<213> ORGANISM: Homo Sapiens
<220> FEATURE:
<221> NAME/KEY: CDS
<222> LOCATION: (74)..(1927)

<400> SEQUENCE: 23 gggggacga cttcctcggc tgcgcggcgc tcgcgcggag ctccccggcc ggcggtgcgt        60
ccccacggtc acc atg aaa gac gac ttc gca gag gag gag gag gtg caa       109
            Met Lys Asp Asp Phe Ala Glu Glu Glu Glu Val Gln
              1               5                  10 tcc ttc ggt tac aag cgg ttt ggt att cag gaa gga aca caa tgt acc       157
Ser Phe Gly Tyr Lys Arg Phe Gly Ile Gln Glu Gly Thr Gln Cys Thr
         15                  20                  25

```
aaa tgt aaa aat aac tgg gca ctg aag ttt tct atc ata tta tta tac    205
Lys Cys Lys Asn Asn Trp Ala Leu Lys Phe Ser Ile Ile Leu Leu Tyr
 30              35                  40 att ttg tgt gcc ttg cta aca atc aca gta gcc att ttg gga tat aaa    253
Ile Leu Cys Ala Leu Leu Thr Ile Thr Val Ala Ile Leu Gly Tyr Lys
 45              50                  55                  60 gtt gta gag aaa atg gac aat gtc aca ggt ggc atg gaa aca tct cgc    301
Val Val Glu Lys Met Asp Asn Val Thr Gly Gly Met Glu Thr Ser Arg
                 65                  70                  75 caa acc tat gat gac aag ctc aca gca gtg gaa agt gac ctg aaa aaa    349
Gln Thr Tyr Asp Asp Lys Leu Thr Ala Val Glu Ser Asp Leu Lys Lys
                 80                  85                  90 tta ggt gac caa act ggg aag aaa gct atc agc acc aac tca gaa ctc    397
Leu Gly Asp Gln Thr Gly Lys Lys Ala Ile Ser Thr Asn Ser Glu Leu
         95                 100                 105 tcc acc ttc aga tca gac att cta gat ctc cgt cag caa ctt cgt gag    445
Ser Thr Phe Arg Ser Asp Ile Leu Asp Leu Arg Gln Gln Leu Arg Glu
        110                 115                 120 att aca gaa aaa acc agc aag aac aag gat acg ctg gag aag tta cag    493
Ile Thr Glu Lys Thr Ser Lys Asn Lys Asp Thr Leu Glu Lys Leu Gln
125                 130                 135                 140 gcg agc ggg gat gct ctg gtg gac agg cag agt caa ttg aaa gaa act    541
Ala Ser Gly Asp Ala Leu Val Asp Arg Gln Ser Gln Leu Lys Glu Thr
                145                 150                 155 ttg gag aat aac tct ttc ctc atc acc act gta aac aaa acc ctc cag    589
Leu Glu Asn Asn Ser Phe Leu Ile Thr Thr Val Asn Lys Thr Leu Gln
                160                 165                 170 gcg tat aat ggc tat gtc acg aat ctg cag caa gat acc agc gtg ctc    637
Ala Tyr Asn Gly Tyr Val Thr Asn Leu Gln Gln Asp Thr Ser Val Leu
        175                 180                 185 cag ggc aat ctg cag aac caa atg tat tct cat aat gtg gtc atc atg    685
Gln Gly Asn Leu Gln Asn Gln Met Tyr Ser His Asn Val Val Ile Met
        190                 195                 200 aac ctc aac aac ctg aac ctg acc cag gtg cag cag agg aac ctc atc    733
Asn Leu Asn Asn Leu Asn Leu Thr Gln Val Gln Gln Arg Asn Leu Ile
205                 210                 215                 220 acg aat ctg cag cgg tct gtg gat gac aca agc cag gct atc cag cga    781
Thr Asn Leu Gln Arg Ser Val Asp Asp Thr Ser Gln Ala Ile Gln Arg
                225                 230                 235 atc aag aac gac ttt caa aat ctg cag cag gtt ttt ctt caa gcc aag    829
Ile Lys Asn Asp Phe Gln Asn Leu Gln Gln Val Phe Leu Gln Ala Lys
                240                 245                 250 aag gac acg gat tgg ctt aag gag aaa gtg cag agc ttg cag acg ctg    877
Lys Asp Thr Asp Trp Leu Lys Glu Lys Val Gln Ser Leu Gln Thr Leu
        255                 260                 265 gct gcc aac aac tct gcg ttg gcc aaa gcc aac aac gac acc ctg gag    925
Ala Ala Asn Asn Ser Ala Leu Ala Lys Ala Asn Asn Asp Thr Leu Glu
        270                 275                 280 gat atg aac agc cag ctc aac tca ttc aca ggt cag atg gag aac atc    973
Asp Met Asn Ser Gln Leu Asn Ser Phe Thr Gly Gln Met Glu Asn Ile
285                 290                 295                 300 acc act atc tct caa gcc aac gag cag aac ctg aaa gac ctg cag gac   1021
Thr Thr Ile Ser Gln Ala Asn Glu Gln Asn Leu Lys Asp Leu Gln Asp
                305                 310                 315 tta cac aaa gat gca gag aat aga aca gcc atc aag ttc aac caa ctg   1069
Leu His Lys Asp Ala Glu Asn Arg Thr Ala Ile Lys Phe Asn Gln Leu
                320                 325                 330 gag gaa cgc ttc cag ctc ttt gag acg gat att gtg aac atc att agc   1117
Glu Glu Arg Phe Gln Leu Phe Glu Thr Asp Ile Val Asn Ile Ile Ser
        335                 340                 345
```

```
                                              -continued aat atc agt tac aca gcc cac cac ctg cgg acg ctg acc agc aat cta      1165
Asn Ile Ser Tyr Thr Ala His His Leu Arg Thr Leu Thr Ser Asn Leu
    350                 355                 360 aat gaa gtc agg acc act tgc aca gat acc ctt acc aaa cac aca gat      1213
Asn Glu Val Arg Thr Thr Cys Thr Asp Thr Leu Thr Lys His Thr Asp
365                 370                 375                 380 gat ctg acc tcc ttg aat aat acc ctg gcc aac atc cgt ttg gat tct      1261
Asp Leu Thr Ser Leu Asn Asn Thr Leu Ala Asn Ile Arg Leu Asp Ser
                385                 390                 395 gtt tct ctc agg atg caa caa gat ttg atg agg tcg agg tta gac act      1309
Val Ser Leu Arg Met Gln Gln Asp Leu Met Arg Ser Arg Leu Asp Thr
            400                 405                 410 gaa gta gcc aac tta tca gtg att atg gaa gaa atg aag cta gta gac      1357
Glu Val Ala Asn Leu Ser Val Ile Met Glu Glu Met Lys Leu Val Asp
        415                 420                 425 tcc aag cat ggt cag ctc atc aag aat ttt aca ata cta caa ggt cca      1405
Ser Lys His Gly Gln Leu Ile Lys Asn Phe Thr Ile Leu Gln Gly Pro
    430                 435                 440 ccg ggc ccc agg ggt cca aga ggt gac aga gga tcc cag gga ccc cct      1453
Pro Gly Pro Arg Gly Pro Arg Gly Asp Arg Gly Ser Gln Gly Pro Pro
445                 450                 455                 460 ggc cca act ggc aac aag gga cag aaa gga gag aag ggg gag cct gga      1501
Gly Pro Thr Gly Asn Lys Gly Gln Lys Gly Glu Lys Gly Glu Pro Gly
                465                 470                 475 cca cct ggc cct gcg ggc tgc ccg cct cac tgg aag aac ttc aca gac      1549
Pro Pro Gly Pro Ala Gly Cys Pro Pro His Trp Lys Asn Phe Thr Asp
            480                 485                 490 aaa tgc tac tat ttt tca gtt gag aaa gaa att ttt gag gat gca aag      1597
Lys Cys Tyr Tyr Phe Ser Val Glu Lys Glu Ile Phe Glu Asp Ala Lys
        495                 500                 505 ctt ttc tgt gaa gac aag tct tca cat ctt gtt ttc ata aac act aga      1645
Leu Phe Cys Glu Asp Lys Ser Ser His Leu Val Phe Ile Asn Thr Arg
    510                 515                 520 gag gaa cag caa tgg ata aaa aaa cag atg gta ggg aga gag agc cac      1693
Glu Glu Gln Gln Trp Ile Lys Lys Gln Met Val Gly Arg Glu Ser His
525                 530                 535                 540 tgg atc ggc ctc aca gac tca gag cgt gaa aat gaa tgg aag tgg ctg      1741
Trp Ile Gly Leu Thr Asp Ser Glu Arg Glu Asn Glu Trp Lys Trp Leu
                545                 550                 555 gat ggg aca tct cca gac tac aaa aat tgg aaa gct gga cag ccg gat      1789
Asp Gly Thr Ser Pro Asp Tyr Lys Asn Trp Lys Ala Gly Gln Pro Asp
            560                 565                 570 aac tgg ggt cat ggc cat ggg cca gga gaa gac tgt gct ggg ttg att      1837
Asn Trp Gly His Gly His Gly Pro Gly Glu Asp Cys Ala Gly Leu Ile
        575                 580                 585 tat gct ggg cag tgg aac gat ttc caa tgt gaa gac gtc aat aac ttc      1885
Tyr Ala Gly Gln Trp Asn Asp Phe Gln Cys Glu Asp Val Asn Asn Phe
    590                 595                 600 att tgc gaa aaa gac agg gag aca gta ctg tca tct gca tta               1927
Ile Cys Glu Lys Asp Arg Glu Thr Val Leu Ser Ser Ala Leu
605                 610                 615 taacggactg tgatgggatc acatgagcaa attttcagct ctcaaaggca aaggacactc    1987
ctttctaatt gcatcacctt tcatcagat tgaaaaaaaa aaaagcactg aaaaccaatt     2047
actgaaaaaa aattgacagc tagtgttttt taccatccgt cattacccaa agacttggga   2107
actaaaatgt tccccagggt gatatgctga ttttcattgt gcacatggac tgaatcacat   2167
agattctcct ccgtcagtaa ccgtgcgatt atacaaatta tgtcttccaa agtatggaac   2227
```

-continued actccaatca gaaaaaggtt atcatcccg 2256

<210> SEQ ID NO 24
<211> LENGTH: 618
<212> TYPE: PRT
<213> ORGANISM: Homo Sapiens
<220> FEATURE:
<223> OTHER INFORMATION: Deduced Amino Acid Sequence of Mutated Novel
      Human Scavenger Receptor from Nucleotide Sequence.

<400> SEQUENCE: 24

```
Met Lys Asp Asp Phe Ala Glu Glu Glu Val Gln Ser Phe Gly Tyr
  1               5                  10                  15

Lys Arg Phe Gly Ile Gln Glu Gly Thr Gln Cys Thr Lys Cys Lys Asn
                 20                  25                  30

Asn Trp Ala Leu Lys Phe Ser Ile Ile Leu Leu Tyr Ile Leu Cys Ala
             35                  40                  45

Leu Leu Thr Ile Thr Val Ala Ile Leu Gly Tyr Lys Val Val Glu Lys
         50                  55                  60

Met Asp Asn Val Thr Gly Gly Met Glu Thr Ser Arg Gln Thr Tyr Asp
 65                  70                  75                  80

Asp Lys Leu Thr Ala Val Glu Ser Asp Leu Lys Lys Leu Gly Asp Gln
                 85                  90                  95

Thr Gly Lys Lys Ala Ile Ser Thr Asn Ser Glu Leu Ser Thr Phe Arg
            100                 105                 110

Ser Asp Ile Leu Asp Leu Arg Gln Gln Leu Arg Glu Ile Thr Glu Lys
        115                 120                 125

Thr Ser Lys Asn Lys Asp Thr Leu Glu Lys Leu Gln Ala Ser Gly Asp
    130                 135                 140

Ala Leu Val Asp Arg Gln Ser Gln Leu Lys Glu Thr Leu Glu Asn Asn
145                 150                 155                 160

Ser Phe Leu Ile Thr Thr Val Asn Lys Thr Leu Gln Ala Tyr Asn Gly
                165                 170                 175

Tyr Val Thr Asn Leu Gln Gln Asp Thr Ser Val Leu Gln Gly Asn Leu
            180                 185                 190

Gln Asn Gln Met Tyr Ser His Asn Val Val Ile Met Asn Leu Asn Asn
        195                 200                 205

Leu Asn Leu Thr Gln Val Gln Gln Arg Asn Leu Ile Thr Asn Leu Gln
    210                 215                 220

Arg Ser Val Asp Asp Thr Ser Gln Ala Ile Gln Arg Ile Lys Asn Asp
225                 230                 235                 240

Phe Gln Asn Leu Gln Gln Val Phe Leu Gln Ala Lys Lys Asp Thr Asp
                245                 250                 255

Trp Leu Lys Glu Lys Val Gln Ser Leu Gln Thr Leu Ala Ala Asn Asn
            260                 265                 270

Ser Ala Leu Ala Lys Ala Asn Asn Asp Thr Leu Glu Asp Met Asn Ser
        275                 280                 285

Gln Leu Asn Ser Phe Thr Gly Gln Met Glu Asn Ile Thr Thr Ile Ser
    290                 295                 300

Gln Ala Asn Glu Gln Asn Leu Lys Asp Leu Gln Asp Leu His Lys Asp
305                 310                 315                 320

Ala Glu Asn Arg Thr Ala Ile Lys Phe Asn Gln Leu Glu Glu Arg Phe
                325                 330                 335

Gln Leu Phe Glu Thr Asp Ile Val Asn Ile Ile Ser Asn Ile Ser Tyr
            340                 345                 350
```

```
Thr Ala His His Leu Arg Thr Leu Thr Ser Asn Leu Asn Glu Val Arg
        355                 360                 365

Thr Thr Cys Thr Asp Thr Leu Thr Lys His Thr Asp Asp Leu Thr Ser
370                 375                 380

Leu Asn Asn Thr Leu Ala Asn Ile Arg Leu Asp Ser Val Ser Leu Arg
385                 390                 395                 400

Met Gln Gln Asp Leu Met Arg Ser Arg Leu Asp Thr Glu Val Ala Asn
        405                 410                 415

Leu Ser Val Ile Met Glu Glu Met Lys Leu Val Asp Ser Lys His Gly
            420                 425                 430

Gln Leu Ile Lys Asn Phe Thr Ile Leu Gln Gly Pro Pro Gly Pro Arg
        435                 440                 445

Gly Pro Arg Gly Asp Arg Gly Ser Gln Gly Pro Pro Gly Pro Thr Gly
    450                 455                 460

Asn Lys Gly Gln Lys Gly Glu Lys Gly Glu Pro Gly Pro Pro Gly Pro
465                 470                 475                 480

Ala Gly Cys Pro Pro His Trp Lys Asn Phe Thr Asp Lys Cys Tyr Tyr
            485                 490                 495

Phe Ser Val Glu Lys Glu Ile Phe Glu Asp Ala Lys Leu Phe Cys Glu
                500                 505                 510

Asp Lys Ser Ser His Leu Val Phe Ile Asn Thr Arg Glu Glu Gln Gln
        515                 520                 525

Trp Ile Lys Lys Gln Met Val Gly Arg Glu Ser His Trp Ile Gly Leu
    530                 535                 540

Thr Asp Ser Glu Arg Glu Asn Glu Trp Lys Trp Leu Asp Gly Thr Ser
545                 550                 555                 560

Pro Asp Tyr Lys Asn Trp Lys Ala Gly Gln Pro Asp Asn Trp Gly His
            565                 570                 575

Gly His Gly Pro Gly Glu Asp Cys Ala Gly Leu Ile Tyr Ala Gly Gln
                580                 585                 590

Trp Asn Asp Phe Gln Cys Glu Asp Val Asn Asn Phe Ile Cys Glu Lys
        595                 600                 605

Asp Arg Glu Thr Val Leu Ser Ser Ala Leu
    610                 615

<210> SEQ ID NO 25
<211> LENGTH: 30
<212> TYPE: DNA
<213> ORGANISM: Artificial Sequence
<220> FEATURE:
<223> OTHER INFORMATION: Sequence of a Primer for PCR Amplification of
      hSRCL-P1.

<400> SEQUENCE: 25
ccgctcgagc ggtcaccatg aaagacgact                                      30

<210> SEQ ID NO 26
<211> LENGTH: 30
<212> TYPE: DNA
<213> ORGANISM: Artificial Sequence
<220> FEATURE:
<223> OTHER INFORMATION: Sequence of a Primer for PCR Amplification of
      hSRCL-P1.

<400> SEQUENCE: 26
tccccgcggt aatgcagatg acagtactgt                                      30

<210> SEQ ID NO 27
```

<211> LENGTH: 35
<212> TYPE: DNA
<213> ORGANISM: Artificial Sequence
<220> FEATURE:
<223> OTHER INFORMATION: Sequence of a Primer for PCR Amplification of hSRCL-P1.

<400> SEQUENCE: 27
aatgcggccg caccatgaaa gacgacttcg cagag                                    35

<210> SEQ ID NO 28
<211> LENGTH: 32
<212> TYPE: DNA
<213> ORGANISM: Artificial Sequence
<220> FEATURE:
<223> OTHER INFORMATION: Sequence of a Primer for PCR Amplification of hSRCL-P1.

<400> SEQUENCE: 28
gctctagacc gcggtaatgc agatgacagt ac                                       32

<210> SEQ ID NO 29
<211> LENGTH: 248
<212> TYPE: PRT
<213> ORGANISM: Homo sapiens

<400> SEQUENCE: 29

```
Met Ser Leu Phe Pro Ser Leu Pro Leu Leu Leu Ser Met Val Ala
 1               5                  10                  15

Ala Ser Tyr Ser Glu Thr Val Thr Cys Glu Asp Ala Gln Lys Thr Cys
                20                  25                  30

Pro Ala Val Ile Ala Cys Ser Ser Pro Gly Ile Asn Gly Phe Pro Gly
            35                  40                  45

Lys Asp Gly Arg Asp Gly Thr Lys Gly Glu Lys Gly Glu Pro Gly Gln
        50                  55                  60

Gly Leu Arg Gly Leu Gln Gly Pro Pro Gly Lys Leu Gly Pro Pro Gly
 65                 70                  75                  80

Asn Pro Gly Pro Ser Gly Ser Pro Gly Pro Lys Gly Gln Lys Gly Asp
                85                  90                  95

Pro Gly Lys Ser Pro Asp Gly Asp Ser Ser Leu Ala Ala Ser Glu Arg
            100                 105                 110

Lys Ala Leu Gln Thr Glu Met Ala Arg Ile Lys Lys Trp Leu Thr Phe
        115                 120                 125

Ser Leu Gly Lys Gln Val Gly Asn Lys Phe Phe Leu Thr Asn Gly Glu
    130                 135                 140

Ile Met Thr Phe Glu Lys Val Lys Ala Leu Cys Val Lys Phe Gln Ala
145                 150                 155                 160

Ser Val Ala Thr Pro Arg Asn Ala Ala Glu Asn Gly Ala Ile Gln Asn
                165                 170                 175

Leu Ile Lys Glu Glu Ala Phe Leu Gly Ile Thr Asp Glu Lys Thr Glu
            180                 185                 190

Gly Gln Phe Val Asp Leu Thr Gly Asn Arg Leu Thr Tyr Thr Asn Trp
        195                 200                 205

Asn Glu Gly Glu Pro Asn Asn Ala Gly Ser Asp Glu Asp Cys Val Leu
    210                 215                 220

Leu Leu Lys Asn Gly Gln Trp Asn Asp Val Pro Cys Ser Thr Ser His
225                 230                 235                 240

Leu Ala Val Cys Glu Phe Pro Ile
                245
```

<210> SEQ ID NO 30
<211> LENGTH: 248
<212> TYPE: PRT
<213> ORGANISM: Homo sapiens

<400> SEQUENCE: 30

Met Trp Leu Cys Pro Leu Ala Leu Thr Leu Ile Leu Met Ala Ala Ser
1               5                   10                  15

Gly Ala Ala Cys Glu Val Lys Asp Val Cys Val Gly Ser Pro Gly Ile
            20                  25                  30

Pro Gly Thr Pro Gly Ser His Gly Leu Pro Gly Arg Asp Gly Arg Asp
        35                  40                  45

Gly Val Lys Gly Asp Pro Gly Pro Pro Gly Pro Met Gly Pro Pro Gly
50                  55                  60

Glu Thr Pro Cys Pro Pro Gly Asn Asn Gly Leu Pro Gly Ala Pro Gly
65                  70                  75                  80

Val Pro Gly Glu Arg Gly Glu Lys Gly Glu Pro Gly Glu Arg Gly Pro
                85                  90                  95

Pro Gly Leu Pro Ala His Leu Asp Glu Glu Leu Gln Ala Thr Leu His
            100                 105                 110

Asp Phe Arg His Gln Ile Leu Gln Thr Arg Gly Ala Leu Ser Leu Gln
        115                 120                 125

Gly Ser Ile Met Thr Val Gly Glu Lys Val Phe Ser Ser Asn Gly Gln
130                 135                 140

Ser Ile Thr Phe Asp Ala Ile Gln Glu Ala Cys Ala Arg Ala Gly Gly
145                 150                 155                 160

Arg Ile Ala Val Pro Arg Asn Pro Glu Glu Asn Glu Ala Ile Ala Ser
                165                 170                 175

Phe Val Lys Lys Tyr Asn Thr Tyr Ala Tyr Val Gly Leu Thr Glu Gly
            180                 185                 190

Pro Ser Pro Gly Asp Phe Arg Tyr Ser Asp Gly Thr Pro Val Asn Tyr
        195                 200                 205

Thr Asn Trp Tyr Arg Gly Glu Pro Ala Gly Arg Gly Lys Glu Gln Cys
210                 215                 220

Val Glu Met Tyr Thr Asp Gly Gln Trp Asn Asp Arg Asn Cys Leu Tyr
225                 230                 235                 240

Ser Arg Leu Thr Ile Cys Glu Phe
                245

<210> SEQ ID NO 31
<211> LENGTH: 376
<212> TYPE: PRT
<213> ORGANISM: Homo sapiens

<400> SEQUENCE: 31

Met Leu Leu Phe Leu Leu Ser Ala Leu Val Leu Leu Thr Gln Pro Leu
1               5                   10                  15

Gly Tyr Leu Glu Ala Glu Met Lys Thr Tyr Ser His Arg Thr Thr Pro
            20                  25                  30

Ser Ala Cys Thr Leu Val Met Cys Ser Ser Val Glu Ser Gly Leu Pro
        35                  40                  45

Gly Arg Asp Gly Arg Asp Gly Arg Glu Gly Pro Arg Gly Glu Lys Gly
50                  55                  60

Asp Pro Gly Leu Pro Gly Ala Ala Gly Gln Ala Gly Met Pro Gly Gln
65                  70                  75                  80

-continued

```
Ala Gly Pro Val Gly Pro Lys Gly Asp Asn Gly Ser Val Gly Glu Pro
             85                  90                  95
Gly Pro Lys Gly Asp Thr Gly Pro Ser Gly Pro Pro Gly Pro Pro Gly
            100                 105                 110
Val Pro Gly Pro Ala Gly Arg Glu Gly Pro Leu Gly Lys Gln Gly Asn
            115                 120                 125
Ile Gly Pro Gln Gly Lys Pro Gly Pro Lys Gly Glu Ala Gly Pro Lys
        130                 135                 140
Gly Glu Val Gly Ala Pro Gly Met Gln Gly Ser Ala Gly Ala Arg Gly
145                 150                 155                 160
Leu Ala Gly Pro Lys Gly Glu Arg Gly Val Pro Gly Glu Arg Gly Val
                165                 170                 175
Pro Gly Asn Ala Gly Ala Ala Gly Ser Ala Gly Ala Met Gly Pro Gln
            180                 185                 190
Gly Ser Pro Gly Ala Arg Gly Pro Pro Gly Leu Lys Gly Asp Lys Gly
            195                 200                 205
Ile Pro Gly Asp Lys Gly Ala Lys Gly Glu Ser Gly Leu Pro Asp Val
        210                 215                 220
Ala Ser Leu Arg Gln Gln Val Glu Ala Leu Gln Gly Gln Val Gln His
225                 230                 235                 240
Leu Gln Ala Ala Phe Ser Gln Tyr Lys Lys Val Glu Leu Phe Pro Asn
                245                 250                 255
Gly Gln Ser Val Gly Glu Lys Ile Phe Lys Thr Ala Gly Phe Val Lys
            260                 265                 270
Pro Phe Thr Glu Ala Gln Leu Leu Cys Thr Gln Ala Gly Gly Gln Leu
            275                 280                 285
Ala Ser Pro Arg Ser Ser Ala Ala Glu Asn Ala Ala Leu Gln Gln Leu
        290                 295                 300
Val Val Ala Lys Asn Glu Ala Ala Phe Leu Ser Met Thr Asp Ser Lys
305                 310                 315                 320
Thr Glu Gly Lys Phe Thr Tyr Pro Thr Gly Glu Ser Leu Val Tyr Ser
                325                 330                 335
Asn Trp Ala Pro Gly Glu Pro Asn Asp Asp Gly Gly Ser Glu Asp Cys
            340                 345                 350
Val Glu Ile Phe Thr Asn Gly Lys Trp Asn Asp Arg Ala Cys Gly Glu
            355                 360                 365
Lys Arg Leu Val Val Cys Glu Phe
        370                 375
```